(12) United States Patent
Mackenzie et al.

(10) Patent No.: US 8,101,605 B2
(45) Date of Patent: Jan. 24, 2012

(54) SHIP1 MODULATORS AND METHODS RELATED THERETO

(75) Inventors: Lloyd Mackenzie, Surrey (CA); Tom MacRury, Point Roberts, WA (US); Curtis Harwig, Vancouver (CA); Jeremy Pettigrew, Burnaby (CA); Noor Aini Bhatti, Coquitlam (CA); Sam Place, Edmonton (CA); Paul Bird, Edmonton (CA); Vladimir Khlebnikov, Edmonton (CA); Rudong Shan, Edmonton (CA)

(73) Assignee: Aquinox Pharmaceuticals Inc., Richmond, British Columbia (CA)

( * ) Notice: Subject to any disclaimer, the term of this patent is extended or adjusted under 35 U.S.C. 154(b) by 0 days.

(21) Appl. No.: 12/960,318

(22) Filed: Dec. 3, 2010

(65) Prior Publication Data

US 2011/0136802 A1    Jun. 9, 2011

Related U.S. Application Data

(60) Provisional application No. 61/266,964, filed on Dec. 4, 2009.

(51) Int. Cl.
*C07D 311/78* (2006.01)
*C07D 335/04* (2006.01)
*A61K 31/352* (2006.01)
*A61K 31/382* (2006.01)

(52) U.S. Cl. ............. 514/232.8; 514/254.11; 514/432; 514/453; 544/145; 544/375; 546/202; 549/24; 549/25; 549/384

(58) Field of Classification Search .......... None
See application file for complete search history.

(56) References Cited

U.S. PATENT DOCUMENTS

2002/0137711 A1*    9/2002    Kerr ....................... 514/44

FOREIGN PATENT DOCUMENTS

| WO | WO 03/033517 A1 | 4/2003 |
| WO | WO 2004/035601 A1 | 4/2004 |
| WO | WO 2007/147251 A1 | 12/2007 |
| WO | WO 2007/147252 A1 | 12/2007 |

OTHER PUBLICATIONS

Yang, Lu et al., "Synthesis of Pelorol and Analogues: Activators of the Inositol 5-Phosphatase SHIP", Organic Letters, 7(6), 1073-1076, 2005.*
Goclik et al., "Pelorol from the Tropical Marine Sponge *Dactylospongia elegans*," *J Nat Prod* 63(8): 1150-1152, 2000.
Kwak et al., "Sesquiterpene Quinols/Quinones from the Micronesian Sponge *Petrosaspongia metachromia*," *J Nat Prod* 63(8): 1153-1156, 2000.

* cited by examiner

*Primary Examiner* — Fiona T Powers
(74) *Attorney, Agent, or Firm* — Seed IP Law Group PLLC

(57) ABSTRACT

Compounds of structure (I):

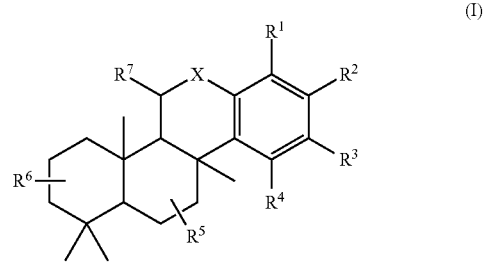

including stereoisomers and pharmaceutically acceptable salts thereof, wherein X, $R^1$, $R^2$, $R^3$, $R^4$, $R^5$, $R^6$ and $R^7$ are as defined herein. Such compounds have activity as SHIP1 modulators, and thus may be used to treat any of a variety of diseases, disorders or conditions that would benefit from SHIP1 modulation. Compositions comprising a compound of structure (I) in combination with a pharmaceutically acceptable carrier or diluent are also disclosed, as are methods of SHIP1 modulation by administration of such compounds to an animal in need thereof.

17 Claims, No Drawings

SHIP1 MODULATORS AND METHODS RELATED THERETO

BACKGROUND

1. Technical Field

The present invention is generally directed to SHIP1 modulators, as well as to compositions and methods related to the same.

2. Description of the Related Art

In response to extracellular signals, phosphoinositide 3-kinase (PI3K) becomes activated and phosphorylates phosphatidylinositol-4,5-bisphosphate (PI-4,5-$P_2$) within the plasma membrane to generate phosphatidylinositol-3,4,5-trisphosphate ($PIP_3$). $PIP_3$ then initiates a cascade of downstream signaling pathways by interacting with pleckstrin homology (PH) domain-containing proteins, such as protein kinase B (PKB, also known as Akt), that regulate cellular activation, function, proliferation and/or survival, depending on the cell type and stimulus (Deane et al., *Annu Rev Immunol* 22, 563-598, 2004). Cellular levels of $PIP_3$ are normally tightly regulated by the PI3K enzymes, the 5' SH2 domain-containing inositol phosphatase (SHIP) enzymes SHIP1 and SHIP2, and by the 3' phosphatase and tensin homolog (PTEN). SHIP1 and SHIP2, dephosphorylate $PIP_3$ to phosphatidylinositol-3,4-bisphosphate (PI-3,4-$P_2$), whereas PTEN dephosphorylates $PIP_3$ to PI-4,5-$P_2$ (Sly et al., *Exp Hematol* 31, 1170-1181, 2003; Vivanco et al., *Nat Rev Cancer* 2, 489-501, 2002). Of these, SHIP1 is unique in that its expression is restricted primarily to immune and hematopoietic cells (Sly et al., *Exp Hematol* 31, 1170-1181, 2003; Damen et al., *Proc Natl Acad Sci USA* 93, 1689-1693, 1996).

The role of SHIP1 in immune cell homeostasis is shown both by the myeloproliferative syndrome observed in SHIP1$^{-/-}$ mice, as well as the hypersensitivity of SHIP1$^{-/-}$ mice and cells to immune stimulation (Helgason et al., *Genes Dev* 12, 1610-1620, 1998; Sly et al., *Immunity* 21, 227-239, 2004). SHIP1 has been shown to mediate signaling from the inhibitory FcγRIIB receptor (Coggeshall et al., *Mol Immunol* 39, 521-529, 2002), and is important in terminating signal transduction from activating immune/hematopoietic cell receptor systems (Kalesnikoff et al., *Rev Physiol Biochem Pharmacol* 149, 87-103, 2003).

Diminished SHIP1 activity or expression has been observed in human inflammatory diseases (Vonakis et al., *J Allergy Clin Immunol* 108, 822-831, 2001) and hematopoietic malignancies (Liang et al., *Proteomics* 6, 4554-4564, 2006; Fukuda et al., *Proc Natl Acad Sci USA* 102, 15213-15218, 2005; Luo et al., *Zhongguo Shi Yan Xue Ye Xue Za Zhi* 12, 420-426, 2004; Vanderwinden et al., *Cell Signal* 18, 661-669, 2006).

Because dysregulated activation of the PI3K pathway contributes to inflammatory/immune disorders and cancer, intense efforts have been invested into the development of inhibitors of the PI3K enzymes, as well as downstream protein kinases (Workman et al., *Nat Biotechnol* 24, 794-796, 2006; Simon, *Cell* 125, 647-649, 2006; Hennessy et al., *Nat Rev Drug Discov* 4, 988-1004, 2005; Knight et al., *Cell* 125, 733-747, 2006). The precedent for discovery and biologic efficacy of kinase inhibitors is well established, and a number of promising new PI3K isoform-specific inhibitors have recently been developed and used in mouse models of inflammatory disease (Camps et al., *Nat Med* 11, 936-943, 2005; Barber et al., *Nat Med* 11, 933-935, 2005) and glioma (Fan et al., *Cancer Cell* 9, 341-349, 2006) with minimal toxicities. However, because of the dynamic interplay between phosphatases and kinases in regulating biologic processes, inositol phosphatase activators represent a complementary, alternative approach to reduce cellular $PIP_3$ levels. Of the phosphoinositol phosphatases that degrade $PIP_3$, SHIP1 is a particularly ideal target for development of therapeutics for treating immune and hemopoetic disorders because its hematopoietic-restricted expression would limit the effects of a specific SHIP1 activator to cells that express the enzyme.

To date, a number of small molecule SHIP1 modulators have been disclosed, including sesquiterpene compounds such as pelorol. Pelorol is a natural product isolated from the topical marine sponge *Dactylospongia elegans* (Kwak et al., *J Nat Prod* 63, 1153-1156, 2000; Goclik et al., *J Nat Prod* 63, 1150-1152, 2000). Other reported SHIP1 modulators include the compounds set forth in WO2003/033517, WO2004/035601, WO2007/147251 and WO2007/147252.

While significant strides have been made in this field, there remains a need for effective small molecule SHIP1 modulators. There is also a need for pharmaceutical compositions containing such compounds, as well as for methods relating to the use thereof to treat disorders or conditions that would benefit from SHIP1 modulation. The present invention fulfills these needs, and provides other related advantages.

BRIEF SUMMARY

In brief, this invention is generally directed to compounds having the following structure (I):

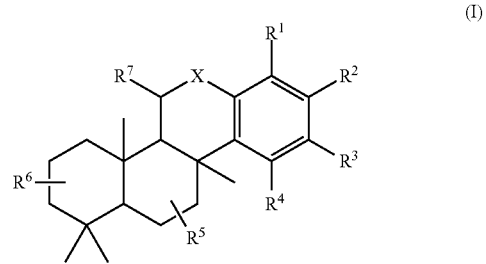

including stereoisomers and pharmaceutically acceptable salts thereof, wherein X, $R^1$, $R^2$, $R^3$, $R^4$, $R^5$, $R^6$ and $R^7$ are as defined below.

Compounds of structure (I) above have activity as SHIP1 modulators and utility over a wide range of therapeutic applications, and may be used to treat any of a variety of disorders or conditions that would benefit from SHIP1 modulation. For example, such disorders or conditions include (but are not limited to) autoimmune diseases such as idiopathic pulmonary fibrosis, inflammatory bowel disease (including Crohn's Disease and ulcerative colitis), rheumatoid arthritis, Still's Disease, Sjögren's Syndrome, systemic lupus erythematosus, and systemic sclerosis; inflammatory diseases such as allergic rhinitis, Alzheimer's Disease, asthma, ocular inflammatory diseases (including allergic conjunctivitis, dry eye, and uveitis), chronic obstructive pulmonary disease, eczema, post operative inflammation, multiple sclerosis, psoriasis, seronegative spondyloarthropathies (including anklyosing spondylitis, psoriatic arthritis, and Reiter's Syndrome), and vasculitis (including Wegener's Granulomatosis, polyarteritis nodosa, leucocytoclastic vasculitis, Churg-Strauss Syndrome, cryoglobulinemic vasculitis and giant cell arteritis); and neoplastic diseases or other cell proliferative disorders such as acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

Methods of this invention include administering an effective amount of a compound of structure (I), typically in the form of a pharmaceutical composition, to an animal in need thereof, including a mammal (such as a human). Accordingly, in another embodiment, pharmaceutical compositions are disclosed containing one or more compounds of structure (I) in combination with a pharmaceutically acceptable carrier and/or diluent.

Compounds of structure (I) may also be used as a medicament. Other embodiments include use of a compound of structure (I) for manufacture of a medicament for modulating SHIP1.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

As mentioned above, this invention is generally directed to small molecule modulators of SHIP1, as well as to corresponding compositions and methods of use. As used herein, a SHIP1 modulator can serve as either an activator or antagonist to SHIP1.

In one embodiment, compounds are disclosed which have the following structure (I):

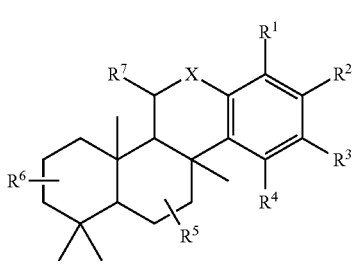

including stereoisomers and pharmaceutically acceptable salts thereof, wherein:

X is O or $S(O)_p$ where p is 0, 1 or 2;

$R^1$, $R^2$, $R^3$, $R^4$, $R^5$ and $R^6$ are independently hydrogen, halogen, hydroxyl, cyano, alkyl, alkoxy, —$COOR^8$, —$NR^9R^{10}$, —$CONR^{11}R^{12}$, $NR^{13}COR^{14}$ or —$OSO_2R^{15}$;

$R^7$ is hydrogen; and $R^8$, $R^9$, $R^{10}$, $R^{11}$, $R^{12}$, $R^{13}$, $R^{14}$ and $R^{15}$ are independently hydrogen, alkyl or alkoxy, or $R^9/R^{10}$ or $R^{11}/R^{12}$ taken together with the nitrogen to which they are attached form a heterocycle.

As used herein, the following terms have the meanings set forth below.

"Alkyl" means an optionally substituted, straight chain or branched, noncyclic or cyclic, unsaturated or saturated aliphatic hydrocarbon containing from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkoxy" means an alkyl moiety as defined above (i.e., an optionally substituted, straight chain or branched, noncyclic or cyclic, unsaturated or saturated aliphatic hydrocarbon containing from 1 to 10 carbon atoms) attached through an oxygen bridge (i.e., —O-alkyl) such as methoxy, ethoxy, and the like.

"Heterocycle" (also referred to herein as a "heterocycle ring") means an optionally substituted 5- to 7-membered monocyclic, or an optionally substituted 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include "heteroaryl" which is an optionally substituted aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

An "optionally substituted" alkyl or heterocycle means an alkyl moiety as defined above or a heterocycle moiety as defined above, respectively, wherein 0 to 4 hydrogen atoms of the aliphatic hydrocarbon or heterocycle are replaced with a substituent. When zero hydrogen atoms are replaced with a substituent, the alkyl or heterocycle moiety is unsubstituted. When 1 to 4 hydrogen atoms are replaced with a substituent, the alkyl moiety or heterocycle moiety is substituted. In the case of an oxo substituent ("=O") two hydrogen atoms from the same carbon atom are replaced. When substituted, "substituents" within the context of this invention include oxo, halogen, hydroxyl, alkoxy, cyano, nitro, —C(=O)$R^a$, —C(=O)$OR^a$, —C(=O)$NR^bR^c$, —OC(=O)$NR^bR^c$, —$NR^bR^c$, —$NR^aC$(=O)$R^b$, —$NR^aC$(=O)$OR^b$ or —$NR^aC$(=O)$NR^bR^c$, wherein $R^a$, $R^b$ and $R^c$ are the same or different and independently hydrogen or alkyl moiety as defined above, or $R^b$ and $R^c$ are taken together with the nitrogen to which they are attached to form a heterocycle as defined above.

"Amino" means —NH$_2$.

"Hydroxyl" means —OH.

"Cyano" means —CN.

"Nitro" means —NO$_2$.

"Halogen" means fluoro, chloro, bromo and iodo.

In more specific embodiments of structure (I), the compounds have the following structure (II) or (III) when X is O or S(O)$_p$, respectively:

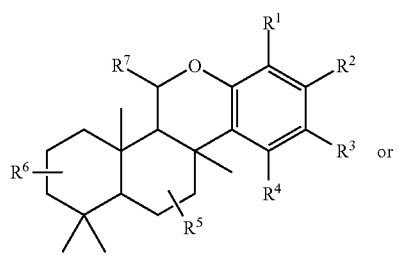

(II)

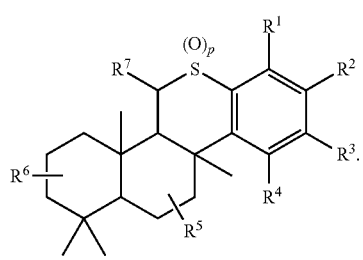

(III)

In more specific embodiments of structure (III), the compounds have the following structure (III-a), (III-b) or (III-c) when p is 0, 1 or 2, respectively:

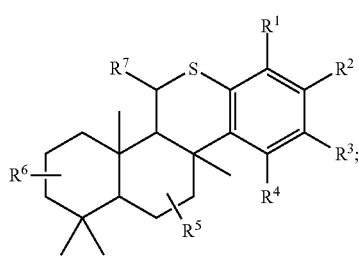

(III-a)

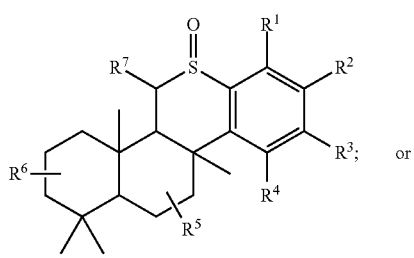

(III-b)

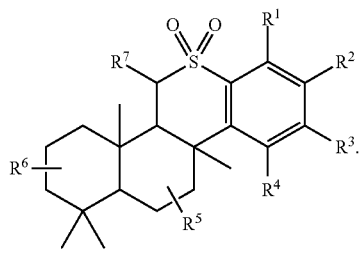

(III-c)

In more specific embodiments of structures (I) through (III), $R^1$, $R^2$, $R^3$ and $R^4$ are independently hydrogen, hydroxyl, alkyl or alkoxy.

In more specific embodiments of structures (I) through (III), $R^1$, $R^2$, $R^3$ and $R^4$ are independently hydrogen, hydroxyl, alkyl, alkoxy, cyano, amino, —COOH or —CONHCH$_3$.

In more specific embodiments of structures (I) through (III), at least one of $R^1$, $R^2$, $R^3$ and $R^4$ is —NR$^9$R$^{10}$ or —CONR$^{11}$R$^{12}$, wherein $R^9$ and $R^{10}$ or $R^{11}$ and $R^{12}$ taken together with the nitrogen to which they are attached form a heterocycle, such as morpholinyl, piperidinyl or piperizinyl, optionally substituted with a substituent as defined above, such as alkyl or —COOH.

In more specific embodiments of structures (I) through (III), at least one of $R^1$, $R^2$, $R^3$ and $R^4$ is —COOR$^8$, —NR$^9$R$^{10}$, —CONR$^{11}$R$^{12}$, —NR$^{13}$COR$^{14}$, wherein $R^8$, $R^9$, $R^{10}$, $R^{11}$, $R^{12}$, $R^{13}$ and $R^{14}$ are independently substituted alkyl or —O-(substituted alkyl) (i.e., alkoxy), wherein the alkyl is substituted with a substituent as defined above, such as —C(=O)R$^a$, —C(=O)OR$^a$, —C(=O)NR$^b$R$^c$, —OC(=O)NR$^b$R$^c$, —NR$^b$R$^c$, —NR$^a$C(=O)R$^b$, —NR$^a$C(=O)OR$^b$ or —NR$^a$C(=O)NR$^b$R$^c$, wherein $R^a$, $R^b$ and $R^c$ are the same or different and independently hydrogen or alkyl moiety as defined above, In more specific embodiments of structures (I) through (III), at least one of $R^1$, $R^2$, $R^3$ and $R^4$ is substituted alkyl or —O-(substituted alkyl) (i.e., alkoxy), wherein the alkyl is substituted with a substituent as defined above, such as —C(=O)R$^a$, —C(=O)OR$^a$, —C(=O)NR$^b$R$^c$, —OC(=O)NR$^b$R$^c$, —NR$^b$R$^c$, —NR$^a$C(=O)R$^b$, —NR$^a$C(=O)OR$^b$ or —NR$^a$C(=O)NR$^b$R$^c$, wherein $R^a$, $R^b$ and $R^c$ are the same or different and independently hydrogen or alkyl moiety as defined above, or $R^b$ and $R^c$ are taken together with the nitrogen to which they are attached to form a heterocycle as defined above.

In more specific embodiments of structures (I) through (III), $R^1$ and $R^2$, $R^2$ and $R^3$ or $R^3$ and $R^4$ are taken together with the carbon atoms to which they are attached to form a heterocycle, wherein the heterocycle is optionally substituted.

In more specific embodiments of structures (I) through (III), $R^5$, $R^6$ and $R^7$ are hydrogen.

The compounds of the present invention may be prepared by known organic synthesis techniques, including the methods described in more detail in the Examples. However in general, the compounds of structure (I) may be made by the following General Reaction Schemes (Scheme 1 and Scheme 2).

General Reaction Schemes

Scheme 1:

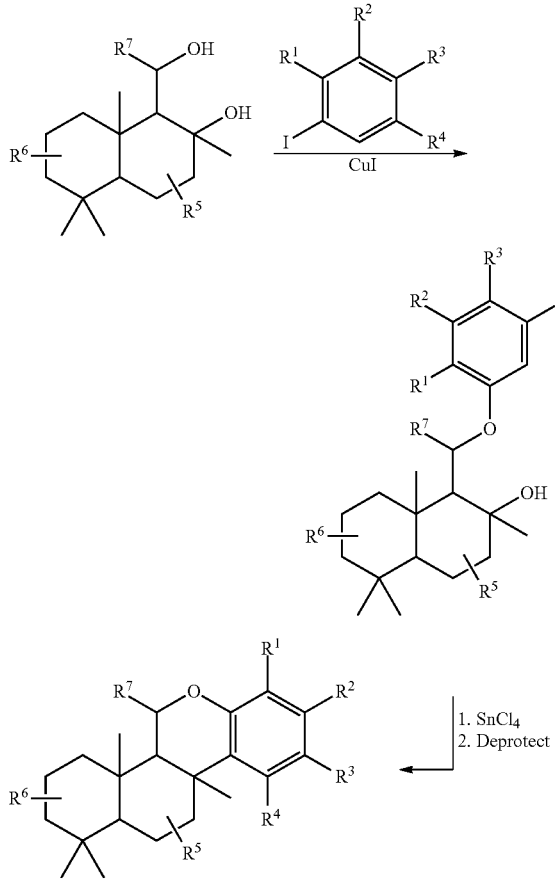

Scheme 2:

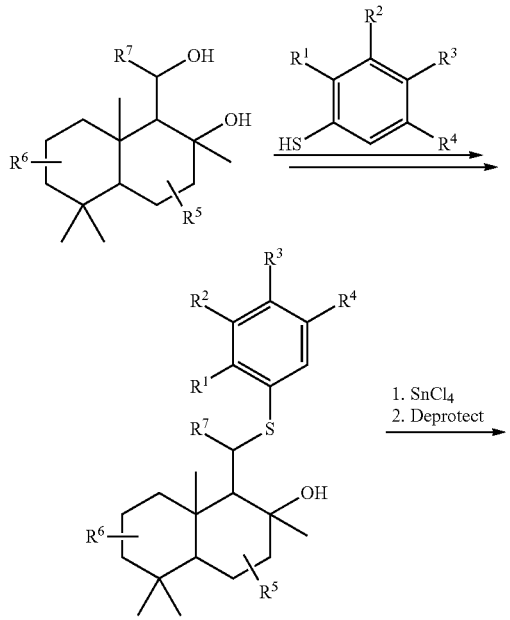

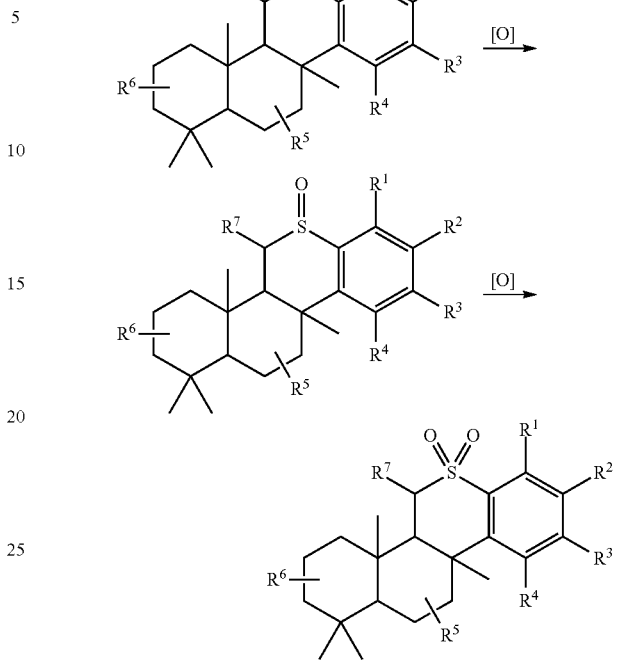

One skilled in the art will recognize that variations to the exact steps outlined in Schemes 1 and 2 are possible. For example, in some embodiments there is no need for a deprotection step. In other embodiments, the order of the oxidation steps may be changed. These and other variations to the steps outlined in Schemes 1 and 2 may be employed in the preparation of compounds of structure (I).

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts include those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, enantiomerically enriched mixtures and as individual enantiomers or diastereomers. All such isomeric forms are included within the present invention, including mixtures thereof. Compounds of structure (I) may also possess axial chirality which may result in atropisomers. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

Specific isomers of the compounds of structure (I) include the following structures:

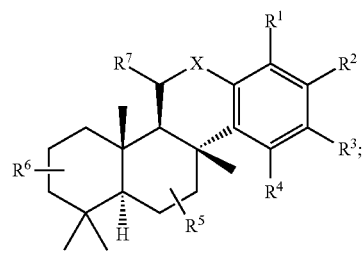

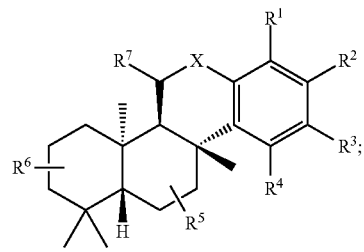

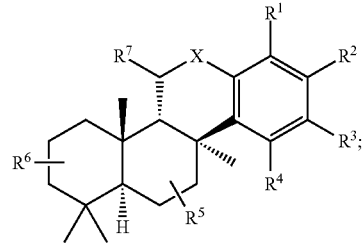

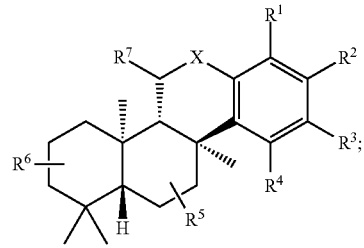

-continued

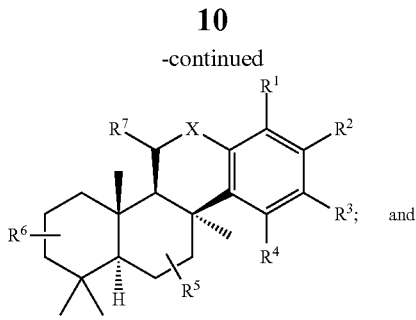

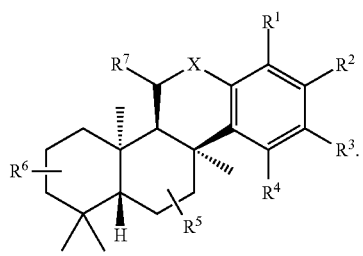

Representative compounds of this invention include (but are not limited to) the compounds listed in Table 1 below.

TABLE 1

Representative Compounds

| Cd. No. | Structure |
|---|---|
| 5 | 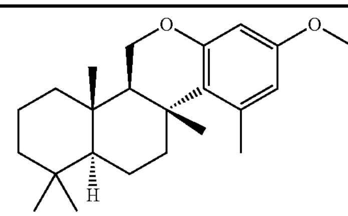 |
| 6 | 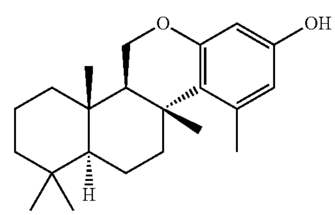 |
| 14 | 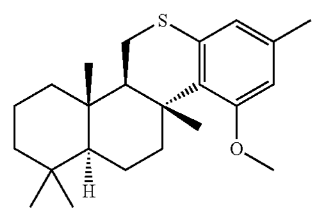 |
| 15 | 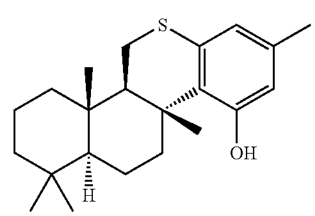 |

TABLE 1-continued

Representative Compounds

| Cd. No. | Structure |
|---|---|
| 16 | 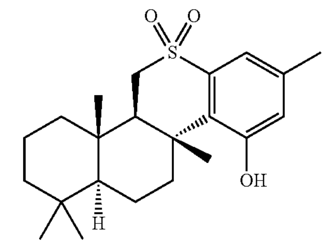 |
| 22 | 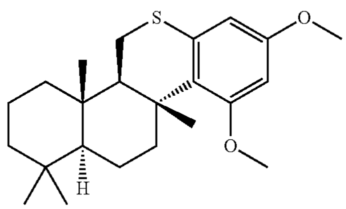 |
| 23 | 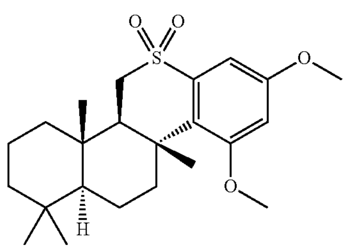 |
| 24 | 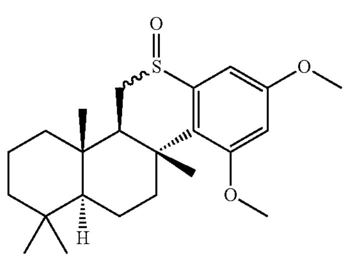 |
| 25 | 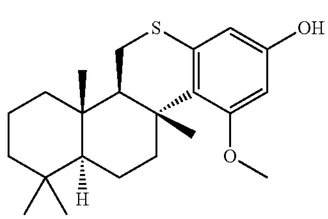 |
| 26 | 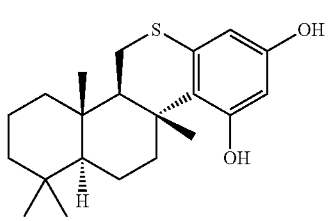 |
| 27 | |
| 28 | |
| 29 | |
| 30 | |
| 31 | |
| 32 | |

TABLE 1-continued
Representative Compounds
| Cd. No. | Structure |
|---|---|
| 33 | 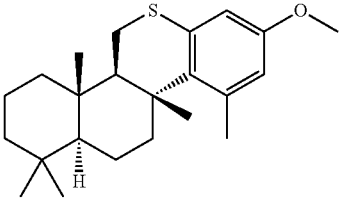 |
| 34 | 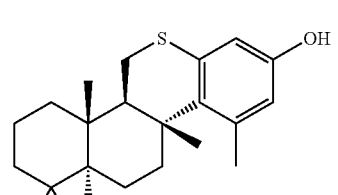 |
| 38 | 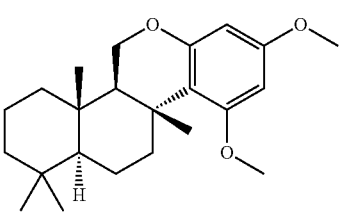 |
| 39 | 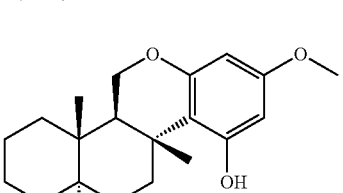 |
| 42 | 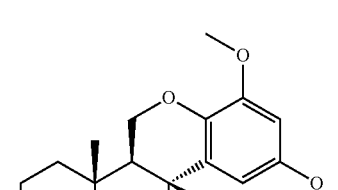 |
| 43 | 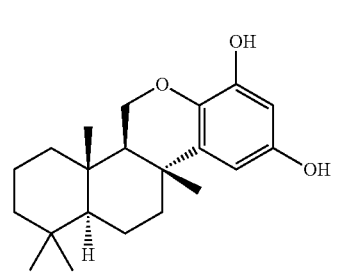 |
| 44 | 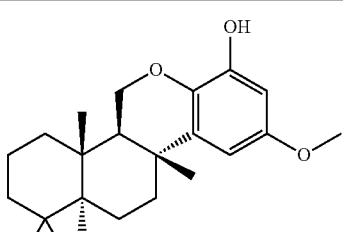 |
| 49 | 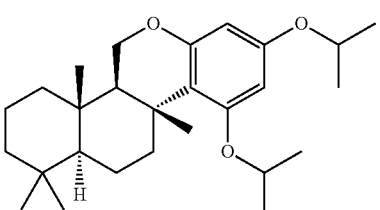 |
| 50 | 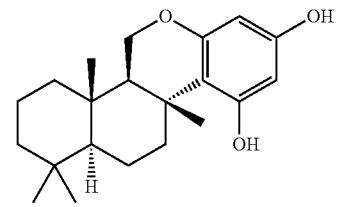 |
| 51 | 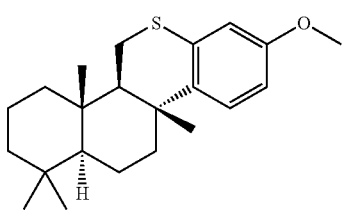 |
| 52 | 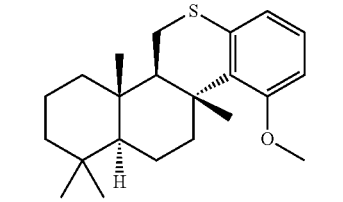 |
| 53 | 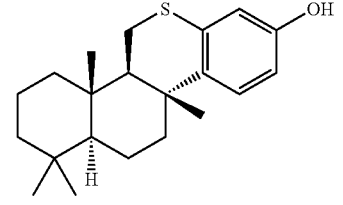 |

TABLE 1-continued

Representative Compounds

| Cd. No. | Structure |
|---|---|
| 54 | 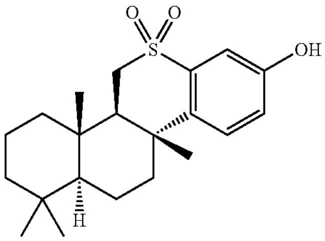 |
| 55 | 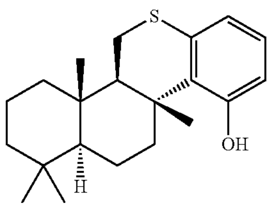 |
| 56 | 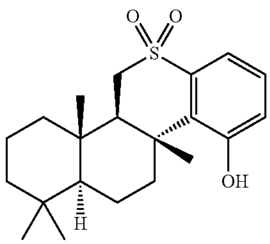 |
| 57 | 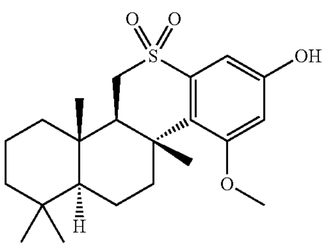 |
| 61 | 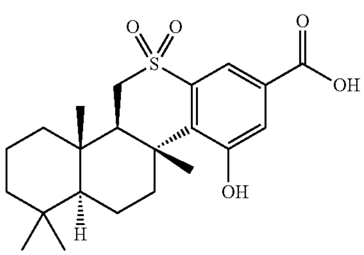 |
| 62 | 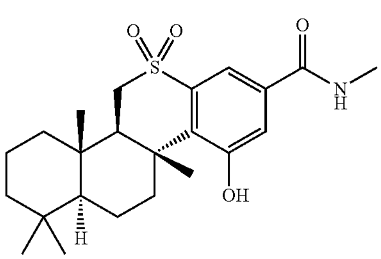 |
| 65 | |
| 66 | |
| 73 | |
| 76 | |
| 78 | |
| 79 | |

TABLE 1-continued

Representative Compounds

| Cd. No. | Structure |
|---|---|
| 80 | 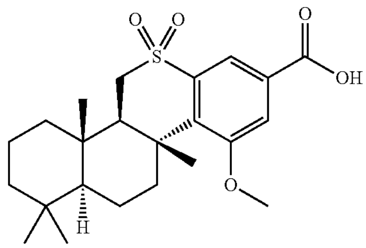 |
| 81 | 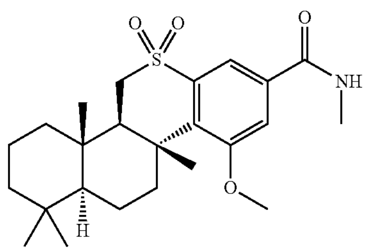 |
| 84 | 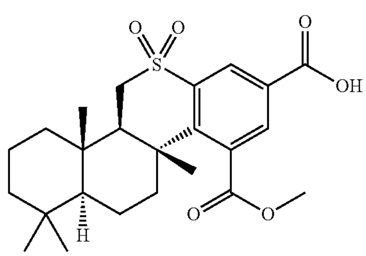 |
| 85 | 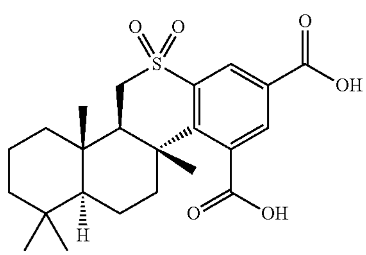 |
| 86 | 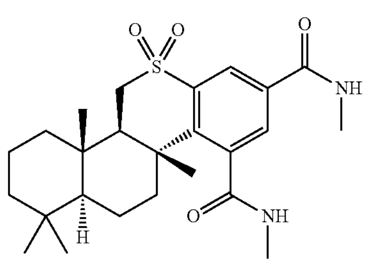 |
| 87 | |
| 88 | |
| 89 | |
| 91 | |

TABLE 1-continued

Representative Compounds

| Cd. No. | Structure |
|---|---|
| 92 | 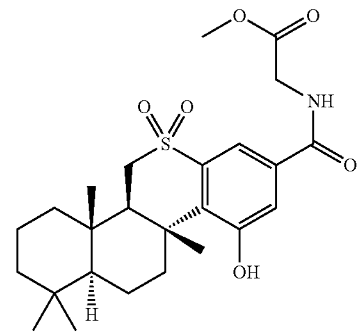 |
| 93 | 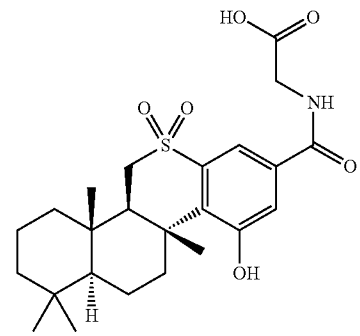 |
| 94 | 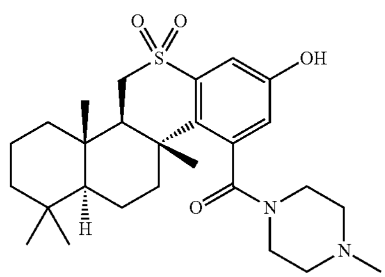 |
| 95 | 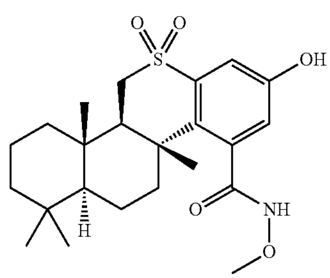 |
| 96 | 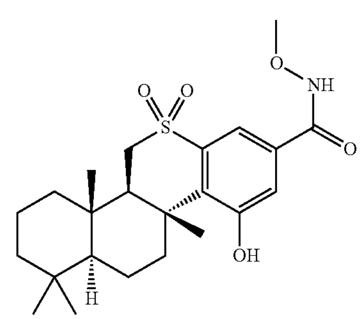 |
| 98 | |
| 100 | |
| 102 | |
| 104 | |

TABLE 1-continued

Representative Compounds

| Cd. No. | Structure |
|---|---|
| 105 | (structure) |
| 106 | (structure) |
| 108 | (structure) |
| 110 | (structure) |
| 112 | (structure) |

The effectiveness of a compound as a SHIP1 modulator may be determined by any number of known techniques, including the assay set forth in Example 56. As SHIP1 modulators, the compounds of this invention have utility over a wide range of therapeutic applications, and may be used to treat a variety of conditions in men and women, as well as mammals in general. For example, such conditions include autoimmune diseases such as idiopathic pulmonary fibrosis, Still's Disease, Sjögren's Syndrome, systemic lupus erythematosus, and systemic sclerosis; inflammatory diseases such as allergic rhinitis, Alzheimer's Disease, asthma, ocular inflammatory diseases (including allergic conjunctivitis, dry eye, and uveitis), chronic obstructive pulmonary disease, eczema, inflammatory bowel disease (including Crohn's Disease and ulcerative colitis), post operative inflammation, multiple sclerosis, psoriasis, seronegative spondyloarthropathies (including anklyosing spondylitis, psoriatic arthritis, and Reiter's Syndrome) rheumatoid arthritis, and vasculitis (including Wegener's Granulomatosis, polyarteritis nodosa, leucocytoclastic vasculitis, Churg-Strauss Syndrome, cryoglobulinemic vasculitis and giant cell arteritis); and neoplastic diseases or other cell proliferative disorders such as acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

For the purposes of administration, the compounds of the present invention may be formulated as pharmaceutical compositions. Pharmaceutical compositions comprise one or more compounds of this invention in combination with a pharmaceutically acceptable carrier and/or diluent. The compound is present in the composition in an amount which is effective to treat a particular disorder—that is, in an amount sufficient to achieve SHIP1 modulation activity, and preferably with acceptable toxicity to the patient. Typically, the pharmaceutical compositions of the present invention may include a compound in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for modulation of SHIP1 generally and, more specifically, to treating the conditions as discussed above. Such methods include administering of a compound of the present invention to a warm-blooded animal in an amount sufficient to treat the condition. In this context, "treat" includes prophylactic administration. Such methods include systemic administration of a compound of this invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

The following examples are provided for purposes of illustration, not limitation.

Example 1

Synthesis of (1R,10R,11S,16S)-5-methoxy-1,3,11,15,15-pentamethyl-8-oxatetracyclo[8.8.0.0$^{2,7}$.0$^{11,16}$]octadeca-2,4,6-triene

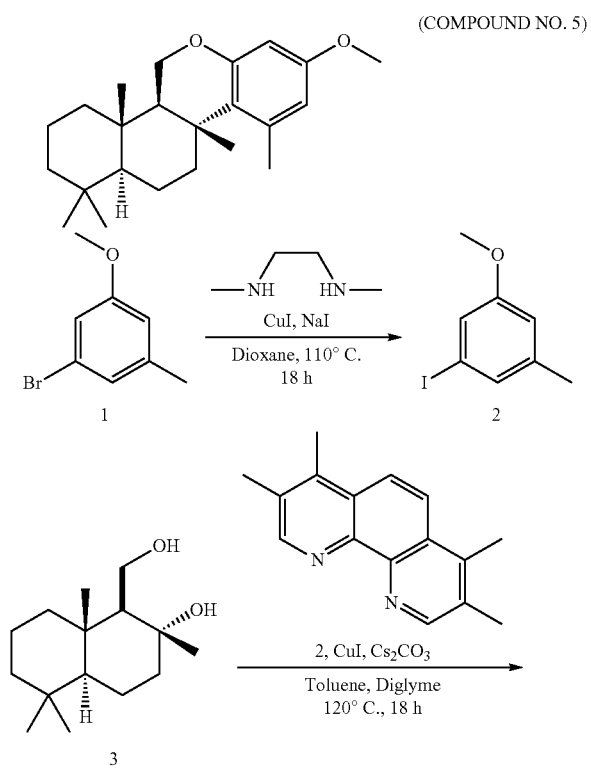

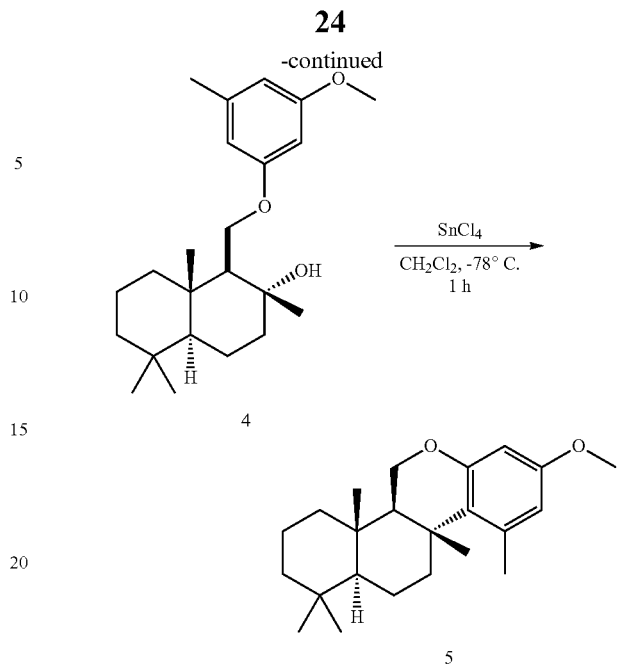

Cu(I)I (0.05 g, 0.25 mmol) and NaI (1.49 g, 10 mmol) were added to an oven dried sealed tube and the tube sealed with a rubber septum and flushed with a stream of nitrogen for 15 min. Anhydrous dioxane (5 mL), N,N'-dimethyl ethylenediamine (0.055 mL, 0.50 mmol) and 1-bromo-3-methoxy-5-methylbenzene (1) (1.0 g, 5.0 mmol) were added via a syringe with vigorous stirring under a stream of nitrogen at room temperature. The rubber septum was replaced with the Teflon cap and the sealed tube was heated at 110° C. in an oil bath for 18 h. The reaction was allowed to cool to room temperature and then quenched with a saturated aqueous solution of ammonium chloride. The reaction mixture was extracted with CH$_2$Cl$_2$. The organic layer was washed with water, and then concentrated to dryness to give 1-iodo-3-methoxy-5-methylbenzene (2) (1.05 g, 87% yield) as a pale yellow oil.

(1S,2R,4aS,8aS)-1-(hydroxymethyl)-2,5,5,8a-tetramethyl-decahydronaphthalen-2-ol (3) (prepared according to Kuchkova et al., *Synthesis*, 1045-1048, 1997) (0.24 g, 1.0 mmol), Cu(I)I (0.019 g, 0.10 mmol)) and 3,4,7,8-tetramethyl-[1,10]phenanthroline (0.047 g, 0.20 mmol)) were added to an oven dried sealed tube, sealed with a rubber septum, and flushed with a stream of nitrogen for 15 min. Anhydrous toluene (5 mL), anhydrous diglyme (1 mL) and 1-iodo-3-methoxy-5-methylbenzene (2) (0.273 g, 1.10 mmol) were added via a syringe with vigorous stirring under a stream of nitrogen at room temperature. The rubber septum was replaced with the Teflon cap and the sealed tube was heated at 120° C. in an oil bath for 18 h. The reaction was allowed to cool to room temperature, and then quenched with ethyl acetate. The resulting suspension was filtered through a celite pad. The filtrate and the washings were concentrated to dryness. The crude product was purified by flash chromatography (Hexanes/EtOAc, 9:1) to yield (1S,2R,4aS,8aS)-1-(3-methoxy-5-methylphenoxymethyl)-2,5,5,8a-tetramethyl-decahydronaphthalen-2-ol (4) (0.33 g, 92% yield) as a pale yellow solid.

A solution of (1S,2R,4aS,8aS)-1-(3-methoxy-5-methylphenoxymethyl)-2,5,5,8a-tetramethyl-decahydronaphthalen-2-ol (4) (0.335 g, 0.929 mmol) in CH$_2$Cl$_2$ (33 mL) was cooled in a dry ice-acetone bath. A 1 M solution of SnCl$_4$ in CH$_2$Cl$_2$ (1.84 mL, 1.84 mmol) was added dropwise to the previous solution while stirring under nitrogen. As soon as the addition ended, the reaction mixture was allowed to stir at −78° C. for 1 h. The reaction mixture was quenched with ice-water. The organic layer was separated and washed with saturated aqueous solution of sodium bicarbonate and then concentrated to dryness. The crude product was purified by flash chromatography (Hexanes/EtOAc, 98:2) to yield (1R,10R,11S,16S)-5-methoxy-1,3,11,15,15-pentamethyl-8-oxatetracyclo[8.8.0.0$^{2,7}$.0$^{11,16}$]octadeca-2,4,6-triene (Compound No. 5) (0.11 g, 35% yield) as an oil. $^1$H NMR (CDCl$_3$): δ 6.20 (m, 2H), 4.36 (m, 1H), 4.18 (m, 1H), 3.80 (s, 3H), 2.80 (m, 1H), 2.40 (s, 3H), 1.42-1.80 (m, 7H), 1.40 (s, 3H), 1.02-1.30 (m, 3H), 0.92 (m, 4H), 0.84 (s, 3H), 0.84 (s, 3H). MS m/z 343 (C$_{23}$H$_{34}$O$_2$+H$^+$).

Example 2

Synthesis of (1R,10R,11S,16S)-1,3,11,15,15-pentamethyl-8-oxatetracyclo[8.8.0.0$^{2,7}$.0$^{11,16}$]octadeca-2,4,6-trien-5-ol 3H), 0.98-1.28 (m, 3H), 0.92 (s, 3H), 0.88 (s, 3H), 0.84 (s, 3H). MS m/z 329 (C$_{22}$H$_{32}$O$_2$+H$^+$).

Example 3

Synthesis of (1R,10R,11S,16S)-3-methoxy-1,5,11,15,15-pentamethyl-8-thiatetracyclo[8.8.0.0$^{2,7}$.0$^{11,16}$]octadeca-2,4,6-triene

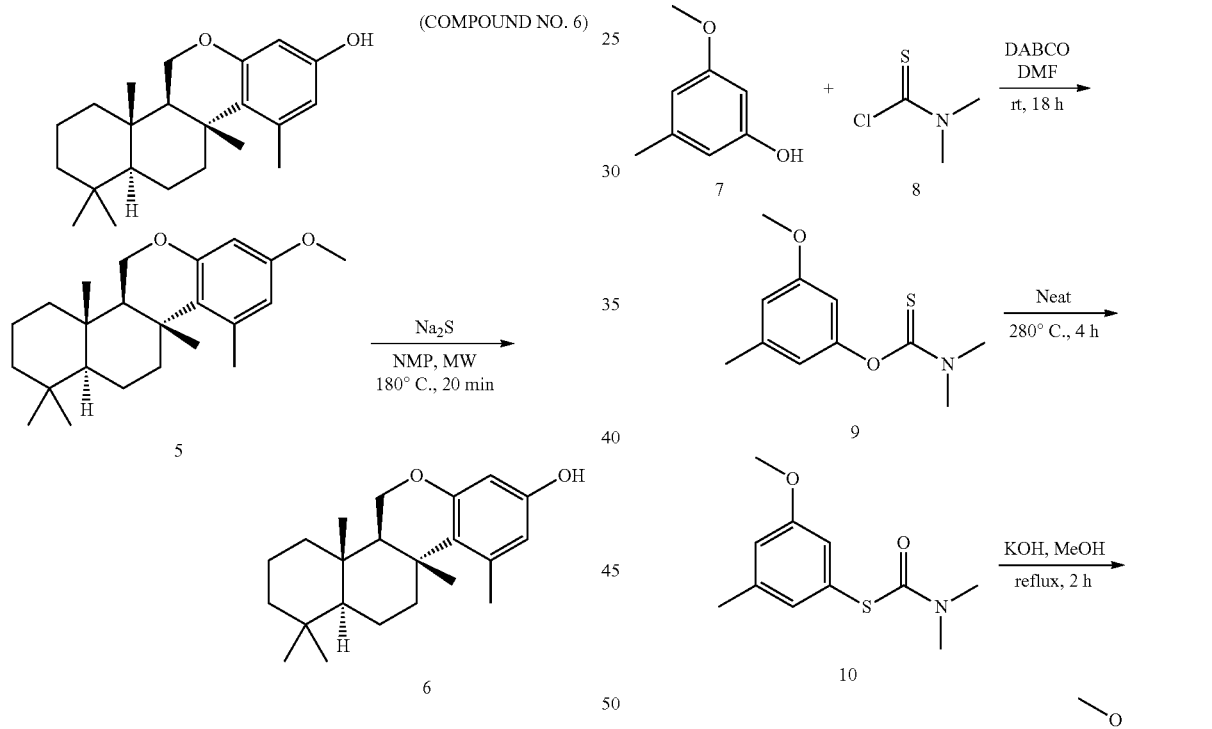

Sodium sulfide (0.14 g, 1.17 mmol) was added to a solution of (1R,10R,11S,16S)-5-methoxy-1,3,11,15,15-pentamethyl-8-oxatetracyclo[8.8.0.0$^{2,7}$.0$^{11,16}$]octadeca-2,4,6-triene (Compound No. 5) (0.08 g, 0.2 mmol) in anhydrous NMP (1.6 mL) in a microwave vessel. The reaction vessel was sealed and placed in a CEM-Discovery reactor and irradiated at 180° C. for 20 min. The reaction mixture was allowed to cool to room temperature and then quenched with 2 M HCl and ethyl acetate. The organic layer was separated, washed with water and concentrated to dryness. The crude product was purified by flash chromatography (Hexanes/EtOAc, 9:1) to yield (1R,10R,11S,16S)-1,3,11,15,15-pentamethyl-8-oxatetracyclo[8.8.0.0$^{2,7}$.0$^{11,16}$]octadeca-2,4,6-trien-5-ol (Compound No. 6) (0.022 g, 29% yield) as a white solid. $^1$H NMR (CDCl$_3$): δ 6.08 (m, 2H), 4.43 (s, 1H), 4.30 (m, 1H), 4.08 (m, 1H), 2.80 (m, 1H), 2.40 (s, 3H), 1.40-1.78 (m, 8H), 1.36 (s,

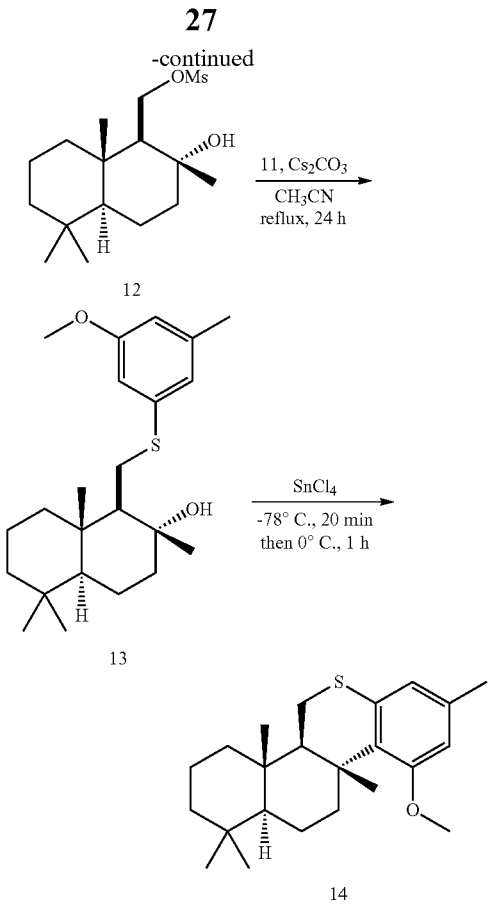

give ((1S,2R,4aS,8aS)-2-hydroxy-2,5,5,8a-tetramethyl-decahydronaphthalen-1-yl)methyl methanesulfonate (12) (5.90 g, 96%) as a light yellow sticky mass.

A mixture of 3-methoxy-5-methylbenzenethiol (11) (3.14 g, 20.4 mmol), ((1S,2R,4aS,8aS)-2-hydroxy-2,5,5,8a-tetramethyldecahydronaphthalen-1-yl)methyl methanesulfonate (12) (6.48 g, 20.4 mmol), and $Cs_2CO_3$ (19.90 g, 61.08 mmol) in $CH_3CN$ (300 mL) was stirred at room temperature for 1 h, then refluxed for 24 h. After cooling, the mixture was concentrated. Purification by chromatography on silica gel (Hexanes/EtOAc, 4:1) gave (1R,2R,4aS,8aS)-1-{[(3-methoxy-5-methylphenyl)sulfanyl]methyl}-2,5,5,8a-tetramethyl-decahydronaphthalen-2-ol (13) (5.70 g, purity ~75%) as a yellow sticky mass.

To a solution of (1R,2R,4aS,8aS)-1-{[(3-methoxy-5-methylphenyl)-sulfanyl]methyl}-2,5,5,8a-tetramethyl-decahydronaphthalen-2-ol (13) (5.70 g, 15.1 mmol) in $CH_2Cl_2$ (300 mL) was added dropwise $SnCl_4$ (1 M in $CH_2Cl_2$, 60 mL, 60 mmol) at −78° C. over 20 min. After complete addition, the reaction mixture was allowed to warm to 0° C. for 1 h. Water (50 mL) was added at 0° C. The organic layer was separated, dried ($Na_2SO_4$), and concentrated. Trituration with EtOAc (60 mL) gave (1R,10R,11S,16S)-3-methoxy-1,5,11,15,15-pentamethyl-8-thiatetracyclo[8.8.0.0$^{2,7}$.0$^{11,16}$]octadeca-2,4,6-triene (Compound No. 14) (1.44 g, batch 1) as a white solid. The filtrate was recrystallized to afford an additional batch (1.56 g, total yield 55%) as white crystals. $^1$H NMR ($CDCl_3$): δ 6.52 (d, 1H), 6.38 (d, 1H), 3.78 (s, 3H), 3.30 (m, 1H), 2.84 (m, 1H), 2.76 (m, 1H), 2.20 (s, 3H), 1.84-1.40 (m, 8H), 1.38 (s, 3H), 1.34-1.00 (m, 3H), 0.95 (s, 3H), 0.86 (s, 3H), 0.86 (s, 3H). MS m/z 359 ($C_{23}H_{34}OS+H^+$).

To a mixture of 3-methoxy-5-methylphenol (7) (3.39 g, 24.5 mmol) and 1,4-diazabicyclo[2.2.2]octane (5.50 g, 49.0 mmol) in DMF (20 mL) was added dimethylthiocarbamoyl chloride (8) (6.06 g, 49.0 mmol) portionwise. The reaction mixture was stirred at room temperature overnight and 500 mL of ether was added. The organics were washed with water (150 mL), brine (2×50 mL), dried ($Na_2SO_4$), and concentrated. Purification by chromatography on silica gel (Hexanes/EtOAc, 4:1) gave O-3-methoxy-5-methylphenyl dimethylcarbamothioate (9) (5.05 g, 91%) as a colourless solid.

O-3-Methoxy-5-methylphenyl dimethylcarbamothioate (9) (5.0 g, 22 mmol) was vacuum-degassed (4 cycles, flask was backfilled with nitrogen) and heated to 280° C. for 4 h, then cooled to room temperature. Purification by chromatography on silica gel (Hexanes/EtOAc, 85:15) gave S-3-methoxy-5-methylphenyl dimethylcarbamothioate (10) (4.10 g, 82%) as a light yellow oil.

A mixture of S-3-methoxy-5-methylphenyl dimethylcarbamothioate (10) (4.10 g, 18.2 mmol) and KOH (6.0 g) in MeOH (200 mL) was refluxed for 2 h. After cooling, the mixture was concentrated and diluted with EtOAc (500 mL). The organics were washed with 1N HCl (50 mL), brine (2×50 mL), dried ($Na_2SO_4$), and concentrated to give 3-methoxy-5-methylbenzenethiol (11) (2.80 g, quant.) as a colourless oil.

To a mixture of (1S,2R,4aS,8aS)-1-(hydroxymethyl)-2,5,5,8a-tetramethyl-decahydronaphthalen-2-ol (3) (4.66 g, 19.4 mmol)) and $Et_3N$ (7.01 mL, 50.4 mmol)) in DMF (40 mL) was added methanesulfonyl chloride (2.66 g, 23.3 mmol) dropwise at 0° C. After stirring at room temperature for 3 h, ether (400 mL) was added. The organics were washed with 1N HCl (20 mL), saturated aqueous sodium bicarbonate (20 mL), brine (2×20 mL), dried ($Na_2SO_4$), and concentrated to Example 4

Synthesis of (1R,10R,11S,16S)-1,5,11,15,15-pentamethyl-8-thiatetracyclo[8.8.0.0$^{2,7}$.0$^{11,16}$]octadeca-2,4,6-trien-3-ol

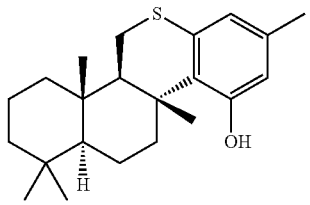

(COMPOUND NO. 15)

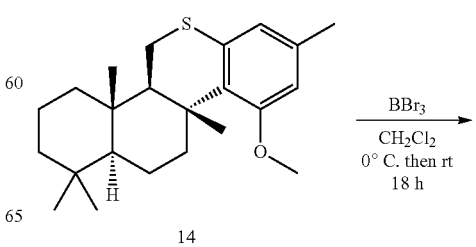

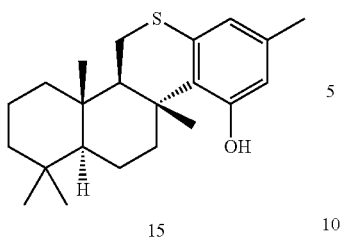

15

To a solution of (1R,10R,11S,16S)-3-methoxy-1,5,11,15,15-pentamethyl-8-thiatetracyclo[8.8.0.0$^{2,7}$.0$^{11,16}$]octadeca-2,4,6-triene (Compound No. 14) (1.16 g, 3.23 mmol) in CH$_2$Cl$_2$ (100 mL) was added BBr$_3$ (1.0 M in CH$_2$Cl$_2$, 9.70 mL, 9.70 mmol) dropwise at 0° C., and the resulting mixture stirred at room temperature overnight, then concentrated to dryness. Water (20 mL) was added at 0° C., followed by EtOAc (100 mL). The organic layer was separated, washed with brine (2×20 mL), dried (Na$_2$SO$_4$), and concentrated. Purification by chromatography on silica gel (Hexanes/EtOAc, 9:1) gave (1R,10R,11S,16S)-1,5,11,15,15-pentamethyl-8-thiatetracyclo[8.8.0.0$^{2,7}$.0$^{11,16}$]octadeca-2,4,6-trien-3-ol (Compound No. 15) (0.88 g, 79%) as a white solid. $^1$H NMR (CDCl$_3$): δ 6.50 (s, 1H), 6.15 (s, 1H), 4.60 (s, 1H), 3.38 (m, 1H), 2.90 (m, 1H), 2.78 (m, 1H), 2.18 (s, 3H), 1.84-1.42 (m, 9H), 1.40 (s, 3H), 1.20-1.00 (m, 2H), 0.98 (s, 3H), 0.89 (s, 3H), 0.89 (s, 3H). MS m/z 343 (C$_{22}$H$_{32}$OS–H$^+$).

Example 5

Synthesis of (1R,10R,11S,16S)-3-hydroxy-1,5,11,15,15-pentamethyl-8-thiatetracyclo[8.8.0.0$^{2,7}$.0$^{11,16}$]octadeca-2,4,6-triene-8,8-dione

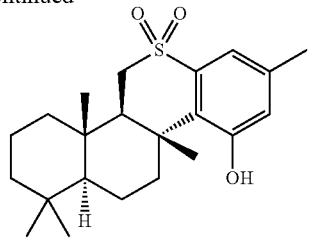

16

To a solution of (1R,10R,11S,16S)-1,5,11,15,15-pentamethyl-8-thiatetracyclo[8.8.0.0$^{2,7}$.0$^{11,16}$]octadeca-2,4,6-trien-3-ol (Compound No. 15) (100 mg, 0.29 mmol) in CH$_2$Cl$_2$ (20 mL) was added 3-chloroperoxybenzoic acid (77%, 130 mg, 0.58 mmol) portionwise at room temperature, and the resulting mixture stirred at room temperature for 2 h. CH$_2$Cl$_2$ (100 mL) was added and the mixture was washed with saturated aqueous sodium bicarbonate (20 mL), dried (Na$_2$SO$_4$), and concentrated. Purification by chromatography on silica gel (Hexanes/EtOAc, 3:1) gave (1R,10R,11S,16S)-3-hydroxy-1,5,11,15,15-pentamethyl-8-thiatetracyclo[8.8.0.0$^{2,7}$.0$^{11,16}$]octadeca-2,4,6-triene-8,8-dione (Compound No. 16) (70 mg, 64%) as a white solid. $^1$H NMR (CDCl$_3$): δ 7.30 (s, 1H), 6.61 (s, 1H), 5.16 (br s, 1H), 3.40-3.20 (m, 3H), 2.28 (s, 3H), 1.80-1.50 (m, 6H), 1.49 (s, 3H), 1.45-1.02 (m, 5H), 0.99 (s, 3H), 0.89 (s, 3H), 0.89 (s, 3H). MS m/z 375 (C$_{22}$H$_{32}$O$_3$S–H$^+$).

Example 6

Synthesis of (1R,10R,11S,16S)-3,5-dimethoxy-1,5,11,15,15-tetramethyl-8-thiatetracyclo[8.8.0.0$^{2,7}$.0$^{11,16}$]octadeca-2,4,6-triene (COMPOUND NO. 16)

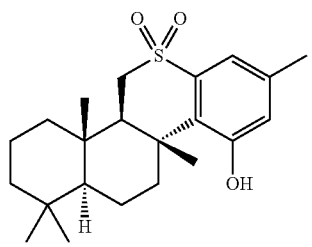

15 mCPBA
CH$_2$Cl$_2$
rt, 2 h (COMPOUND NO. 22)

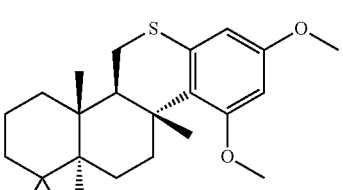

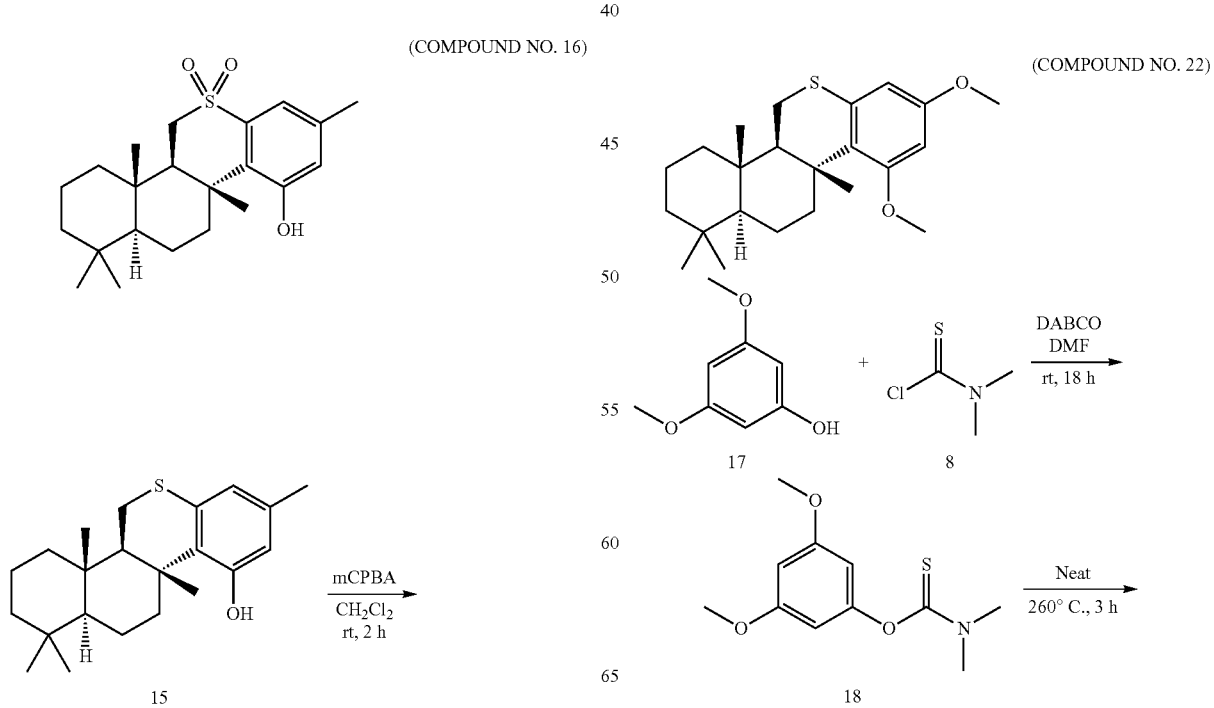

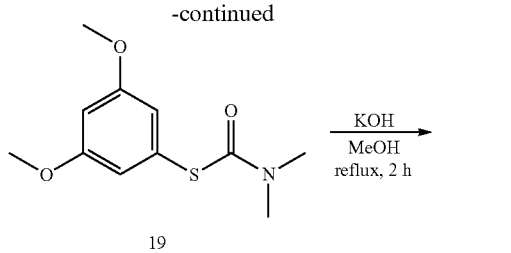

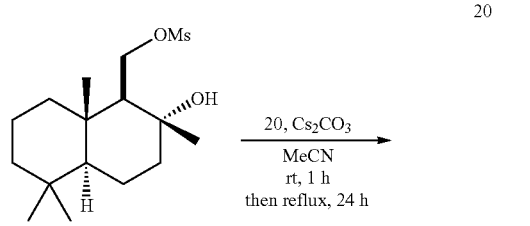

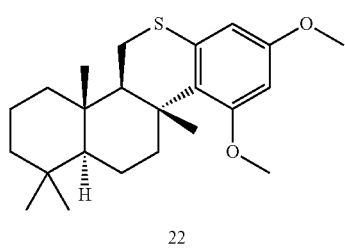

To a mixture of 3,5-dimethoxyphenol (17) (7.70 g, 50 mmol) and 1,4-diazabicyclo[2.2.2]octane (11.22 g, 100 mmol) in DMF (40 mL) was added dimethylthiocarbamoyl chloride (8) (12.36 g, 100 mmol) portionwise. The reaction mixture was stirred at room temperature overnight and 500 mL of ether was added. The organics were washed with water (150 mL), brine (2×50 mL), dried ($Na_2SO_4$), and concentrated. Purification by chromatography on silica gel (Hexanes/EtOAc, 4:1) gave O-3,5-dimethoxyphenyl dimethylcarbamothioate (18) (10.88 g, 90%) as a white solid.

O-3,5-Dimethoxyphenyl dimethylcarbamothioate (18) (1.0 g, 4.14 mmol) was vacuum-degassed (4 cycles, flask was backfilled with nitrogen) and heated to 260° C. for 3 h, then cooled to room temperature to give S-3,5-dimethoxyphenyl dimethylcarbamothioate (19) (1.0 g, quant.) as a light brown oil.

A mixture of S-3,5-dimethoxyphenyl dimethylcarbamothioate (19) (1.0 g, 4.14 mmol) and KOH (1.5 g) in MeOH (20 mL) was refluxed for 2 h. After cooling, it was concentrated. EtOAc (100 mL) was added. The organics were washed with 1N HCl (20 mL), brine (3×20 mL), dried ($Na_2SO_4$), and concentrated to give 3,5-dimethoxybenzenethiol (20) (0.70 g, quant.) as a light brown oil.

A mixture of 3,5-dimethoxybenzenethiol (20) (6.74 g, 39.60 mmol), ((1S,2R,4aS,8aS)-2-hydroxy-2,5,5,8a-tetramethyldecahydronaphthalen-1-yl)methyl methanesulfonate (12) (12.62 g, 39.60 mmol), and $Cs_2CO_3$ (38.70 g, 118.77 mmol) in $CH_3CN$ (560 mL) was stirred at room temperature for 1 h, then refluxed for 24 h. After cooling, the mixture was concentrated. Purification by chromatography on silica gel (Hexanes/EtOAc, 4:1) gave (1R,2R,4aS,8aS)-1-{[(3,5-dimethoxyphenyl)-sulfanyl]methyl}-2,5,5,8a-tetramethyl-decahydronaphthalen-2-ol (21) (9.40 g, 60%) as a light yellow sticky mass.

To a solution of (1R,2R,4aS,8aS)-1-{[(3,5-dimethoxyphenyl)sulfanyl]-methyl}-2,5,5,8a-tetramethyl-decahydronaphthalen-2-ol (21) (1.0 g, 2.55 mmol) in $CH_2Cl_2$ (50 mL) was added dropwise $SnCl_4$ (1 M in $CH_2Cl_2$, 10.2 mL, 10.19 mmol) at −78° C. over 5 min. After complete addition, the reaction mixture was allowed to warm to 0° C. for 1 h, then room temperature for 2 h. Water (20 mL) was added at room temperature followed by $CH_2Cl_2$ (50 mL). The organic layer was separated, dried ($Na_2SO_4$), and concentrated. Trituration with MeOH gave (1R,10R,11S,16S)-3,5-dimethoxy-1,11,15,15-tetramethyl-8-thiatetracyclo[8.8.0.0$^{2,7}$.0$^{11,16}$]octadeca-2,4,6-triene (Compound No. 22) (0.77 g, 81%) as a white solid. $^1$H NMR (CDCl$_3$): δ 6.22 (d, 1H), 6.18 (d, 1H), 3.78 (s, 3H), 3.78 (s, 3H), 3.25 (m, 1H), 2.90 (m, 1H), 2.78 (m, 1H), 1.84-1.38 (m, 7H), 1.37 (s, 3H), 1.36-1.00 (m, 3H), 0.95 (s, 3H), 0.90 (m, 1H), 0.85 (s, 3H), 0.85 (s, 3H). MS m/z 375 ($C_{23}H_{34}O_2S$+H$^+$).

Example 7

Synthesis of (1R,10R,11S,16S)-3,5-dimethoxy-1,11,15,15-tetramethyl-8-thiatetracyclo[8.8.0.0$^{2,7}$.0$^{11,16}$]octadeca-2,4,6-triene-8,8-dione

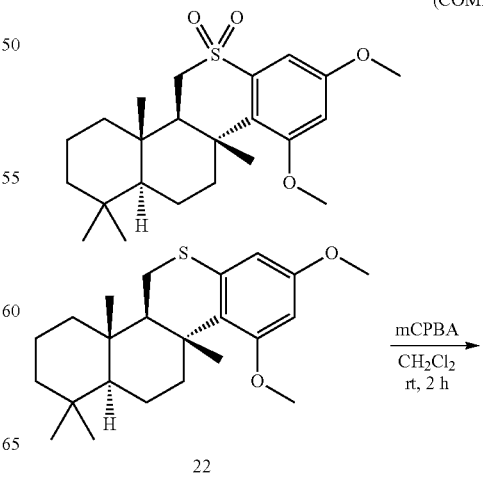

-continued

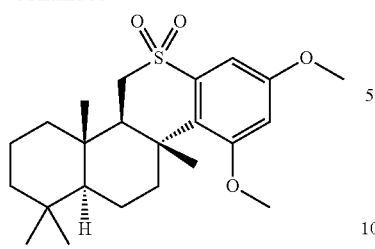

23

To a solution of (1R,10R,11S,16S)-3,5-dimethoxy-1,11,15,15-tetramethyl-8-thiatetracyclo[8.8.0.0$^{2,7}$.0$^{11,16}$]octadeca-2,4,6-triene (Compound No. 22) (374 mg, 1.0 mmol) in CH$_2$Cl$_2$ (20 mL) was added 3-chloroperoxybenzoic acid (77%, 448 mg, 2.0 mmol) portionwise at room temperature, and the resulting mixture was stirred at room temperature for 2 h. CH$_2$Cl$_2$ (100 mL) was added. The mixture was washed with saturated aqueous sodium bicarbonate (20 mL), dried (Na$_2$SO$_4$), and concentrated. Recrystallization from MeOH/CH$_2$Cl$_2$ gave (1R,10R,11S,16S)-3,5-dimethoxy-1,11,15,15-tetramethyl-8-thiatetracyclo[8.8.0.0$^{2,7}$.0$^{11,16}$]octadeca-2,4,6-triene-8,8-dione (Compound No. 23) (350 mg, 86%) as white needles. $^1$H NMR (CDCl$_3$): δ 6.95 (d, 1H), 6.58 (d, 1H), 3.84 (s, 3H), 3.81 (s, 3H), 3.39-3.17 (m, 3H), 2.30 (d, 1H), 1.78-1.42 (m, 6H), 1.41 (s, 3H), 1.40-1.00 (m, 4H), 0.99 (s, 3H), 0.85 (s, 3H), 0.84 (s, 3H). MS m/z 407 (C$_{23}$H$_{34}$O$_4$S+H$^+$).

Example 8

Synthesis of (1R,10R,11S,16S)-3,5-dimethoxy-1,11,15,15-tetramethyl-8-thiatetracyclo[8.8.0.0$^{2,7}$.0$^{11,16}$]octadeca-2,4,6-trien-8-one

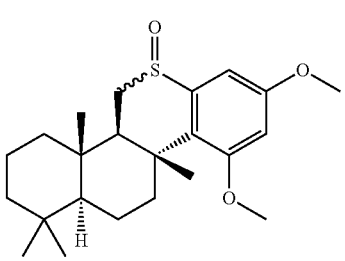

(COMPOUND NO. 24)

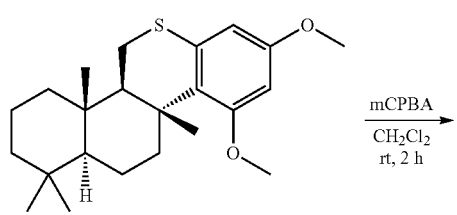

22

-continued

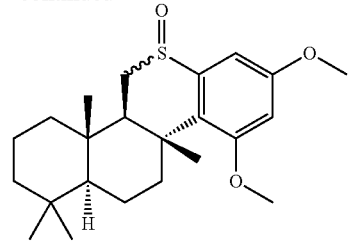

24
2 isolated diastereomers

To a solution of (1R,10R,11S,16S)-3,5-dimethoxy-1,11,15,15-tetramethyl-8-thiatetracyclo[8.8.0.0$^{2,7}$.0$^{11,16}$]octadeca-2,4,6-triene (Compound No. 22) (187 mg, 0.5 mmol) in CH$_2$Cl$_2$ (20 mL) was added 3-chloroperoxybenzoic acid (77%, 112 mg, 0.5 mmol) portionwise at room temperature. The resulting mixture was stirred at room temperature for 2 h. CH$_2$Cl$_2$ (100 mL) was added and the mixture washed with saturated aqueous sodium bicarbonate (20 mL), dried (Na$_2$SO$_4$), and concentrated. Purification by chromatography on silica gel (Hexanes/EtOAc, 1:1) gave (1R,10R,11S,16S)-3,5-dimethoxy-1,11,15,15-tetramethyl-8-thiatetracyclo[8.8.0.0$^{2,7}$.0$^{11,16}$]octadeca-2,4,6-trien-8-one (Compound No. 24) as separate diastereomers. (Diastereomer 1, white foam, 44 mg; Diastereomer 2, white solid, 290 mg).

Diastereomer 1: $^1$H NMR (CDCl$_3$): δ 6.98 (d, 1H), 6.45 (d, 1H), 3.82 (s, 3H), 3.80 (s, 3H), 3.39 (d, 1H), 3.07 (m, 1H), 2.88 (d, 1H), 1.82-1.45 (m, 6H), 1.42 (s, 3H), 1.41-1.10 (m, 3H), 1.00 (s, 3H), 0.95 (m, 2H), 0.85 (s, 3H), 0.85 (s, 3H). MS m/z 391 (C$_{23}$H$_{34}$O$_3$S+H$^+$).

Diastereomer 2: $^1$H NMR (CDCl$_3$): δ 6.82 (d, 1H), 6.58 (d, 1H), 3.82 (s, 3H), 3.80 (s, 3H), 3.10 (d, 1H), 2.79 (m, 1H), 2.40 (d, 1H), 1.78-1.38 (m, 9H), 1.37 (s, 3H), 1.14-1.10 (m, 2H), 1.00 (s, 3H), 0.85 (s, 3H), 0.85 (s, 3H). MS m/z 391 (C$_{23}$H$_{34}$O$_3$S+H$^+$).

Example 9

Synthesis of (1R,10R,11S,16S)-3-methoxy-1,11,15,15-tetramethyl-8-thiatetracyclo[8.8.0.0$^{2,7}$.0$^{11,16}$]octadeca-2,4,6-trien-5-ol

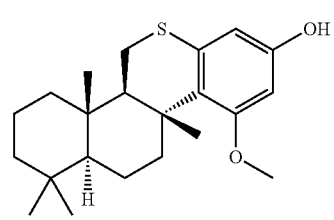

(COMPOUND NO. 25)

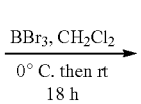

22

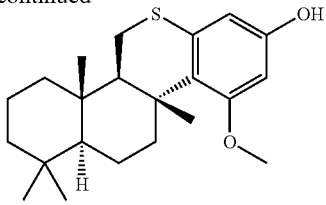

To a solution of (1R,10R,11S,16S)-3,5-dimethoxy-1,11,15,15-tetramethyl-8-thiatetracyclo[8.8.0.0$^{2,7}$.0$^{11,16}$]octadeca-2,4,6-triene (Compound No. 22) (375 mg, 1.0 mmol) in CH$_2$Cl$_2$ (50 mL) was added BBr$_3$ (1.0 M in CH$_2$Cl$_2$, 5.0 mL, 5.0 mmol) dropwise at 0° C., and the resulting mixture was stirred at room temperature overnight, then concentrated to dryness. Water (10 mL) was added at 0° C., followed by EtOAc (100 mL). The organic layer was separated, washed with brine (2×10 mL), dried (Na$_2$SO$_4$), and concentrated. Purification by chromatography on silica gel (Hexanes/EtOAc, 3:1) gave (1R,10R,11S,16S)-3-methoxy-1,11,15,15-tetramethyl-8-thiatetracyclo[8.8.0.0$^{2,7}$.0$^{11,16}$]octadeca-2,4,6-trien-5-ol (Compound No. 25) (120 mg, 33%) as a white foam. $^1$H NMR (CDCl$_3$): δ 6.15 (m, 2H), 4.46 (s, 1H), 3.78 (s, 3H), 3.25 (m, 1H), 2.90 (m, 1H), 2.76 (m, 1H), 1.84-1.32 (m, 6H), 1.30 (s, 3H), 1.29-1.00 (m, 4H), 0.95 (s, 3H), 0.94 (m, 1H), 0.85 (s, 3H), 0.85 (s, 3H). MS m/z 361 (C$_{22}$H$_{32}$O$_2$S+H$^+$).

Example 10

Synthesis of (1R,10R,11S,16S)-1,11,15,15-tetramethyl-8-thiatetracyclo[8.8.0.0$^{2,7}$.0$^{11,16}$]octadeca-2,4,6-triene-3,5-diol (COMPOUND NO. 26)

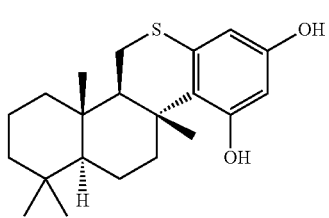

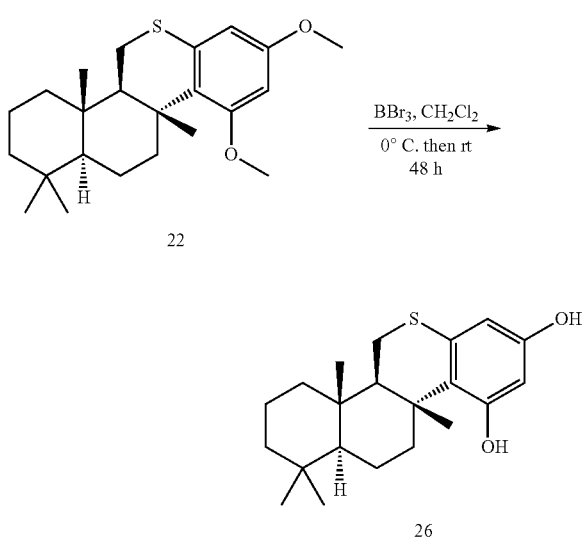

To a solution of (1R,10R,11S,16S)-3,5-dimethoxy-1,11,15,15-tetramethyl-8-thiatetracyclo[8.8.0.0$^{2,7}$.0$^{11,16}$]octadeca-2,4,6-triene (Compound No. 22) (3.75 g, 10 mmol) in CH$_2$Cl$_2$ (200 mL) was added BBr$_3$ (1.0 M in CH$_2$Cl$_2$, 60 mL, 60 mmol) dropwise at 0° C., and the resulting mixture was stirred at room temperature for 48 h, then concentrated to dryness. Water (100 mL) was added at 0° C., followed by EtOAc (500 mL). The organic layer was separated, washed with brine (2×50 mL), dried (Na$_2$SO$_4$), and concentrated. Purification by chromatography on silica gel (Hexanes/EtOAc, 3:1) followed by dilution with MeOH, concentration and trituration with water gave (1R,10R,11S,16S)-1,11,15,15-tetramethyl-8-thiatetracyclo[8.8.0.0$^{2,7}$.0$^{11,16}$]octadeca-2,4,6-triene-3,5-diol (Compound No. 26) (620 mg, 18%) as an off-white solid. $^1$H NMR (CDCl$_3$): δ 6.18 (d, 1H), 5.90 (d, 1H), 4.70 (s, 1H), 4.42 (s, 1H), 3.30 (m, 1H), 2.90 (m, 1H), 2.76 (m, 1H), 1.84-1.40 (m, 8H), 1.39 (s, 3H), 1.20-1.00 (m, 2H), 0.96 (s, 3H), 0.95 (m, 1H), 0.85 (s, 3H), 0.85 (s, 3H). MS m/z 345 (C$_{21}$H$_{30}$O$_2$S–H$^+$).

Example 11

Synthesis of (1R,10R,11S,16S)-3,5-dihydroxy-1,11,15,15-tetramethyl-8-thiatetracyclo[8.8.0.0$^{2,7}$.0$^{11,16}$]octadeca-2,4,6-trien-8-one (COMPOUND NO. 27)

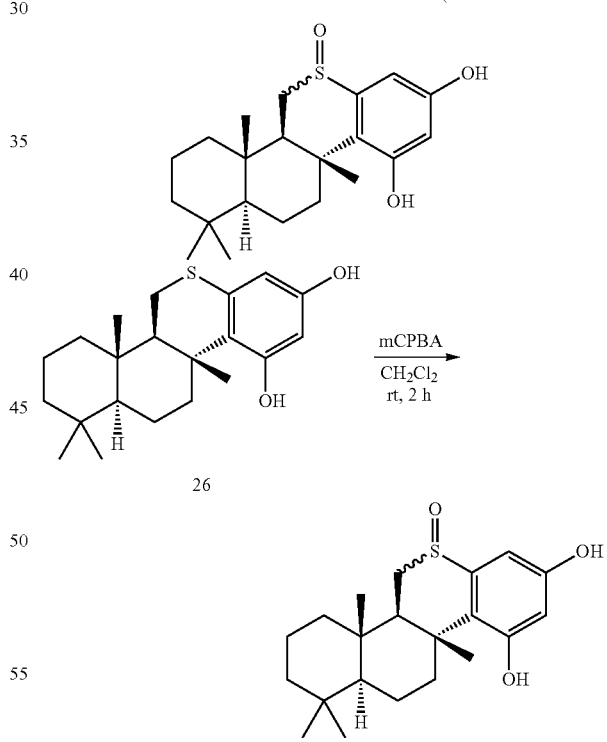

To a solution of (1R,10R,11S,16S)-1,11,15,15-tetramethyl-8-thiatetracyclo[8.8.0.0$^{2,7}$.0$^{11,16}$]octadeca-2,4,6-triene-3,5-diol (Compound No. 26) (346 mg, 1.0 mmol) in CH$_2$Cl$_2$ (20 mL) was added 3-chloroperoxybenzoic acid (77%, 225 mg, 1.0 mmol) portionwise at room temperature, and the resulting mixture was stirred at room temperature for 2 h. CH$_2$Cl$_2$ (100 mL) was added and the mixture washed with saturated aqueous sodium bicarbonate (20 mL), dried (Na$_2$SO$_4$), and concentrated. Purification by chromatography on silica gel (CH$_2$Cl$_2$/MeOH, 95:5) gave (1R,10R,11S,16S)-3,5-dihydroxy-1,11,15,15-tetramethyl-8-thiatetracyclo[8.8.0.0$^{2,7}$.0$^{11,16}$]octadeca-2,4,6-trien-8-one (Compound No. 27) (60 mg, 17%) as a white solid and inseparable mixture of diastereomers. $^1$H NMR (CD$_3$OD): δ 6.64-6.35 (4s, 2H), 3.50-2.34 (m, 3H), 1.90-0.90 (m, 11H), 1.50 and 1.40 (2s, 3H), 1.02 (2s, 3H), 0.92 (m, 6H). MS m/z 361 (O$_{21}$H$_{30}$O$_3$S—H$^+$).

Example 12

Synthesis of (1R,10R,11S,16S)-3,5-dihydroxy-1,11,15,15-tetramethyl-8-thiatetracyclo[8.8.0.0$^{2,7}$.0$^{11,16}$]octadeca-2,4,6-triene-8,8-dione

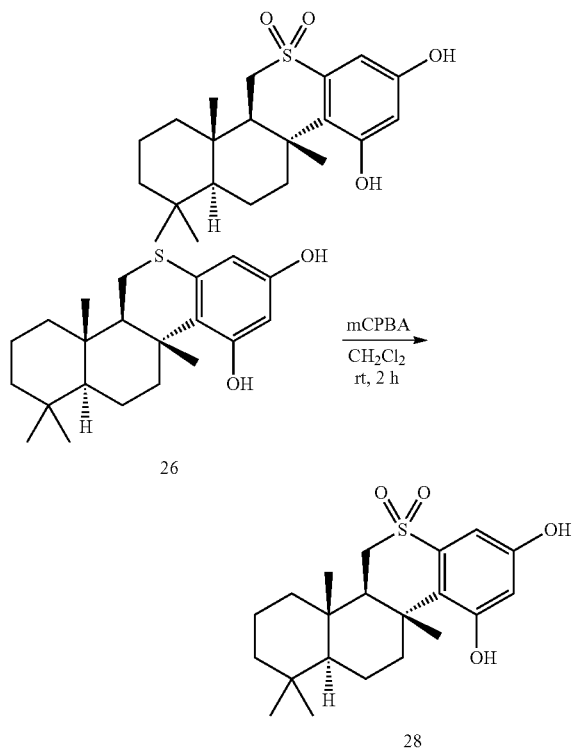

2H), 2.20 (dd, 1H), 1.80-1.50 (m, 6H), 1.44 (s, 3H), 1.42-1.02 (m, 4H), 1.00 (s, 3H), 0.91 (s, 3H), 0.89 (s, 3H). MS m/z 377 (C$_{21}$H$_{30}$O$_4$S–H$^+$).

Example 13

Synthesis of (1R,10R,11S,16S)-5-methoxy-1,11,15,15-tetramethyl-8-thiatetracyclo[8.8.0.0$^{2,7}$.0$^{11,16}$]octadeca-2,4,6-trien-3-ol

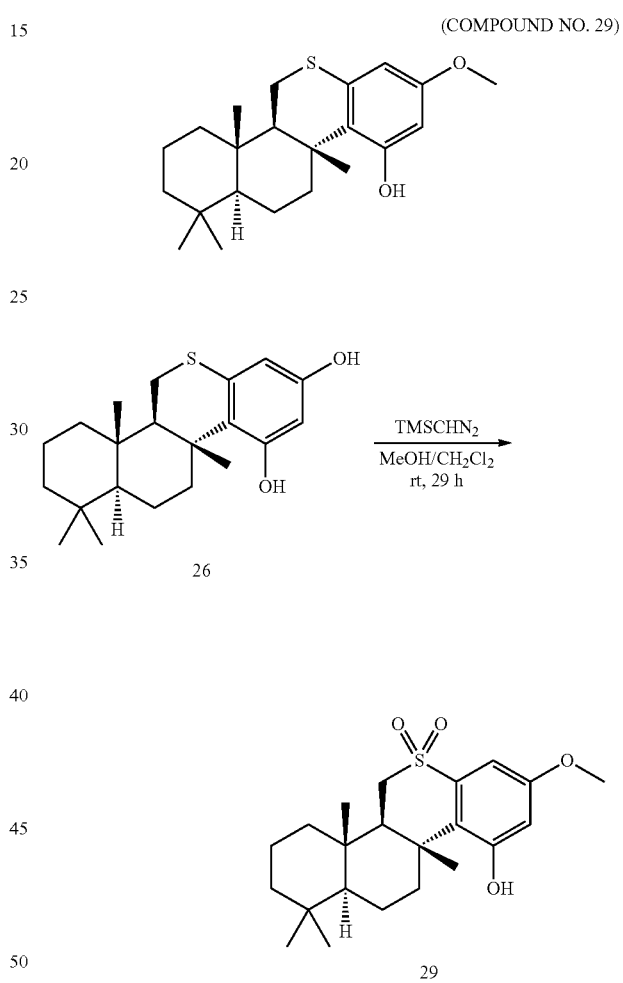

To a solution of (1R,10R,11S,16S)-1,11,15,15-tetramethyl-8-thiatetracyclo[8.8.0.0$^{2,7}$.0$^{11,16}$]octadeca-2,4,6-triene-3,5-diol (Compound No. 26) (173 mg, 0.5 mmol) in CH$_2$Cl$_2$ (20 mL) was added 3-chloroperoxybenzoic acid (77%, 225 mg, 1.0 mmol) portionwise at room temperature, and the resulting mixture was stirred at room temperature for 2 h. CH$_2$Cl$_2$ (100 mL) was added and the mixture washed with saturated aqueous sodium bicarbonate (20 mL), dried (Na$_2$SO$_4$), and concentrated. Purification by chromatography on silica gel (CH$_2$Cl$_2$/MeOH, 98:2) gave (1R,10R,11S,16S)-3,5-dihydroxy-1,11,15,15-tetramethyl-8-thiatetracyclo[8.8.0.0$^{2,7}$.0$^{11,16}$]octadeca-2,4,6-triene-8,8-dione (Compound No. 28) (120 mg, 64%) as white solid. $^1$H NMR (CD$_3$OD): δ 6.70 (d, 1H), 6.41 (d, 1H), 3.50 (m, 1H), 3.30 (m, (1R,10R,11S,16S)-1,11,15,15-Tetramethyl-8-thiatetracyclo[8.8.0.0$^{2,7}$.0$^{11,16}$]octadeca-2,4,6-triene-3,5-diol (Compound No. 26) (346 mg, 1.0 mmol) was dissolved in MeOH (4 mL) and CH$_2$Cl$_2$ (12 mL). Trimethylsilyl diazomethane (0.80 mL, 2.0 M in ether, 1.6 mmol) was added portionwise over 29 h at room temperature, monitoring the reaction by $^1$H NMR. The mixture was then concentrated and purified by chromatography on silica gel (Hexanes/EtOAc, 4:1) followed by recrystallization from MeOH/water to give (1R,10R,11S,16S)-5-methoxy-1,11,15,15-tetramethyl-8-thiatetracyclo[8.8.0.0$^{2,7}$.0$^{11,16}$]octadeca-2,4,6-trien-3-ol (Compound No. 29) (142 mg, 39%) as a white solid. $^1$H NMR (CDCl$_3$): δ 6.21 (d, 1H), 5.95 (d, 1H), 4.72 (s, 1H), 3.69 (s, 3H), 3.30 (m, 1H), 2.91 (m, 1H), 2.78 (m, 1H), 1.85-1.40 (m, 8H), 1.39 (s, 3H), 1.20-1.00 (m, 2H), 0.96 (s, 3H), 0.95 (m, 1H), 0.85 (s, 3H), 0.84 (s, 3H). MS m/z 359 ($C_{22}H_{32}O_2S-H^+$).

Example 14

Synthesis of (1R,10R,11S,16S)-3-hydroxy-5-methoxy-1,11,15,16-tetramethyl-8-thiatetracyclo[8.8.0.$0^{2,7}$.$0^{11,16}$]octadeca-2,4,6-triene-8,8-dione (COMPOUND NO. 30)

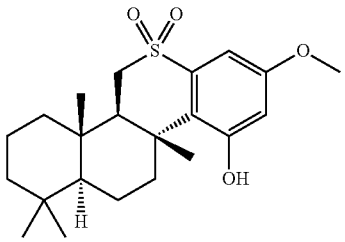

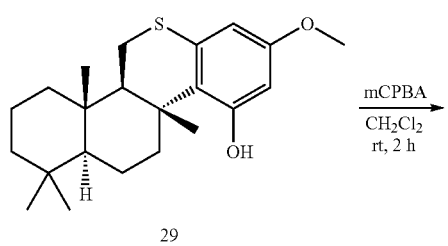

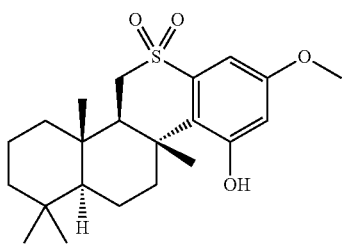

To a solution of (1R,10R,11S,16S)-5-methoxy-1,11,15,15-tetramethyl-8-thiatetracyclo[8.8.0.$0^{2,7}$.$0^{11,16}$]octadeca-2,4,6-trien-3-ol (Compound No. 29) (180 mg, 0.5 mmol) in $CH_2Cl_2$ (20 mL) was added 3-chloroperoxybenzoic acid (77%, 225 mg, 1.0 mmol) portionwise at room temperature, and the resulting mixture was stirred at room temperature for 2 h. $CH_2Cl_2$ (100 mL) was added and the mixture washed with saturated aqueous sodium bicarbonate (20 mL), dried ($Na_2SO_4$), and concentrated. Purification by chromatography on silica gel ($CH_2Cl_2$/MeOH, 98:2) gave (1R,10R,11S,16S)-3-hydroxy-5-methoxy-1,11,15,15-tetramethyl-8-thiatetracyclo[8.8.0.$0^{2,7}$.$0^{11,16}$]octadeca-2,4,6-triene-8,8-dione (Compound No. 30) (110 mg, 56%) as a light yellow solid. $^1$H NMR ($CDCl_3$): δ 6.99 (d, 1H), 6.40 (d, 1H), 5.20 (s, 1H), 3.80 (s, 3H), 3.35-3.15 (m, 3H), 2.30 (dd, 1H), 1.75-1.45 (m, 6H), 1.44 (s, 3H), 1.42-1.02 (m, 4H), 0.98 (s, 3H), 0.89 (s, 3H), 0.85 (s, 3H). MS m/z 391 ($C_{22}H_{32}O_4S-H^+$).

Example 15

Synthesis of (1R,10R,11S,16S)-3-hydroxy-5-methoxy-1,11,15,15-tetramethyl-8-thiatetracyclo[8.8.0.$0^{2,7}$.$0^{11,16}$]octadeca-2,4,6-trien-8-one (COMPOUND NO. 31)

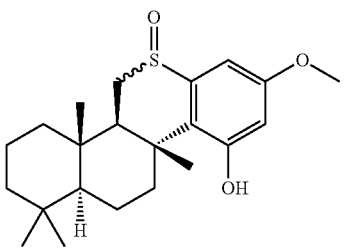

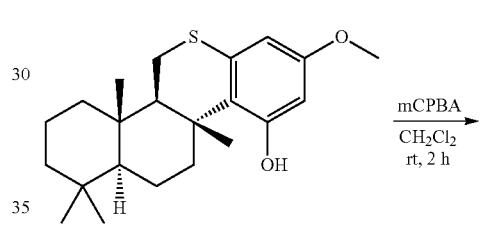

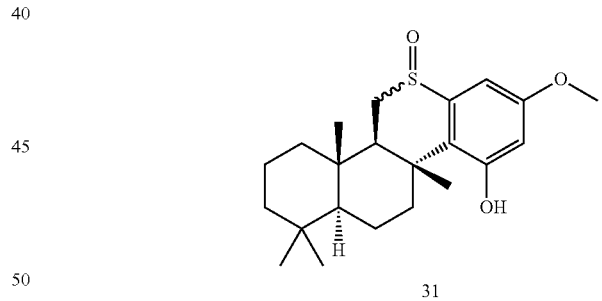

To a solution of (1R,10R,11S,16S)-5-methoxy-1,11,15,15-tetramethyl-8-thiatetracyclo[8.8.0.$0^{2,7}$.$0^{11,16}$]octadeca-2,4,6-trien-3-ol (Compound No. 29) (180 mg, 0.5 mmol) in $CH_2Cl_2$ (20 mL) was added 3-chloroperoxybenzoic acid (77%, 112 mg, 0.5 mmol) portionwise at room temperature, and the resulting mixture stirred at room temperature for 2 h. $CH_2Cl_2$ (100 mL) was added and the mixture washed with saturated aqueous sodium bicarbonate (20 mL), dried ($Na_2SO_4$), and concentrated. Purification by chromatography on silica gel ($CH_2Cl_2$/MeOH, 98:2) gave (1R,10R,11S,16S)-3-hydroxy-5-methoxy-1,11,15,15-tetramethyl-8-thiatetracyclo[8.8.0.$0^{2,7}$.$0^{11,16}$]octadeca-2,4,6-trien-8-one (Compound No. 31) (90 mg, 48%) as an off-white solid and inseparable mixture of diastereomers. $^1$H NMR ($CD_3OD$): δ 6.78-6.43

(4s, 2H), 3.78 (2s, 3H), 3.50-2.75 (m, 3H), 2.40-0.95 (m, 11H), 1.55 and 1.42 (2s, 3H), 1.02 (2s, 3H), 0.90 (m, 6H). MS m/z 375 ($C_{22}H_{32}O_3S-H^+$).

Example 16

Synthesis of (1R,10R,11S,16S)-5-methoxy-1,11,15,15-tetramethyl-8-thiatetracyclo[8.8.0.0$^{2,7}$.0$^{11,16}$]octadeca-2,4,6-trien-3-yl trifluoromethanesulfonate

Example 17

Synthesis of (1R,10R,11S,16S)-5-methoxy-1,3,11,15,15-pentamethyl-8-thiatetracyclo[8.8.0.0$^{2,7}$.0$^{11,16}$]octadeca-2,4,6-triene

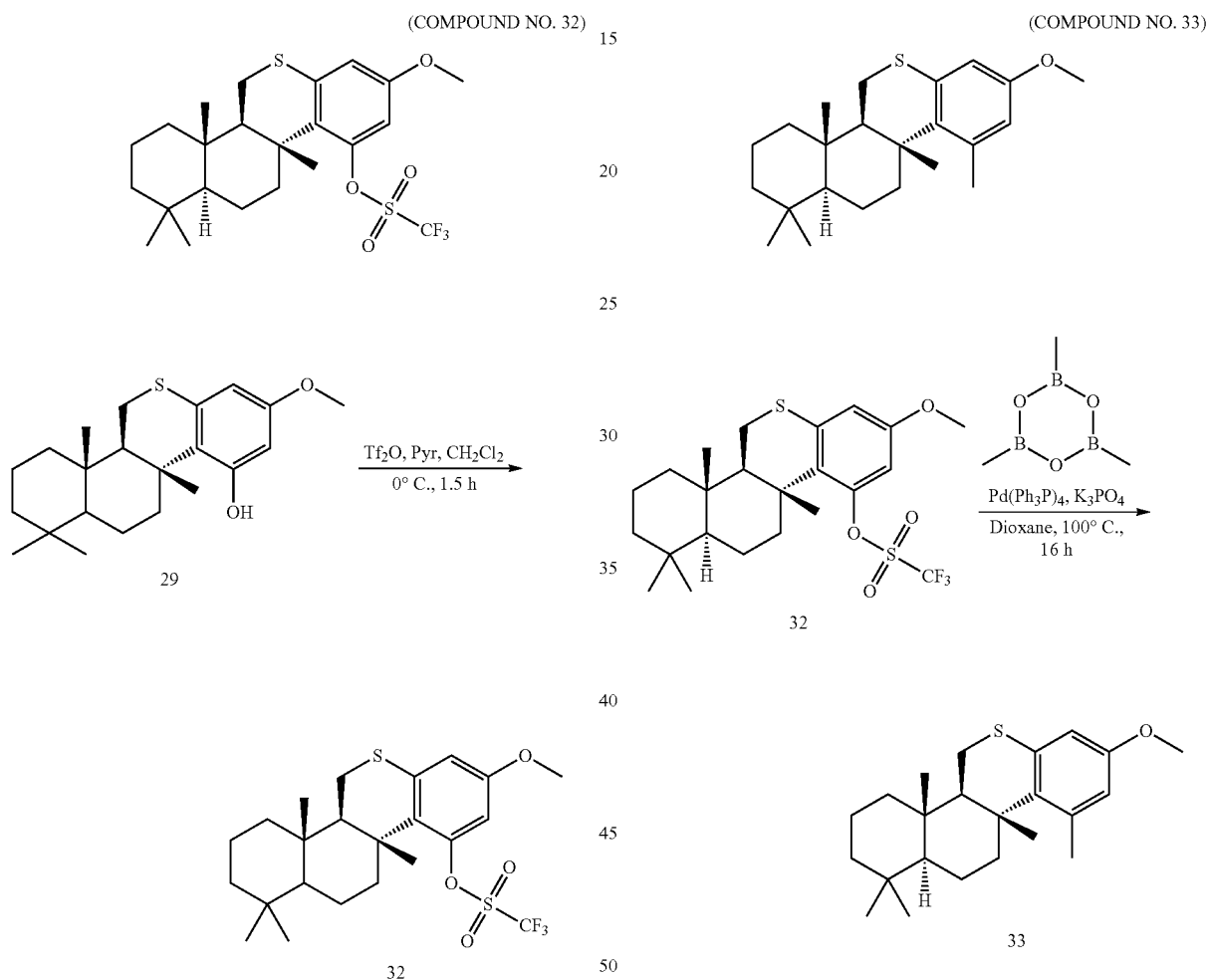

To a solution of (1R,10R,11S,16S)-5-methoxy-1,11,15,15-tetramethyl-8-thiatetracyclo[8.8.0.0$^{2,7}$.0$^{11,16}$]octadeca-2,4,6-trien-3-ol (Compound No. 29) (0.61 g, 1.69 mmol) in $CH_2Cl_2$ (40 mL), pyridine (0.20 g, 2.54 mmol) was added and the mixture was cooled to 0° C. $Tf_2O$ (0.62 g, 2.20 mmol) was added dropwise to the reaction mixture and stirred for 1.5 h. The reaction was diluted with $CH_2Cl_2$ and washed with water (2×40 mL). The organic layer was separated, dried ($Na_2SO_4$) and concentrated giving (1R,10R,11S,16S)-5-methoxy-1,11,15,15-tetramethyl-8-thiatetracyclo[8.8.0.0$^{2,7}$.0$^{11,16}$]octadeca-2,4,6-trien-3-yl trifluoromethanesulfonate (Compound No. 32) (0.825 g, 98%) as a yellow foam. $^1$H NMR (CDCl$_3$):

δ 6.58 (d, 2H), 3.75 (s, 3H), 2.90 (m, 3H), 1.80-1.40 (m, 8H), 1.38 (s, 3H), 1.25-1.00 (m, 2H), 0.95 (s, 3H), 0.90 (m, 1H), 0.85 (s, 3H), 0.80 (s, 3H).

In a sealed tube was placed (1R,10R,11S,16S)-5-methoxy-1,11,15,15-tetramethyl-8-thiatetracyclo[8.8.0.0$^{2,7}$.0$^{11,16}$]octadeca-2,4,6-trien-3-yl trifluoromethanesulfonate (Compound No. 32) (0.098 g, 0.20 mmol), trimethylboroxine (0.050 g, 0.40 mmol), $K_3PO_4$ (0.085 g, 0.40 mmol), Pd(Ph$_3$P)$_4$ (0.046 g, 0.04 mmol) and dioxane (4 mL). The vessel was degassed for 5 min, then sealed and stirred at 100° C. for 16 h. The reaction was cooled to room temperature, diluted with EtOAc and washed with brine. The organic layer was separated, dried ($Na_2SO_4$) and concentrated. Purification by column chromatography on silica gel (Hexanes/EtOAc, 95:5) gave (1R,10R,11S,16S)-5-methoxy-1,3,11,15,15-pentamethyl-8-thiatetracyclo[8.8.0.0$^{2,7}$.0$^{11,16}$]octadeca-2,4,6-triene (Compound No. 33) (0.060 g, 83%) as a white foam. $^1$H NMR (CDCl$_3$): δ 6.46 (m, 1H), 6.39 (m, 1H), 3.71 (s, 3H), 2.98-2.80 (m, 3H), 2.50 (s, 3H), 1.95-1.37 (m, 8H), 1.37 (s, 3H), 1.20-1.00 (m, 2H), 0.94 (s, 3H), 0.90 (m, 1H), 0.86 (s, 3H), 0.84 (s, 3H). MS m/z 359 ($C_{23}H_{34}OS+H^+$).

Example 18

Synthesis of (1R,10R,11S,16S)-1,3,11,15,15-pentamethyl-8-thiatetracyclo[8.8.0.0$^{2,7}$.0$^{11,16}$]octadeca-2,4,6-trien-5-ol

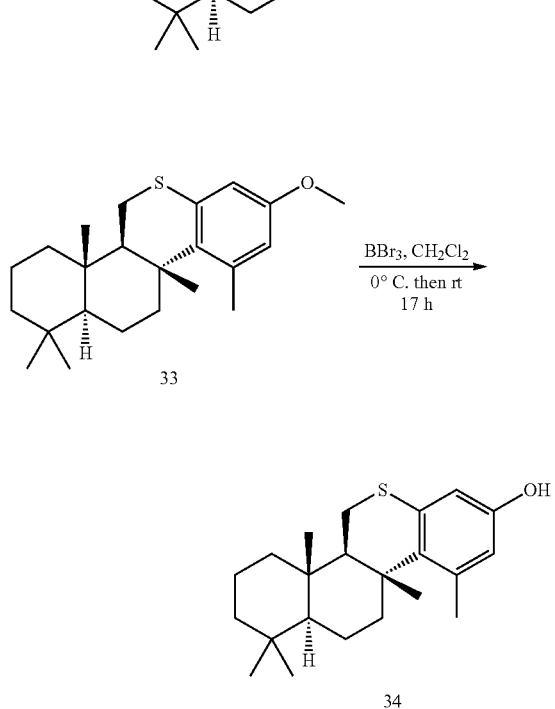

To a solution of (1R,10R,11S,16S)-5-methoxy-1,3,11,15,15-pentamethyl-8-thiatetracyclo[8.8.0.0$^{2,7}$.0$^{11,16}$]octadeca-2,4,6-triene (Compound No. 33) (0.22 g, 0.61 mmol) in anhydrous $CH_2Cl_2$ (20 mL) at 0° C. under nitrogen was added $BBr_3$ (1.0 M in $CH_2Cl_2$, 1.85 mL, 1.85 mmol) dropwise. The solution was stirred at room temperature for 17 h, quenched with anhydrous MeOH (12 mL) and evaporated. The residue was co-evaporated with MeOH (5×18 mL) and dried in vacuo. Purification by silica gel chromatography (Hexanes/EtOAc, 9:1) gave a product (0.130 g) with an approximate purity of 70% ($^1$H NMR). The material was further purified by preparative HPLC (column Gem 30×100 mm, mobile phase MeCN/0.1% HCOOH) to afford (1R,10R,11S,16S)-1,3,11,15,15-pentamethyl-8-thiatetracyclo[8.8.0.0$^{2,7}$.0$^{11,16}$]octadeca-2,4,6-trien-5-ol (Compound No. 34) (86 mg, 40%) as a white solid. $^1$H NMR (CDCl$_3$): δ 6.40 (d, 1H), 6.31 (d, 1H), 4.34 (s, 1H), 2.95-2.86 (m, 2H), 2.82-2.76 (m, 1H), 2.46 (s, 3H), 1.87-1.81 (m, 1H), 1.68-1.56 (m, 3H), 1.53-1.35 (m, 5H), 1.35 (s, 3H), 1.19-1.08 (m, 1H), 1.07-0.97 (m, 1H), 0.93 (s, 3H), 0.85 (s, 3H), 0.83 (s, 3H). MS m/z 345 ($C_{22}H_{32}O_4S+H^+$).

Example 19

Synthesis of (1R,10R,11S,16S)-3,5-dimethoxy-1,11,15,15-tetramethyl-8-oxatetracyclo[8.8.0.0$^{2,7}$.0$^{11,16}$]octadeca-2,4,6-triene

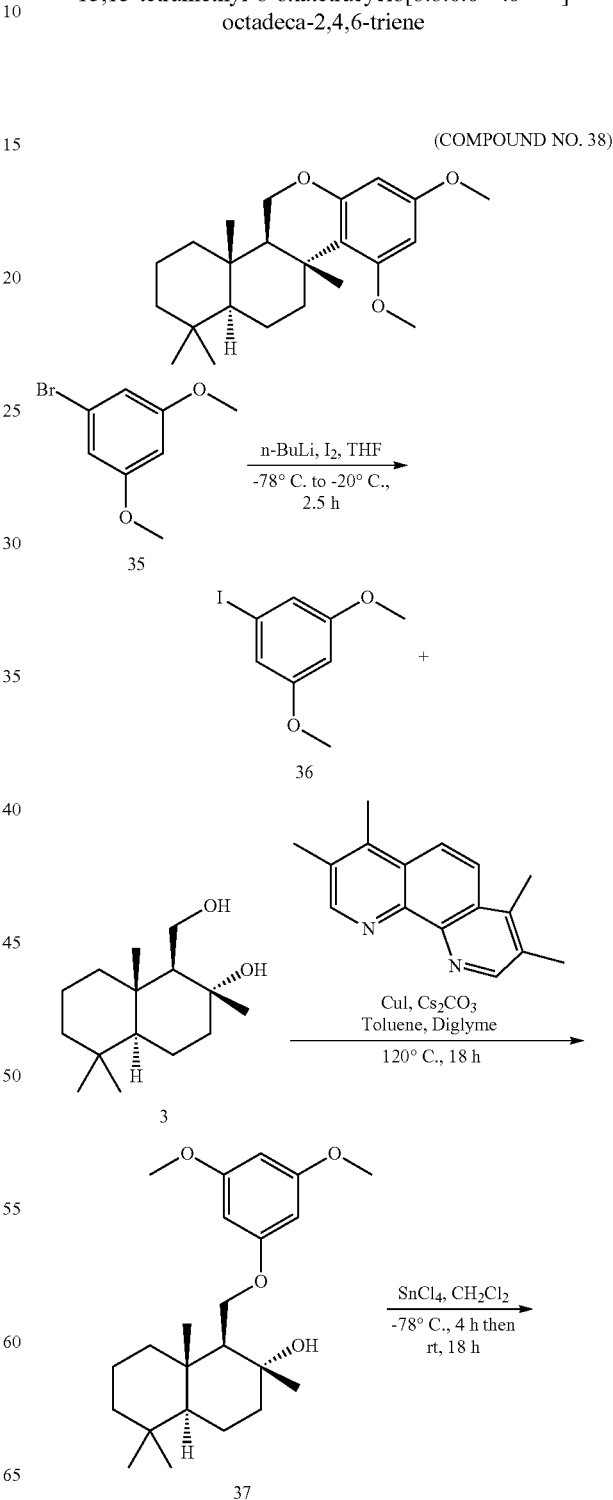

-continued

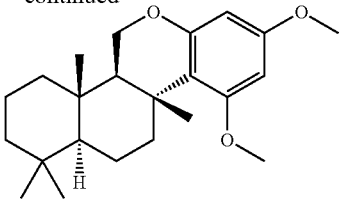
38

To a stirred solution of 1-bromo-3,5-dimethoxybenzene (35) (2.17 g, 10.0 mmol) in THF (50 mL), cooled to −78° C., and n-BuLi (12.5 mL, 1.6 M in hexane, 20.0 mmol) was added dropwise. The mixture was allowed to warm to −20° C. over 2.5 h. The reaction was diluted with EtOAc (300 mL) and washed with water (150 mL). The organic layer was separated, dried (Na$_2$SO$_4$) and concentrated. Purification by column chromatography on silica gel (Hexanes/EtOAc, 2:1) gave 1-iodo-3,5-dimethoxybenzene (36) (1.6 g, 60%) as a brown oil.

In a sealed tube purged with nitrogen, 1-iodo-3,5-dimethoxybenzene (36) (0.78 g, 3.0 mmol), (1S,2R,4aS,8aS)-1-(hydroxymethyl)-2,5,5,8a-tetramethyl-decahydronaphthalen-2-ol (3) (0.65 g, 2.68 mmol), Cs$_2$CO$_3$ (1.3 g, 4.0 mmol), 3,4,7,8-tetramethyl-[1,10]-phenylthroline (0.12 g, 0.50 mmol), CuI (0.05 g, 0.3 mmol), diglyme (2 mL) and toluene (10 mL) were added. The reaction mixture was stirred at 120° C. for 18 h. The reaction was cooled to room temperature, diluted with EtOAc (300 mL) and washed with water (100 mL). The organic layer was dried (Na$_2$SO$_4$) and concentrated. Purification by column chromatography on silica gel (Hexanes/EtOAc, 2:1) gave (1S,2R,4aS,8aS)-1-(3,5-dimethoxyphenoxymethyl)-2,5,5,8a-tetramethyl-decahydronaphthalen-2-ol (37) (0.71 g, 70%) as a colourless oil.

To a solution of (1S,2R,4aS,8aS)-1-(3,5-dimethoxyphenoxymethyl)-2,5,5,8a-tetramethyl-decahydronaphthalen-2-ol (37) (0.68 g, 1.8 mmol) in CH$_2$Cl$_2$ (20 mL), cooled to −78° C., a solution of SnCl$_4$ (1 mL, 8 mmol) in CH$_2$Cl$_2$ (10 mL) was added dropwise. The temperature was maintained at −78° C. for 4 h then the mixture was allowed to warm to room temperature overnight. The reaction was quenched with saturated aqueous sodium bicarbonate (50 mL). The organic layer was separated, dried (Na$_2$SO$_4$) and concentrated. Purification by column chromatography on silica gel (Hexanes/EtOAc, 6:1) gave (1R,10R,11S,16S)-3,5-dimethoxy-1,11,15,15-tetramethyl-8-oxatetracyclo[8.8.0.0$^{2,7}$.0$^{11,16}$]octadeca-2,4,6-triene (Compound No. 38) (0.49 g, 76%) as a colourless oil. $^1$H NMR (CDCl$_3$): δ 6.00 (d, 1H), 5.95 (d, 1H), 4.21 (m, 1H), 3.95 (t, 1H), 3.72 (d, 6H), 3.00 (m, 1H), 1.80-0.95 (m, 13H), 0.90 (s, 3H), 0.88 (m, 1H), 0.83 (s, 3H), 0.80 (s, 3H).

Example 20

Synthesis of (1R,10R,11S,16S)-5-methoxy-1,11,15,15-tetramethyl-8-oxatetracyclo[8.8.0.0$^{2,7}$.0$^{11,16}$]octadeca-2,4,6-trien-3-ol (COMPOUND No. 39)

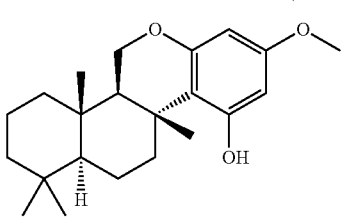

-continued

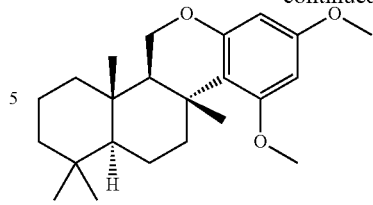
38

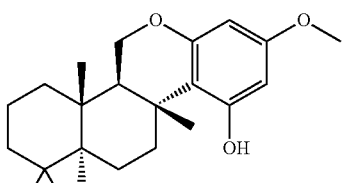

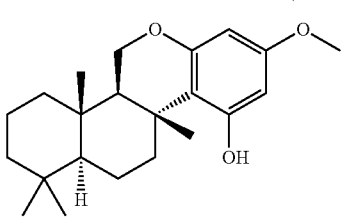
39

In a microwave tube, (1R,10R,11S,16S)-3,5-dimethoxy-1,11,15,15-tetramethyl-8-oxatetracyclo[8.8.0.0$^{2,7}$.0$^{11,16}$]octadeca-2,4,6-triene (Compound No. 38) (0.15 g, 0.42 mmol), Na$_2$S (0.20 g, 2.6 mmol) and NMP (3 mL) were placed. The tube was sealed and subjected to microwave heating at 180° C. for 1 h. The reaction was cooled to room temperature, diluted with EtOAc (100 mL) and washed with water (50 mL). The organic layer was separated, dried (Na$_2$SO$_4$) and concentrated. Purification by column chromatography on silica gel (Hexanes/EtOAc, 4:1) gave (1R,10R,11S,16S)-5-methoxy-1,11,15,15-tetramethyl-8-oxatetracyclo[8.8.0.0$^{2,7}$.0$^{11,16}$]octadeca-2,4,6-trien-3-ol (Compound No. 39) (0.06 g, 43%) as a colourless solid. $^1$H NMR (CDCl$_3$): δ 6.15 (d, 1H), 6.00 (d, 1H), 4.93 (s, 1H), 4.27 (m, 1H), 3.97 (t, 1H), 3.68 (s, 3H), 3.00 (m, 1H), 1.75-1.40 (m, 8H), 1.37 (s, 3H), 1.20-0.93 (m, 2H), 0.92 (s, 3H), 0.90 (m, 1H) 0.68 (s, 3H), 0.62 (s, 3H). MS m/z 345 (C$_{22}$H$_{32}$O$_3$+H$^+$).

Example 21

Synthesis of (1R,10R,11S,16S)-4,6-dimethoxy-1,11,15,15-tetramethyl-8-oxatetracyclo[8.8.0.0$^{2,7}$.0$^{11,16}$] octadeca-2,4,6-triene (COMPOUND NO. 42)

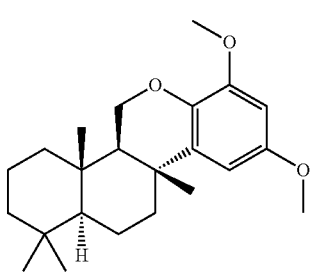
40

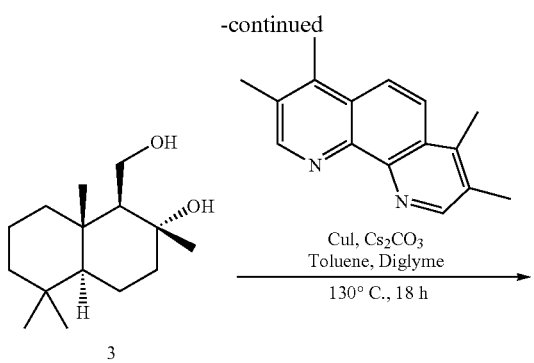

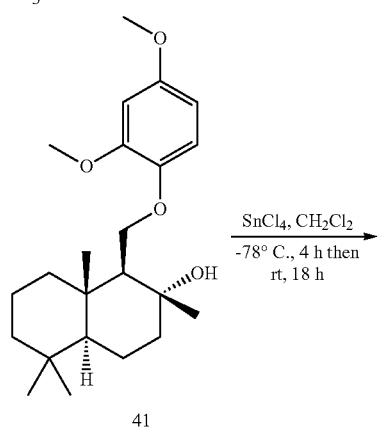

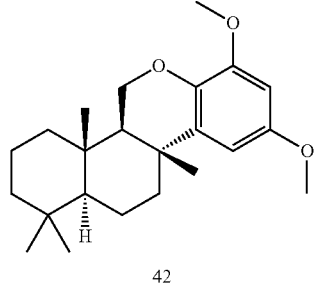

In a sealed tube purged with nitrogen, 1-iodo-2,4-dimethoxybenzene (40) (3.02 g, 11.4 mmol), (1S,2R,4aS,8aS)-1-(hydroxymethyl)-2,5,5,8a-tetramethyl-decahydronaphthalen-2-ol (3) (2.50 g, 10.4 mmol), $Cs_2CO_3$ (5.10 g, 15.6 mmol), 3,4,7,8-tetramethyl-[1,10]-phenylthroline (0.50 g, 2.1 mmol), CuI (0.16 g, 1.0 mmol), diglyme (10 mL) and toluene (30 mL) were placed. The reaction mixture was stirred at 130° C. for 18 h. The reaction was cooled to room temperature, diluted with EtOAc (600 mL) and washed with water (200 mL). The solid material was removed by filtration. The organic layer was separated, dried ($Na_2SO_4$) and concentrated. Purification by column chromatography on silica gel (Hexanes/EtOAc, 4:1) gave (1S,2R,4aS,8aS)-1-(2,4-dimethoxyphenoxymethyl)-2,5,5,8a-tetramethyl-decahydronaphthalen-2-ol (41) (2.50 g, 64%) as an off white solid.

To a solution of (1S,2R,4aS,8aS)-1-(2,4-dimethoxyphenoxymethyl)-2,5,5,8a-tetramethyl-decahydronaphthalen-2-ol (41) (0.90 g, 2.4 mmol) in $CH_2Cl_2$ (20 mL), cooled to −78° C., a solution of $SnCl_4$ (1.11 mL, 9.56 mmol) in $CH_2Cl_2$ (10 mL) was added dropwise. The temperature was maintained at −78° C. for 4 h then the mixture was allowed to warm to room temperature overnight. The reaction was quenched with water (50 mL). The organic layer was separated, dried ($Na_2SO_4$) and concentrated. Purification by column chromatography on silica gel (Hexanes/EtOAc, 4:1) gave (1R,10R,11S,16S)-4,6-dimethoxy-1,11,15,15-tetramethyl-8-oxatetracyclo[8.8.0.0$^{2,7}$.0$^{11,16}$]octadeca-2,4,6-triene (Compound No. 42) (0.69 g, 80%) as a viscous yellow oil. $^1$H NMR (CDCl$_3$): δ 6.33 (d, 1H), 6.00 (d, 1H), 4.45 (m, 1H), 4.18 (t, 1H), 3.83 (s, 3H), 3.75 (s, 3H), 2.25 (m, 1H) 1.80-1.38 (m, 7H), 1.35 (s, 3H), 1.25-1.00 (m, 4H) 0.92 (s, 3H), 0.87 (s, 3H), 0.82 (s, 3H).

Example 22

Synthesis of (1R,10R,11S,16S)-1,11,15,15-tetramethyl-8-oxatetracyclo[8.8.0.0$^{2,7}$.0$^{11,16}$]octadeca-2,4,6-triene-4,6-diol (COMPOUND NO. 43)

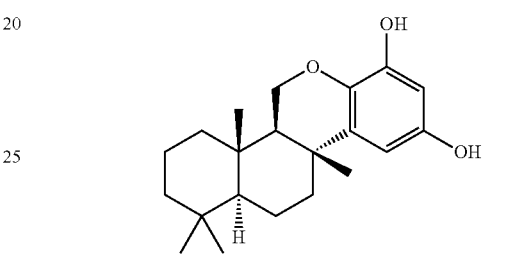

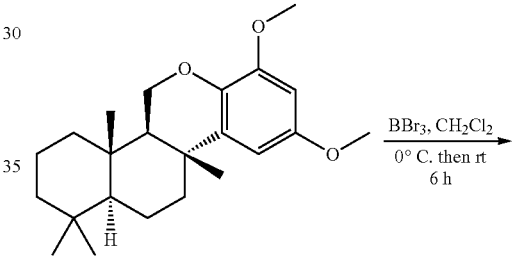

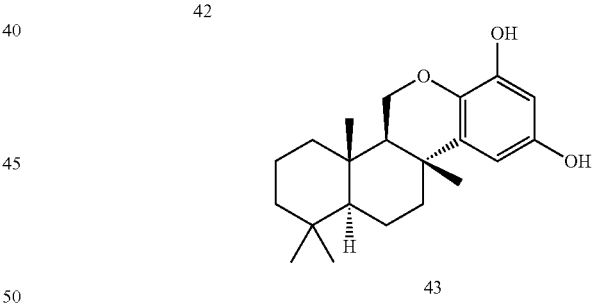

To a solution of (1R,10R,11S,16S)-4,6-dimethoxy-1,11,15,15-tetramethyl-8-oxatetracyclo[8.8.0.0$^{2,7}$.0$^{11,16}$]octadeca-2,4,6-triene (Compound No. 42) (0.69 g, 1.9 mmol) in $CH_2Cl_2$ (20 mL), cooled to 0° C., and a BBr$_3$ solution (7.3 mL, 1 M in $CH_2Cl_2$, 7.3 mmol) was added dropwise. The ice bath was removed and the reaction was stirred at room temperature for 6 h. The reaction was quenched with MeOH (20 mL) and concentrated. The quenching and concentration steps were repeated six times. Purification by column chromatography on silica gel (Hexanes/EtOAc, 4:1) gave (1R,10R,11S,16S)-1,11,15,15-tetramethyl-8-oxatetracyclo[8.8.0.0$^{2,7}$.0$^{11,16}$]octadeca-2,4,6-triene-4,6-diol (Compound No. 43) (0.42 g, 66%) as a pale pink solid. $^1$H NMR (CDCl$_3$): δ 6.28 (d, 1H), 6.17 (d, 1H), 5.48 (br s, 1H), 4.40 (m, 1H), 4.25 (br s, 1H), 4.15 (t, 1H), 2.20 (m, 1H), 1.80-1.35 (m, 7H), 1.28

(s, 3H), 1.25-1.00 (m, 4H), 0.92 (s, 3H), 0.88 (s, 3H), 0.82 (s, 3H). MS m/z 331 ($C_{21}H_{30}O_3$+H$^+$).

9H), 1.29 (s, 3H), 1.16 (m, 1H), 1.05 (m, 1H), 0.94 (s, 3H), 0.87 (s, 3H), 0.85 (s, 3H). MS m/z 345 ($C_{22}H_{32}O_3$+H$^+$).

Example 23

Synthesis of (1R,10R,11S,16S)-4-methoxy-1,11,15,15-tetramethyl-8-oxatetracyclo[8.8.0.0$^{2,7}$.0$^{11,16}$]octadeca-2,4,6-trien-6-ol

Example 24

Synthesis of (1R,10R,11S,16S)-1,11,15,15-tetramethyl-3,5-bis(propan-2-yloxy)-8-oxatetracyclo[8.8.0.0$^{2,7}$.0$^{11,16}$]octadeca-2,4,6-triene (COMPOUND NO. 44)

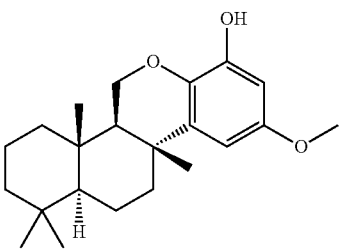

(COMPOUND NO. 49)

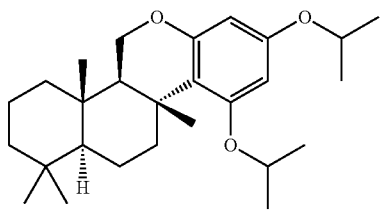

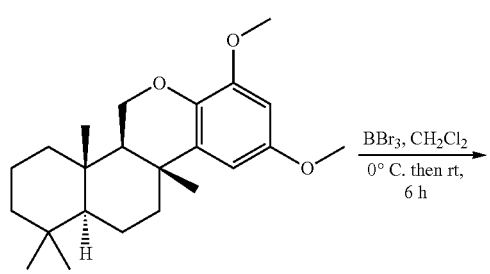

42

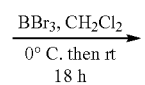

35

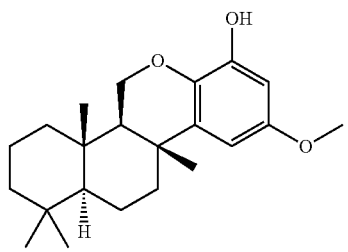

44

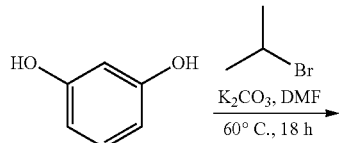

45

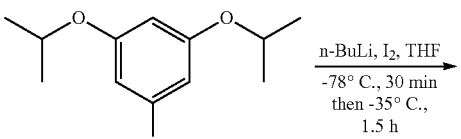

46

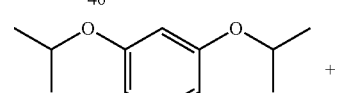

47

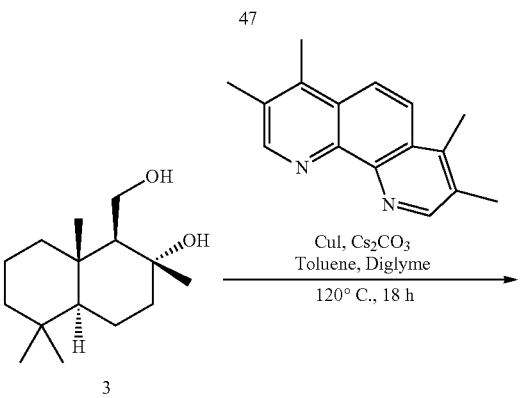

3

To a solution of (1R,10R,11S,16S)-4,6-dimethoxy-1,11,15,15-tetramethyl-8-oxatetracyclo[8.8.0.0$^{2,7}$.0$^{11,16}$]octadeca-2,4,6-triene (Compound No. 42) (0.186 g, 0.519 mmol) in anhydrous $CH_2Cl_2$ (10 mL) at 0° C. under nitrogen, BBr$_3$ (1.0 M in $CH_2Cl_2$, 0.54 mL, 0.54 mmol) was added dropwise. The solution was stirred at room temperature for 6 h. The reaction was quenched at 0° C. with anhydrous MeOH (6 mL) and evaporated. The residue was co-evaporated with MeOH (4×20 mL) and dried in vacuo. Purification by column chromatography on silica gel (Hexanes/EtOAc, 10:1) gave a product, which was triturated with MeOH (4.5 mL) to afford (1R,10R,11S,16S)-4-methoxy-1,11,15,15-tetramethyl-8-oxatetracyclo[8.8.0.0$^{2,7}$.0$^{11,16}$]octadeca-2,4,6-trien-6-ol (Compound No. 44) (86 mg, 49%) as a white solid. $^1$H NMR (CDCl$_3$): δ 6.38 (d, 1H), 6.24 (d, 1H), 5.49 (s, 1H), 4.40 (dd, 1H), 4.16 (dd, 1H), 3.71 (s, 3H), 2.25 (dd, 1H), 1.78-1.38 (m,

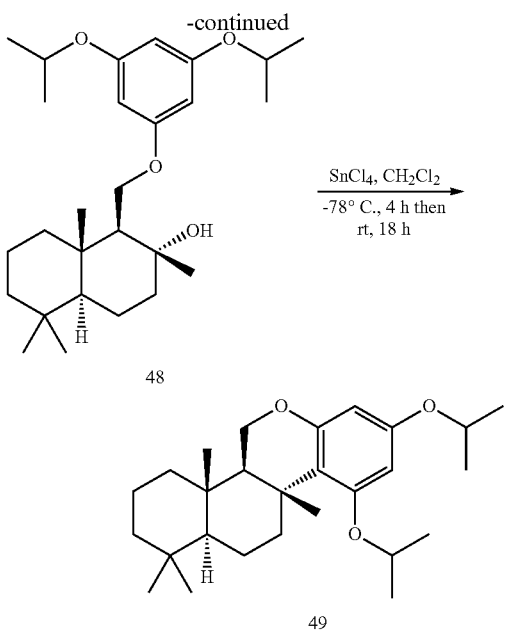

To a solution of (35) (15.0 g, 69.0 mmol) in CH$_2$Cl$_2$ (40 mL), cooled to 0° C., a 1 M BBr$_3$ solution in CH$_2$Cl$_2$ (140 mL, 140 mmol) was added dropwise. The ice bath was removed and the reaction was stirred at room temperature for 18 h. The reaction was quenched with MeOH and concentrated. The residue was dissolved in EtOAc (500 mL) and washed with water (300 mL). The organic layer was separated, dried (Na$_2$SO$_4$) and concentrated to give 5-bromobenzene-1,3-diol (45) (13.03 g, >99%) as an orange oil.

To a solution of 5-bromobenzene-1,3-diol (45) (13.0 g, 69.0 mmol) in DMF (150 mL), K$_2$CO$_3$ (38.1 g, 276 mmol) was added at room temperature, followed by the addition of 2-bromopropane (26.0 mL, 276 mmol). The mixture was heated to 60° C. and stirred for 18 h. The reaction was cooled to room temperature, quenched with water (700 mL) and extracted with EtOAc (3×300 mL). The organic layer was separated, dried (Na$_2$SO$_4$) and concentrated. Purification by column chromatography on silica gel (Hexanes/EtOAc, 10:1) gave 1-bromo-3,5-bis(propan-2-yloxy)benzene (46) (17.6 g, 93%) as an orange oil.

To a solution of 1-bromo-3,5-bis(propan-2-yloxy)benzene (46) (2.0 g, 7.3 mmol) in THF (100 mL), cooled to −78° C., a 1.6 M n-BuLi solution in hexanes (9.16 mL, 14.7 mmol) was added dropwise. The temperature was maintained at −78° C. for 30 min, after which a solution of iodine (3.17 g, 29.3 mmol) in THF (15 mL) was added dropwise. The mixture was warmed to −35° C. and maintained at this temperature for 1.5 h. The reaction mixture was diluted with EtOAc (100 mL) and washed with water (2×50 mL) and brine (50 mL). The organic layer was separated, dried (Na$_2$SO$_4$) and concentrated. Purification by column chromatography on silica gel (Hexanes/EtOAc, 4:1) gave 1-iodo-3,5-bis(propan-2-yloxy)benzene (47) (1.85 g, 79%) as a viscous orange oil.

In a sealed tube purged with nitrogen, compound (47) (1.85 g, 5.78 mmol), (1S,2R,4aS,8aS)-1-(hydroxymethyl)-2,5,5,8a-tetramethyl-decahydronaphthalen-2-ol (3) (1.26 g, 5.25 mmol), Cs$_2$CO$_3$ (2.56 g, 7.87 mmol), 3,4,7,8-tetramethyl-[1,10]-phenylthroline (0.25 g, 1.0 mmol), CuI (0.10 g, 0.70 mmol), diglyme (5 mL) and toluene (20 mL) were placed. The reaction mixture was stirred at 120° C. for 18 h. The reaction was cooled to room temperature, diluted with EtOAc (600 mL) and washed with water (200 mL). The solid material was removed by filtration. The organic layer was separated, dried (Na$_2$SO$_4$) and concentrated. Purification by column chromatography on silica gel (Hexanes/EtOAc, 4:1) gave (1S,2R,4aS,8aS)-1-[3,5-bis(propan-2-yloxy)phenoxymethyl]-2,5,5,8a-tetramethyl-decahydronaphthalen-2-ol (48) (1.50 g, 66%) as a colourless oil.

To a solution of (1S,2R,4aS,8aS)-1-[3,5-bis(propan-2-yloxy)phenoxy-methyl]-2,5,5,8a-tetramethyl-decahydronaphthalen-2-ol (48) (0.90 g, 2.1 mmol) in CH$_2$Cl$_2$ (20 mL), cooled to −78° C., a solution of SnCl$_4$ (0.97 mL, 8.3 mmol) in CH$_2$Cl$_2$ (10 mL) was added dropwise. The temperature was maintained at −78° C. for 4 h, after which the reaction mixture was allowed to warm to room temperature overnight. The reaction was quenched with water (50 mL). The organic layer was separated, dried (Na$_2$SO$_4$) and concentrated. Purification by column chromatography on silica gel (Hexanes/toluene, 1:1) gave (1R,10R,11S,16S)-1,11,15,15-tetramethyl-3,5-bis(propan-2-yloxy)-8-oxatetracyclo[8.8.0.0$^{2,7}$.0$^{11,16}$]octadeca-2,4,6-triene (Compound No. 49) (0.20 g, 23%) as a tan solid. $^1$H NMR (CDCl$_3$): δ 5.95 (d, 1H), 5.87 (d, 1H), 4.50 (m, 1H), 4.40 (m, 1H), 4.22 (m, 1H), 3.95 (t, 1H), 3.10 (m, 1H) 1.78-1.40 (m, 7H), 1.37 (m, 15H), 1.25-1.00 (m, 4H) 0.92 (s, 3H), 0.87 (s, 3H), 0.82 (s, 3H).

Example 25

Synthesis of (1R,10R,11S,16S)-1,11,15,15-tetramethyl-8-oxatetracyclo[8.8.0.0$^{2,7}$.0$^{11,16}$]octadeca-2,4,6-triene-3,5-diol

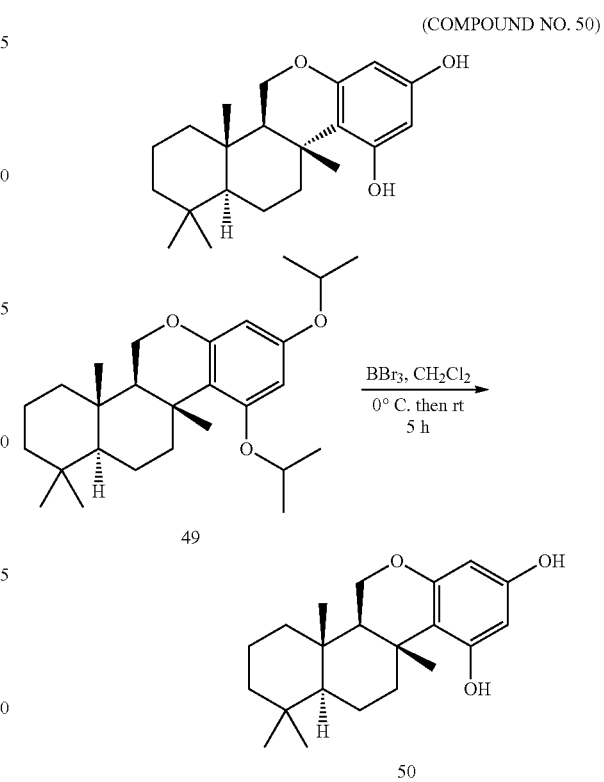

(COMPOUND NO. 50)

To a solution of (1R,10R,11S,16S)-1,11,15,15-tetramethyl-3,5-bis(propan-2-yloxy)-8-oxatetracyclo[8.8.0.0$^{2,7}$.0$^{11,16}$]octadeca-2,4,6-triene (Compound No. 49) (0.20 g, 0.48 mmol) in CH$_2$Cl$_2$ (10 mL), cooled to 0° C., a 1 M BBr$_3$ solution in CH$_2$Cl$_2$ (1.8 mL, 1.8 mmol) was added dropwise. The ice bath was removed and the reaction was stirred at room temperature for 5 h. The reaction was quenched with MeOH (10 mL) and concentrated. This quench/concentration step was repeated 5 times. Purification by column chromatography on silica gel (Hexanes/EtOAc, 4:1) gave (1R,10R,11S, 16S)-1,11,15,15-tetramethyl-8-oxatetracyclo[8.8.0.0$^{2,7}$.0$^{11,16}$]octadeca-2,4,6-triene-3,5-diol (Compound No. 50) (0.08 g, 50%) as a tan solid. $^1$H NMR (CDCl$_3$): δ 5.85 (d, 1H), 5.75 (d, 1H), 4.62 (s, 1H), 4.42 (s, 1H), 4.25 (m, 1H), 3.97 (t, 1H), 3.00 (m, 1H), 1.75-1.40 (m, 7H), 1.38 (s, 3H), 1.23-1.00 (m, 2H), 0.98-0.80 (m, 5H), 0.78 (s, 3H), 0.73 (s, 3H). MS m/z 331 (C$_{21}$H$_{30}$O$_3$+H$^+$).

Example 26

Synthesis of (1R,10R,11S,16S)-5-methoxy-1,11,15, 15-tetramethyl-8-thiatetracyclo[8.8.0.0$^{2,7}$.0$^{11,16}$] octadeca-2,4,6-triene and (1R,10R,11S,16S)-3-methoxy-1,11,15,15-tetramethyl-8-thiatetracyclo [8.8.0.0$^{2,7}$.0$^{11,16}$]octadeca-2,4,6-triene (COMPOUND NO. 51)

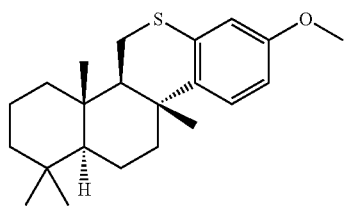

and (COMPOUND NO. 52)

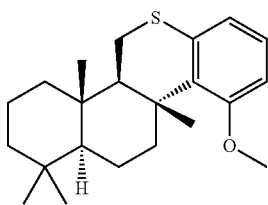

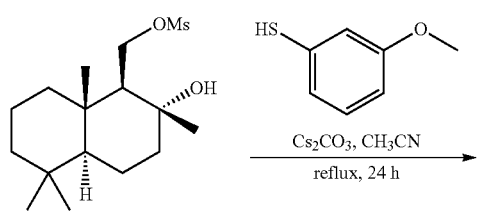

-continued

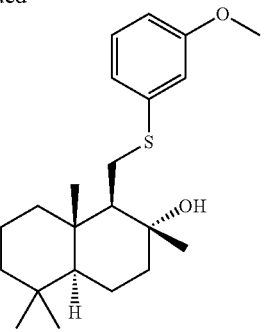

13-1

| SnCl$_4$, CH$_2$Cl$_2$
-78° C., 4 h

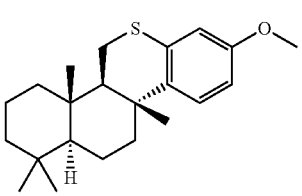 + 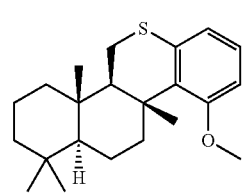

51        52

A mixture of 3-methoxythiophenol (2.20 g, 15.7 mmol), [(1S,2R,4aS,8aS)-2-hydroxy-2,5,5,8a-tetramethyl-decahydronaphthalen-1-yl]methyl methanesulfonate (12) (5.0 g, 15 mmol), and Cs$_2$CO$_3$ (15.30 g, 47.16 mmol) in CH$_3$CN (600 mL) was stirred at room temperature for 1 h, then refluxed for 24 h. After cooling, the mixture was concentrated and purified by column chromatography on silica gel (Hexanes/EtOAc, 10:1 to 6:1) to give (1R,2R,4aS,8aS)-1-{[(3-methoxyphenyl)sulfanyl]methyl}-2,5,5,8a-tetramethyl-decahydronaphthalen-2-ol (13-1) (4.03 g, 71%) as a yellow oil.

To a solution of (1R,2R,4aS,8aS)-1-{[(3-methoxyphenyl) sulfanyl]methyl}-2,5,5,8a-tetramethyl-decahydronaphthalen-2-ol (12b) (2.5 g, 6.9 mmol) in CH$_2$Cl$_2$ (70 mL), cooled to −78° C., a solution of SnCl$_4$ (3.22 mL, 27.6 mmol) in CH$_2$Cl$_2$ (30 mL) was added dropwise. The mixture was stirred at −78° C. for 4 h. The reaction was quenched with water (100 mL), and the organic layer was separated, dried (Na$_2$SO$_4$), and concentrated. Purification by column chromatography on silica gel (Hexanes/toluene, 2:1) gave (1R,10R,11S,16S)-5-methoxy-1,11,15,15-tetramethyl-8-thiatetracyclo[8.8.0. 0$_{2,7}$.0$^{11,16}$]octadeca-2,4,6-triene (Compound No. 51) (1.10 g, 46%) as a white solid. $^1$H NMR (CDCl$_3$): δ 7.19 (d, 1H), 6.58 (m, 2H), 3.72 (s, 3H), 2.95 (q, 2H), 2.40 (m, 1H), 1.84-1.35 (m, 9H), 1.20 (s, 3H), 1.18-0.99 (m, 2H), 0.95 (s, 3H), 0.85 (s, 3H), 0.82 (s, 3H). (1R,10R,11S,16S)-3-Methoxy-1,11,15,15-tetramethyl-8-thiatetracyclo[8.8.0.0$^{2,7}$.0$^{11,16}$]octadeca-2,4, 6-triene (Compound No. 52) (0.44 g, 19%) was also isolated as a white solid. $^1$H NMR (CDCl$_3$): δ 6.96 (t, 1H), 6.67 (d, 1H), 6.56 (d, 1H), 3.78 (s, 3H), 3.32 (m, 1H), 2.82 (q, 2H), 1.82-1.40 (m, 7H), 1.38 (s, 3H), 1.35-0.98 (m, 3H), 0.92 (s, 3H), 0.95 (m, 1H), 0.87 (s, 3H), 0.83 (s, 3H).

Example 27

Synthesis of (1R,10R,11S,16S)-1,11,15,15-tetramethyl-8-thiatetracyclo[8.8.0.0², 7.0¹¹,16]octadeca-2,4,6-trien-5-ol

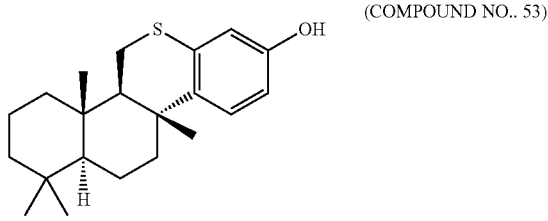

(COMPOUND NO. 53)

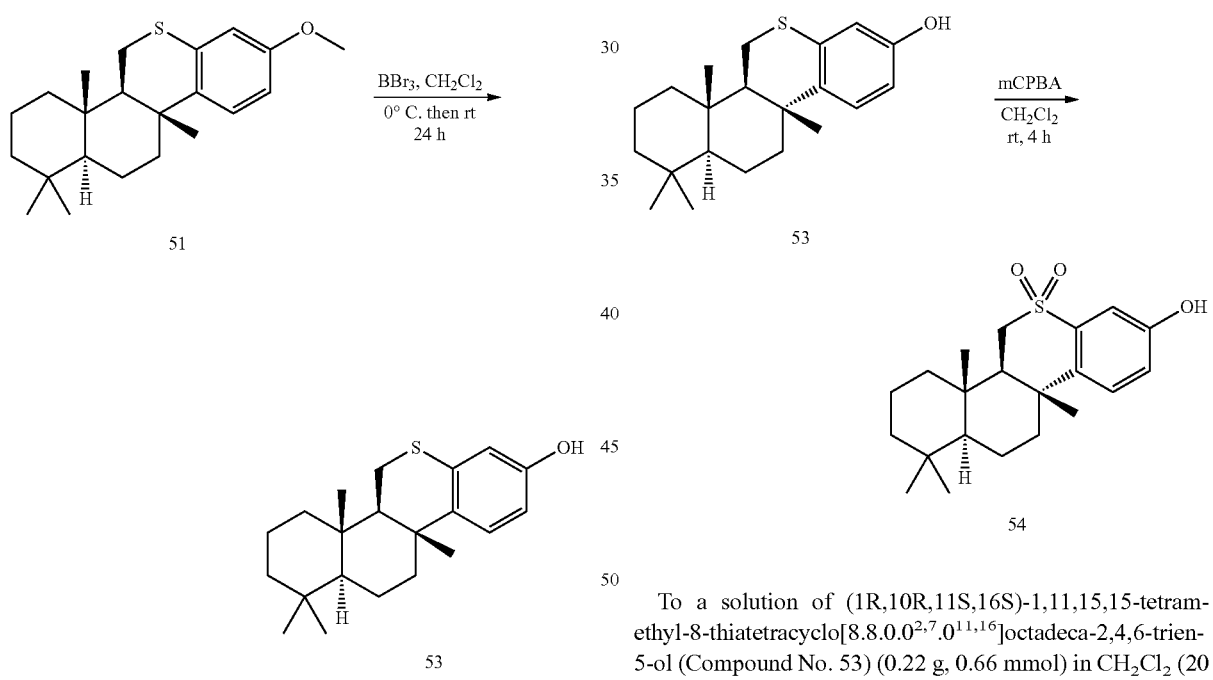

To a solution of (1R,10R,11S,16S)-5-methoxy-1,11,15,15-tetramethyl-8-thiatetracyclo[8.8.0.0$^{2,7}$.0$^{11,16}$]octadeca-2,4,6-triene (51) (0.25 g, 0.73 mmol) in CH$_2$Cl$_2$ (10 mL), cooled to 0° C., a solution of BBr$_3$ (1.0 M in CH$_2$Cl$_2$, 2.90 mL, 2.90 mmol) was added and the resulting mixture was stirred at room temperature for 24 h. The reaction was quenched with MeOH (3×10 mL) and concentrated to dryness. Purification by column chromatography on silica gel (Hexanes/EtOAc, 10:1) gave (1R,10R,11S,16S)-1,11,15,15-tetramethyl-8-thiatetracyclo[8.8.0.0$^{2,7}$.0$^{11,16}$]octadeca-2,4,6-trien-5-ol (Compound No. 53) (0.22 g, 92%) as a white solid. $^1$H NMR (CDCl$_3$): δ 7.14 (d, 1H), 6.49 (m, 2H), 4.45 (br s, 1H), 2.95 (q, 2H), 2.40 (m, 1H), 1.84-1.35 (m, 9H), 1.20 (s, 3H), 1.18-0.98 (m, 2H), 0.95 (s, 3H), 0.88 (m, 3H), 0.85 (s, 3H).

Example 28

Synthesis of (1R,10R,11S,16S)-5-hydroxy-1,11,15,15-tetramethyl-8-thiatetracyclo[8.8.0.0$^{2,7}$.0$^{11,16}$]octadeca-2,4,6-triene-8,8-dione

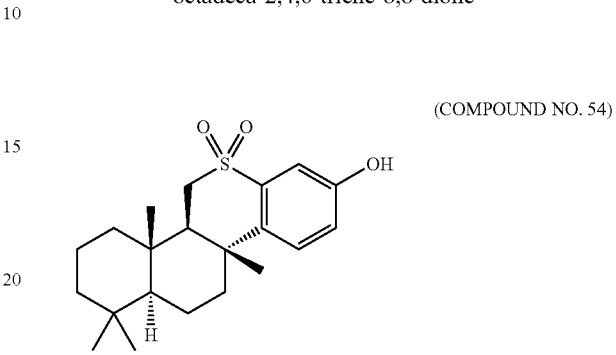

(COMPOUND NO. 54)

To a solution of (1R,10R,11S,16S)-1,11,15,15-tetramethyl-8-thiatetracyclo[8.8.0.0$^{2,7}$.0$^{11,16}$]octadeca-2,4,6-trien-5-ol (Compound No. 53) (0.22 g, 0.66 mmol) in CH$_2$Cl$_2$ (20 mL), 3-chloroperoxybenzoic acid (0.34 g of 77% purity, 1.5 mmol) was added and the mixture was stirred at room temperature for 4 h. The reaction mixture was concentrated, re-dissolved in EtOAc and vigorously stirred with saturated aqueous sodium bicarbonate for 30 min. The organic layer was separated, dried (Na$_2$SO$_4$) and concentrated. Purification by column chromatography on silica gel (Hexanes/EtOAc, 3:1) gave (1R,10R,11S,16S)-5-hydroxy-1,11,15,15-tetramethyl-8-thiatetracyclo[8.8.0.0$^{2,7}$.0$^{11,16}$]octadeca-2,4,6-triene-8,8-dione (Compound No. 54) (0.20 g, 83%) as a white solid. $^1$H NMR (CDCl$_3$): δ 7.35-7.20 (m, 2H), 7.00 (m, 1H), 3.37 (m, 2H), 2.45 (m, 1H), 2.26 (dd, 1H), 1.80-1.40 (m, 7H), 1.40 (s, 3H), 1.38-0.98 (m, 4H), 0.95 (s, 3H), 0.89 (s, 3H), 0.85 (s, 3H). MS m/z 361 ($C_{21}H_{30}O_3S-H^+$).

Example 29

Synthesis of (1R,10R,11S,16S)-1,11,15,15-tetramethyl-8-thiatetracyclo[8.8.0.0$^{2,7}$.0$^{11,16}$]octadeca-2,4,6-trien-3-ol

Example 30

Synthesis of (1R,10R,11S,16S)-3-hydroxy-1,11,15,15-tetramethyl-8-thiatetracyclo[8.8.0.0$^{2,7}$.0$^{11,16}$]octadeca-2,4,6-triene-8,8-dione

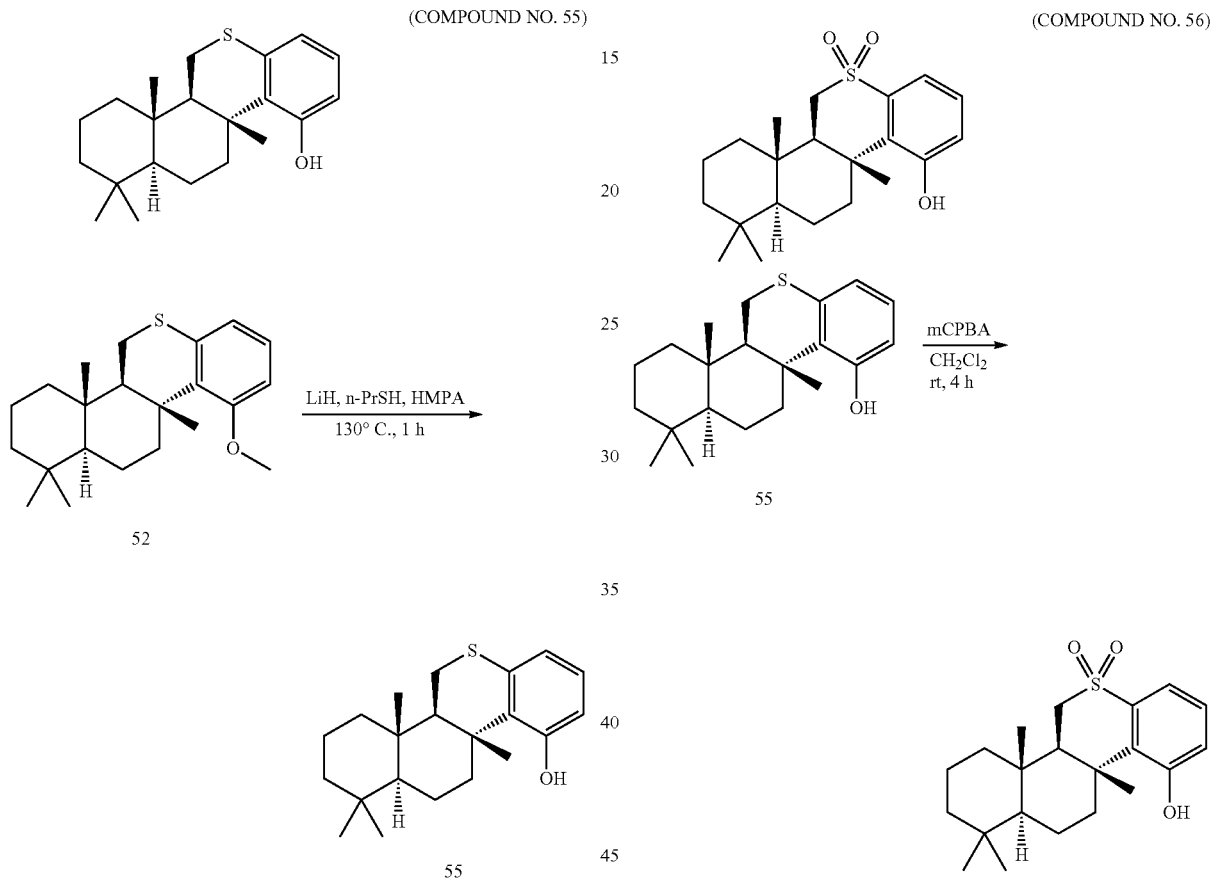

In a reaction vessel HMPA (5 mL) was placed and purged with nitrogen for 1 h. To the vessel LiH (0.137 g, 17.4 mmol) and n-propylthiol (1.65 mL, 18.3 mmol) were added and the mixture was stirred at room temperature for 30 min. A solution of (1R,10R,11S,16S)-3-methoxy-1,11,15,15-tetramethyl-8-thiatetracyclo[8.8.0.02, 7.011,16]octadeca-2,4,6-triene (Compound No. 52) (0.10 g, 0.29 mmol) in HMPA (5 mL) was added to the reaction mixture and heated at 130° C. for 1 h. The reaction was cooled to room temperature, quenched with water (50 mL) and extracted with EtOAc (3×200 mL). The organic layers were combined, dried (Na$_2$SO$_4$) and concentrated. Purification by column chromatography on silica gel (Hexanes/EtOAc, 10:1) gave (1R,10R, 11S,16S)-1,11,15,15-tetramethyl-8-thiatetracyclo[8.8.0. 0$^{2,7}$.0$^{11,16}$]octadeca-2,4,6-trien-3-ol (Compound No. 55) (0.09 g, 94%) as a white solid. $^1$H NMR (CDCl$_3$): δ 6.81 (t, 1H), 6.63 (d, 1H), 6.28 (d, 1H), 4.70 (s, 1H), 3.38 (m, 1H), 2.82 (q, 2H), 1.90-1.40 (m, 9H), 1.38 (s, 3H), 1.36-0.98 (m, 2H), 0.95 (s, 3H), 0.88 (m, 3H), 0.85 (s, 3H).

To a solution of (1R,10R,11S,16S)-1,11,15,15-tetramethyl-8-thiatetracyclo[8.8.0.0$^{2,7}$.0$^{11,16}$]octadeca-2,4,6-trien-3-ol (Compound No. 55) (0.10 g, 0.30 mmol) in CH$_2$Cl$_2$ (10 mL), 3-chloroperoxybenzoic acid (0.34 g of 77% pure material, 0.70 mmol) was added and the mixture was stirred at room temperature for 4 h. The reaction mixture was concentrated, re-dissolved in EtOAc and vigorously stirred with saturated aqueous sodium bicarbonate for 30 min. The organic layer was separated, dried (Na$_2$SO$_4$) and concentrated. Purification by column chromatography on silica gel (Hexanes/EtOAc, 7:1) gave (1R,10R,11S,16S)-3-hydroxy-1, 11,15,15-tetramethyl-8-thiatetracyclo[8.8.0.0$^{2,7}$.0$^{11,16}$]octadeca-2,4,6-triene-8,8-dione (Compound No. 56) (0.06 g, 55%) as a white solid. $^1$H NMR (CDCl$_3$): δ 7.46 (d, 1H), 7.19 (t, 1H), 6.83 (d, 1H), 6.19 (br s, 1H), 3.30 (m, 3H), 2.30 (d, 1H), 1.87-1.45 (m, 5H), 1.43 (s, 3H), 1.41-1.00 (m, 5H), 0.96 (s, 3H), 0.87 (s, 3H), 0.83 (s, 3H). MS m/z 361 ($C_{21}H_{30}O_3S-H^+$).

Example 31

Synthesis of (1R,10S,11S,16S)-3-hydroxy-N,11,15,15-tetramethyl-8,8-dioxo-8$\lambda^6$-thiatetracyclo[8.8.0.0$^{2,7}$.0$^{11,16}$]octadeca-2,4,6-triene-5-carboxamide

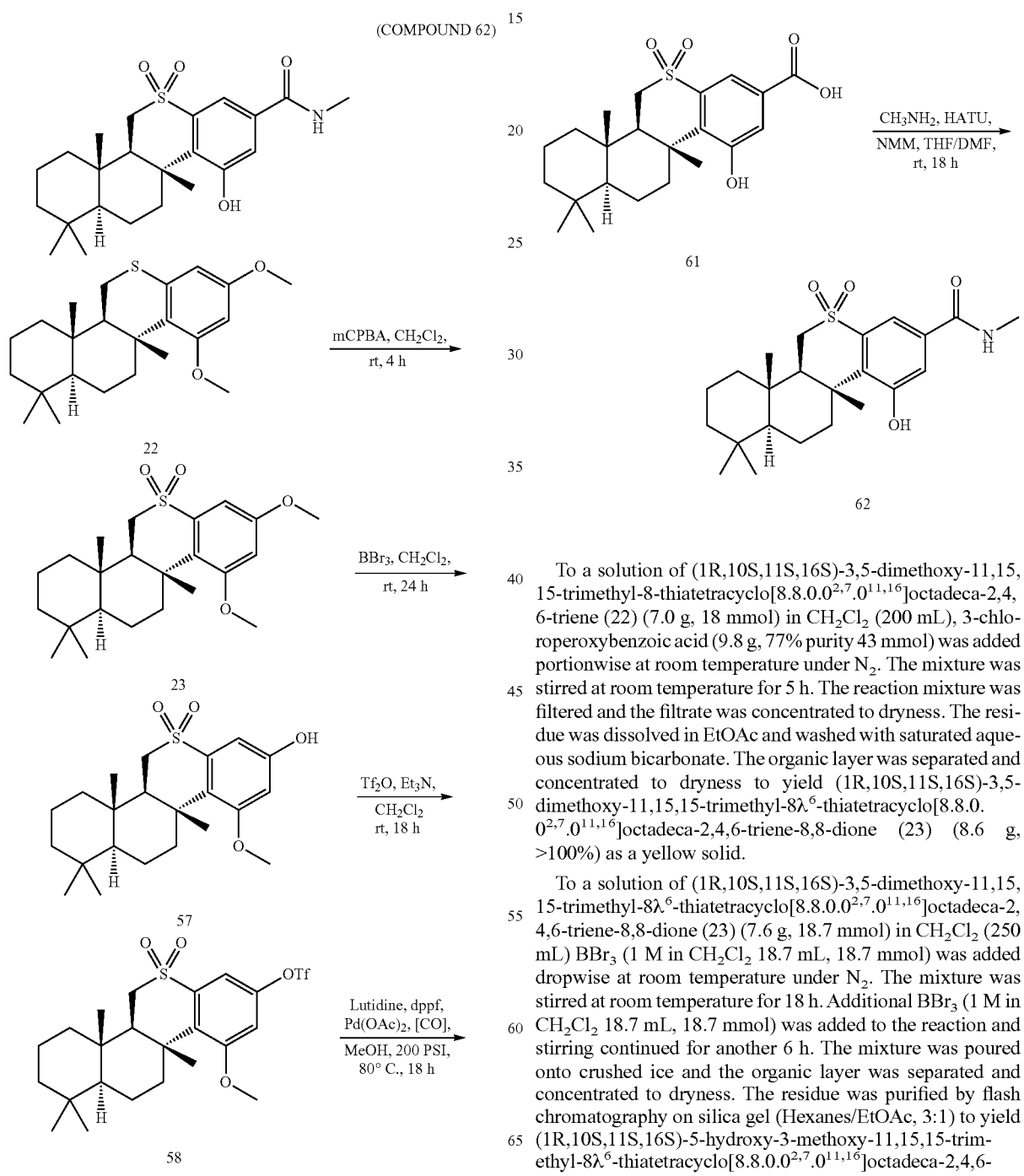

To a solution of (1R,10S,11S,16S)-3,5-dimethoxy-11,15,15-trimethyl-8-thiatetracyclo[8.8.0.0$^{2,7}$.0$^{11,16}$]octadeca-2,4,6-triene (22) (7.0 g, 18 mmol) in $CH_2Cl_2$ (200 mL), 3-chloroperoxybenzoic acid (9.8 g, 77% purity 43 mmol) was added portionwise at room temperature under $N_2$. The mixture was stirred at room temperature for 5 h. The reaction mixture was filtered and the filtrate was concentrated to dryness. The residue was dissolved in EtOAc and washed with saturated aqueous sodium bicarbonate. The organic layer was separated and concentrated to dryness to yield (1R,10S,11S,16S)-3,5-dimethoxy-11,15,15-trimethyl-8$\lambda^6$-thiatetracyclo[8.8.0.0$^{2,7}$.0$^{11,16}$]octadeca-2,4,6-triene-8,8-dione (23) (8.6 g, >100%) as a yellow solid.

To a solution of (1R,10S,11S,16S)-3,5-dimethoxy-11,15,15-trimethyl-8$\lambda^6$-thiatetracyclo[8.8.0.0$^{2,7}$.0$^{11,16}$]octadeca-2,4,6-triene-8,8-dione (23) (7.6 g, 18.7 mmol) in $CH_2Cl_2$ (250 mL) $BBr_3$ (1 M in $CH_2Cl_2$ 18.7 mL, 18.7 mmol) was added dropwise at room temperature under $N_2$. The mixture was stirred at room temperature for 18 h. Additional $BBr_3$ (1 M in $CH_2Cl_2$ 18.7 mL, 18.7 mmol) was added to the reaction and stirring continued for another 6 h. The mixture was poured onto crushed ice and the organic layer was separated and concentrated to dryness. The residue was purified by flash chromatography on silica gel (Hexanes/EtOAc, 3:1) to yield (1R,10S,11S,16S)-5-hydroxy-3-methoxy-11,15,15-trimethyl-8$\lambda^6$-thiatetracyclo[8.8.0.0$^{2,7}$.0$^{11,16}$]octadeca-2,4,6-triene-8,8-dione (57) (4.2 g, 57%) as a pale brown solid.

To a solution of (1R,10S,11S,16S)-5-hydroxy-3-methoxy-11,15,15-trimethyl-8λ$^6$-thiatetracyclo[8.8.0.0$^{2,7}$.0$^{11,16}$]octadeca-2,4,6-triene-8,8-dione (57) (4.7 g, 12 mmol) in CH$_2$Cl$_2$ (200 mL), triethylamine (1.5 mL, 17 mmol) was added followed by the addition of trifluoromethanesulfonic anhydride (1.9 mL, 14 mmol) under nitrogen. The mixture was stirred at room temperature for 18 h. The reaction was concentrated to dryness. The crude product was purified by flash chromatography on silica gel (Hexanes/EtOAc, 2:1) to yield (1R,10S, 11S,16S)-3-methoxy-11,15,15-trimethyl-8,8-dioxo-8λ$^6$-thiatetracyclo-[8.8.0.0$^{2,7}$.0$^{11,16}$]octadeca-2,4,6-trien-5-yl trifluoromethanesulfonate (58) (5.5 g, 87%) as a pale brown solid.

In a steel bomb (1R,10S,11S,16S)-3-methoxy-11,15,15-trimethyl-8,8-dioxo-8λ$^6$-thiatetracyclo[8.8.0.0$^{2,7}$.0$^{11,16}$]octadeca-2,4,6-trien-5-yl trifluoromethanesulfonate (58) (5.5 g, 10 mmol), 2,6-lutidine (2.9 mL, 24 mmol), Pd(OAc)$_2$ (0.28 g, 1.2 mmol), dppf (0.67 g, 1.2 mmol) and anhydrous methanol (150 mL) were placed. The bomb was sealed, filled with carbon monoxide at 200 psi and stirred at 80° C. for 18 h. The reaction mixture was cooled to room temperature, filtered through a Celite pad and the filtrate was concentrated to dryness. The residue was purified by flash chromatography on silica gel (Hexanes/EtOAc, 2:1) to yield methyl (1R,10S, 11S,16S)-3-methoxy-11,15,15-trimethyl-8,8-dioxo-8λ$^6$-thiatetracyclo[8.8.0.0$^{2,7}$.0$^{11,16}$]octadeca-2,4,6-triene-5-carboxylate (59) (3.6 g, 79%) as a white solid.

A mixture of lithium hydride (0.66 g, 83 mmol) and n-propanethiol (8.7 mL, 99 mmol) in HMPA (20 mL) was stirred at room temperature for 30 min under N$_2$. To the mixture (1R, 10S,11S,16S)-3-methoxy-11,15,15-trimethyl-8,8-dioxo-8λ$^6$-thiatetracyclo[8.8.0.0$^{2,7}$.0$^{11,16}$]octadeca-2,4,6-triene-5-carboxylate (59) (3.6 g, 8.3 mmol) in HMPA (10 mL) was added. The mixture was heated at 130° C. for 1 h. The mixture was cooled to room temperature and quenched with 1 M HCl, then extracted with EtOAc. The organic layer was concentrated to dryness. The residue was purified by flash chromatography on silica gel (CH$_2$Cl$_2$/MeOH, 10:1) to yield (1R, 10S,11S,16S)-3-methoxy-11,15,15-trimethyl-8,8-dioxo-8λ$^6$-thiatetracyclo[8.8.0.0$^{2,7}$.0$^{11,16}$]octadeca-2,4,6-triene-5-carboxylic acid (61) (3.2 g, 95% yield) as a white solid. $^1$H NMR (CD$_3$OD): δ 7.91 (d, 1H), 7.54 (d, 1H), 3.59 (m, 1H), 3.38 (m, 2H), 2.24 (m, 1H), 1.86 (m, 8H), 1.36-1.16 (m, 3H), 1.09-1.03 (m, 2H), 1.02 (s, 3H), 0.89 (s, 3H), 0.87 (s, 3H). MS m/z 405 (C$_{22}$H$_{30}$NO$_5$S–H$^+$).

A mixture of (1R,10S,11S,16S)-3-methoxy-11,15,15-trimethyl-8,8-dioxo-8λ$^6$-thiatetracyclo[8.8.0.0$^{2,7}$.0$^{11,16}$]octadeca-2,4,6-triene-5-carboxylic acid (61) (0.35 g, 0.83 mmol), HATU (0.61 g, 1.7 mmol), N-methylmorpholine (0.18 mL, 2.5 mmol), methylamine (2 M in THF, 1.04 mL, 2.08 mmol), THF (10.0 mL) and DMF (2.0 mL) in a sealed tube was stirred at room temperature for 18 h. The THF was evaporated and the residue was quenched with water. The resulting solid was collected by filtration. The crude product was purified by flash chromatography on silica gel (Hexanes/EtOAc, 1:1) to yield (1R,10S,11S,16S)-3-methoxy-N,11,15,15-tetramethyl-8,8-dioxo-8λ$^6$thiatetracyclo[8.8.0.0$^{2,7}$.0$^{11,16}$]-octadeca-2,4,6-triene-5-carboxamide (0.26 g, 74%) (Compound No. 62) as a white solid. $^1$H NMR (CDCl$_3$): δ 8.77 (s, 1H), 8.07 (s, 1H), 7.60 (s, 1H), 6.59 (m, 1H), 3.52 (m, 1H), 3.37 (m, 1H), 3.24 (m, 1H), 3.05 (d, 3H), 2.32 (d, 1H), 1.65-1.10 (m, 13H), 0.97 (s, 3H), 0.88 (s, 3H), 0.84 (s, 3H). MS m/z 420 (C$_{23}$H$_{33}$NO$_4$S+H$^+$).

Example 32

Synthesis of (1R,10R,11R,16S)-5-hydroxy-N,1,11, 15,15,16-pentamethyl-8,8-dioxo-8Λ$^6$-thiatetracyclo[8.8.0. 0$^{2,7}$.0$^{11,16}$]octadeca-2,4,6-triene-3-carboxamide

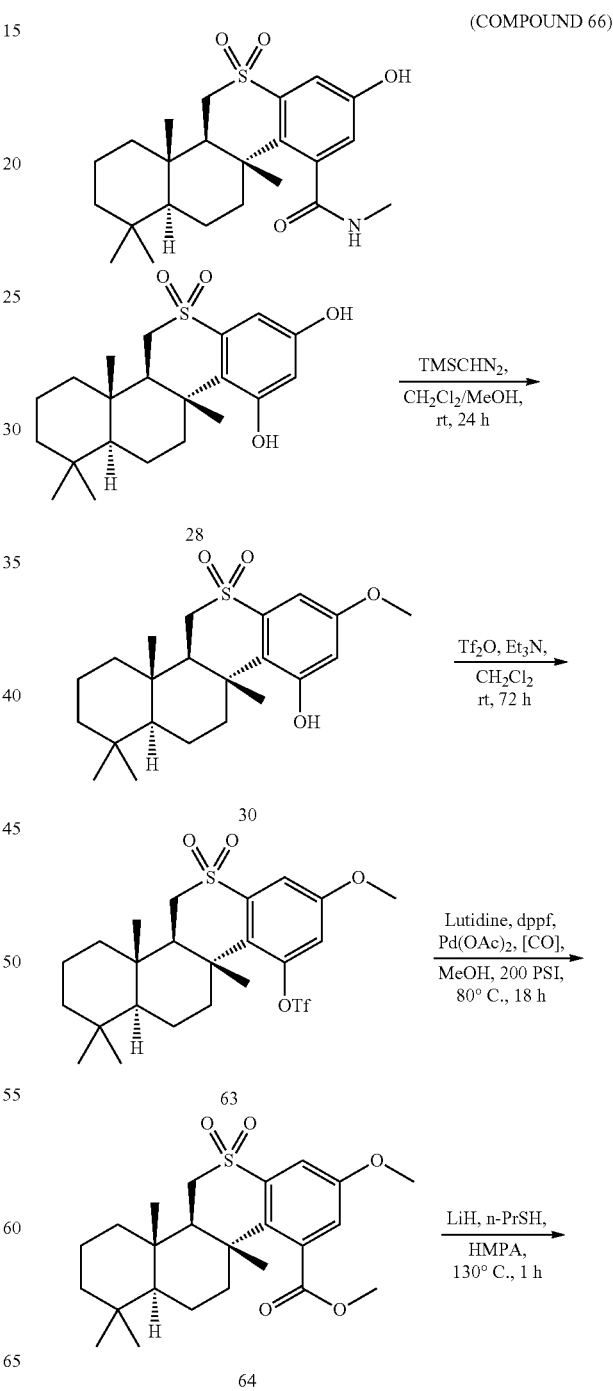

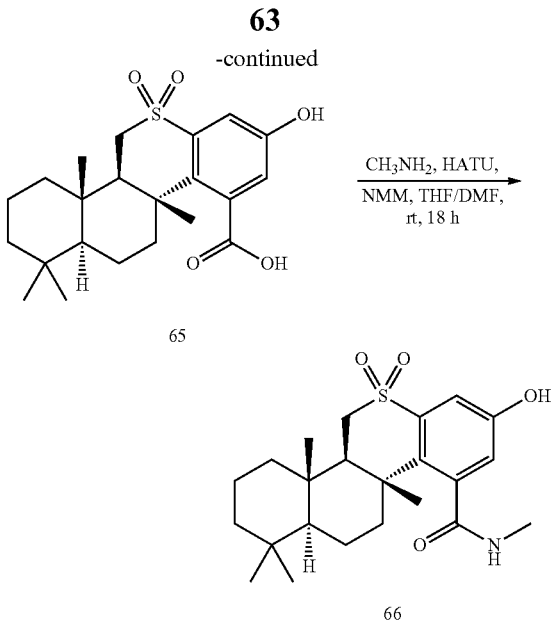

To a solution of (1R,10R,11S,16S)-3,5-dihydroxy-1,11,15,15-tetramethyl-8λ⁶-thiatetracyclo[8.8.0.0²,⁷.0¹¹,¹⁶]octadeca-2,4,6-triene-8,8-dione (28) (8.0 g, 21 mmol) in CH₂Cl₂ (192 mL) and methanol (64 mL), (trimethylsilyl)diazomethane (2 M in diethyl ether, 16.9 mL, 33.8 mmol) was added in 2 mL increments every hour at room temperature under N₂. The mixture was stirred at room temperature for 18 h. The reaction mixture was concentrated to dryness and the residue was purified by flash chromatography on silica gel (Hexanes/EtOAc, 2:1) to yield (1R,10R,11S,16S)-3-hydroxy-5-methoxy-1,11,15,15-tetramethyl-8λ⁶-thiatetracyclo[8.8.0.0²,⁷.0¹¹,¹⁶]octadeca-2,4,6-triene-8,8-dione (30) (4.9 g, 58%) as a white solid.

To a solution of (1R,10R,11S,16S)-3-hydroxy-5-methoxy-1,11,15,15-tetramethyl-8λ⁶-thiatetracyclo[8.8.0.0²,⁷.0¹¹,¹⁶]octadeca-2,4,6-triene-8,8-dione (30) (5.2 g, 13 mmol) in CH₂Cl₂ (200 mL), triethylamine (1.7 mL, 20 mmol) was added followed by trifluoromethanesulfonic anhydride (2.1 mL, 16 mmol) at room temperature under N₂. The mixture was stirred at room temperature for 18 h. Additional triethylamine (1.66 mL, 19.7 mmol) and trifluoromethanesulfonic anhydride (2.1 mL, 16 mmol) were added and stirring continued at room temperature for 48 h. The reaction was concentrated to dryness. The residue was purified by flash chromatography on silica gel (Hexanes/EtOAc, 3:1) to yield (1R,10S,11S,16S)-5-methoxy-11,15,15-trimethyl-8,8-dioxo-8λ⁶-thiatetracyclo[8.8.0.0²,⁷.0¹¹,¹⁶]octadeca-2,4,6-trien-3-yl trifluoromethanesulfonate (63) (5.8 g, 84%) as a white solid.

In a steel bomb (1R,10S,11S,16S)-5-methoxy-11,15,15-trimethyl-8,8-dioxo-8λ⁶-thiatetracyclo[8.8.0.0²,⁷.0¹¹,¹⁶]octadeca-2,4,6-trien-3-yl trifluoromethanesulfonate (63) (5.8 g, 11 mmol), 2,6-lutidine (3.1 mL, 25 mmol), Pd(OAc)₂ (0.3 g, 1 mmol), dppf (0.72 g, 1.1 mmol) and anhydrous methanol (150 mL) were placed. The bomb was sealed and subjected to carbon monoxide at 200 psi with stirring at 80° C. for 18 h. The reaction mixture was cooled to room temperature, filtered through a Celite pad and the filtrate was concentrated to dryness. The crude product was purified by flash chromatography on silica gel (Hexanes/EtOAc, 2:1) to yield (1R,10S,11S,16S)-5-methoxy-11,15,15-trimethyl-8,8-dioxo-8λ⁶-thiatetracyclo[8.8.0.0²,⁷.0¹¹,¹⁶]octadeca-2,4,6-triene-3-carboxylate (64) (4.8 g, 99%) as a white solid.

A mixture of lithium hydride (0.88 g, 110 mmol), 1-propanethiol (11.7 mL, 133 mmol) in HMPA (20 mL) was prepared under N₂. The mixture was stirred at room temperature for 30 min. To the mixture, (1R,10S,11S,16S)-5-methoxy-11,15,15-trimethyl-8,8-dioxo-8λ⁶-thiatetracyclo[8.8.0.0²,⁷.0¹¹,¹⁶]octadeca-2,4,6-triene-3-carboxylate (64) (4.8 g, 11 mmol) in HMPA (10 mL) was added. The mixture was heated at 130° C. for 1 h. The mixture was cooled to room temperature and quenched with 1 M HCl, then extracted with EtOAc. The organic layer was concentrated to dryness. The crude product was purified by flash chromatography on silica gel (CH₂Cl₂/MeOH, 10:1) to yield (1R,10R,11S,16S)-5-hydroxy-1,11,15,15-tetramethyl-8,8-dioxo-8λ⁶-thiatetracyclo[8.8.0.0²,⁷.0¹¹,¹⁶]-octadeca-2,4,6-triene-3-carboxylic acid (65) (4.2 g, 93%) as a white solid. ¹H NMR (CD₃OD): δ 7.18 (s, 1H), 6.88 (s, 1H), 3.45 (m, 1H), 2.83 (m, 1H), 2.10 (d, 1H), 1.82-1.35 (m, 10H), 1.20 (m, 2H) 1.00 (m, 5H), 0.89 (s, 3H), 0.85 (s, 3H). MS m/z 405 (C₂₂H₃₀NO₅S–H⁺).

A mixture of (1R,10R,11S,16S)-5-hydroxy-1,11,15,15-tetramethyl-8,8-dioxo-8λ⁶-thiatetracyclo[8.8.0.0²,⁷.0¹¹,¹⁶]octadeca-2,4,6-triene-3-carboxylic acid (65) (0.49 g, 1.2 mmol), HATU (0.70 g, 1.8 mmol), N-methyl morpholine (0.40 mL, 3.6 mmol), methylamine (2 M in THF, 3.0 mL, 6.0 mmol), THF (10 mL) and DMF (2.0 mL) were placed in a sealed tube. The mixture was stirred at room temperature for 18 h. The THF was evaporated and the residue was quenched with water. The resulting solid was collected by filtration. The crude product was purified by flash chromatography on silica gel (Hexanes/EtOAc, 1:1) to yield (1R,10R,11S,16S)-5-hydroxy-N,1,11,15,15-pentamethyl-8,8-dioxo-8λ⁶-thiatetracyclo[8.8.0.0²,⁷.0¹¹,¹⁶]octadeca-2,4,6-triene-3-carboxamide (66) (0.25 g, 44%) as a white solid. ¹H NMR (CDCl₃): δ 7.62 (s, 1H), 7.09 (s, 1H), 6.70 (s, 1H), 6.36 (m, 1H), 3.39 (m, 2H), 2.97 (d, 3H), 2.54 (m, 1H), 2.13 (m, 1H), 1.75-0.96 (m, 13H), 0.94 (s, 3H), 0.88 (s, 3H), 0.82 (s, 3H). MS m/z 420 (C₂₃H₃₃NO₄S+H⁺).

Example 33

Synthesis of (1R,10R,11S,16S)-5-hydroxy-N,1,11,15,15-pentamethyl-8,8-dioxo-8Λ⁶-thiatetracyclo[8.8.0.0²,⁷.0¹¹,¹⁶]octadeca-2,4,6-triene-4-carboxamide

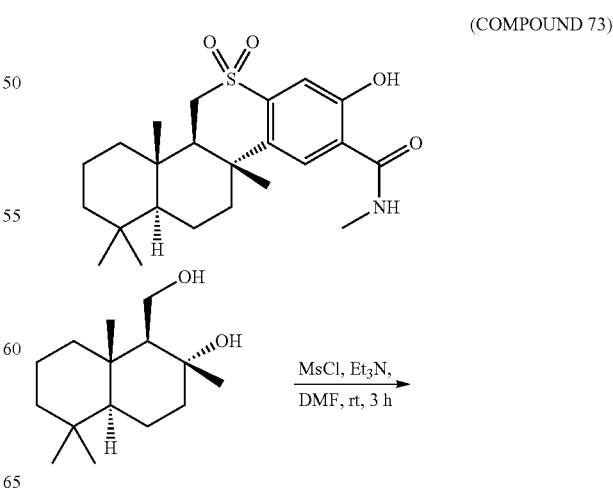

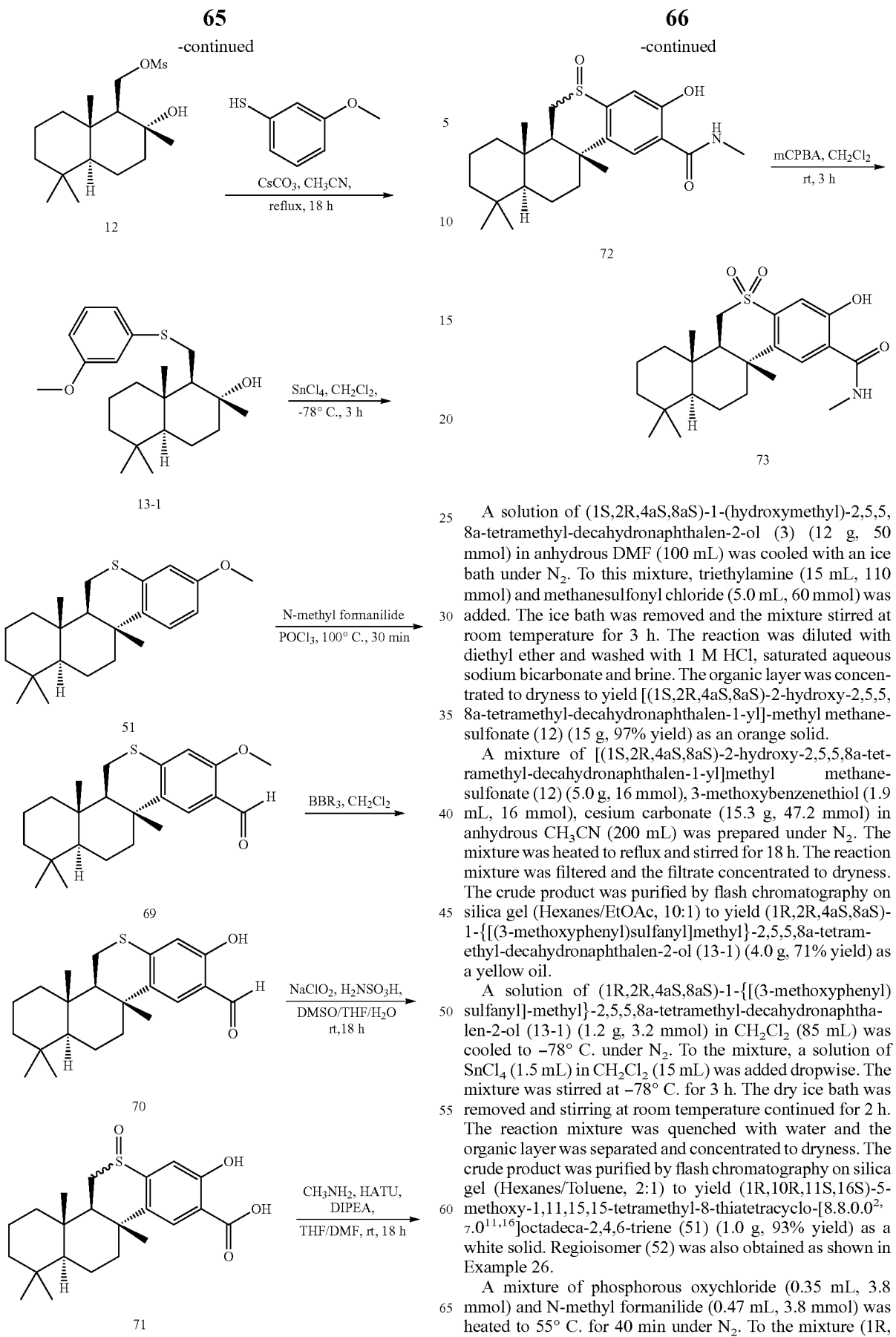

A solution of (1S,2R,4aS,8aS)-1-(hydroxymethyl)-2,5,5,8a-tetramethyl-decahydronaphthalen-2-ol (3) (12 g, 50 mmol) in anhydrous DMF (100 mL) was cooled with an ice bath under $N_2$. To this mixture, triethylamine (15 mL, 110 mmol) and methanesulfonyl chloride (5.0 mL, 60 mmol) was added. The ice bath was removed and the mixture stirred at room temperature for 3 h. The reaction was diluted with diethyl ether and washed with 1 M HCl, saturated aqueous sodium bicarbonate and brine. The organic layer was concentrated to dryness to yield [(1S,2R,4aS,8aS)-2-hydroxy-2,5,5,8a-tetramethyl-decahydronaphthalen-1-yl]-methyl methanesulfonate (12) (15 g, 97% yield) as an orange solid.

A mixture of [(1S,2R,4aS,8aS)-2-hydroxy-2,5,5,8a-tetramethyl-decahydronaphthalen-1-yl]methyl methanesulfonate (12) (5.0 g, 16 mmol), 3-methoxybenzenethiol (1.9 mL, 16 mmol), cesium carbonate (15.3 g, 47.2 mmol) in anhydrous $CH_3CN$ (200 mL) was prepared under $N_2$. The mixture was heated to reflux and stirred for 18 h. The reaction mixture was filtered and the filtrate concentrated to dryness. The crude product was purified by flash chromatography on silica gel (Hexanes/EtOAc, 10:1) to yield (1R,2R,4aS,8aS)-1-{[(3-methoxyphenyl)sulfanyl]methyl}-2,5,5,8a-tetramethyl-decahydronaphthalen-2-ol (13-1) (4.0 g, 71% yield) as a yellow oil.

A solution of (1R,2R,4aS,8aS)-1-{[(3-methoxyphenyl)sulfanyl]-methyl}-2,5,5,8a-tetramethyl-decahydronaphthalen-2-ol (13-1) (1.2 g, 3.2 mmol) in $CH_2Cl_2$ (85 mL) was cooled to −78° C. under $N_2$. To the mixture, a solution of $SnCl_4$ (1.5 mL) in $CH_2Cl_2$ (15 mL) was added dropwise. The mixture was stirred at −78° C. for 3 h. The dry ice bath was removed and stirring at room temperature continued for 2 h. The reaction mixture was quenched with water and the organic layer was separated and concentrated to dryness. The crude product was purified by flash chromatography on silica gel (Hexanes/Toluene, 2:1) to yield (1R,10R,11S,16S)-5-methoxy-1,11,15,15-tetramethyl-8-thiatetracyclo-[8.8.0.0$^{2,7}$.0$^{11,16}$]octadeca-2,4,6-triene (51) (1.0 g, 93% yield) as a white solid. Regioisomer (52) was also obtained as shown in Example 26.

A mixture of phosphorous oxychloride (0.35 mL, 3.8 mmol) and N-methyl formanilide (0.47 mL, 3.8 mmol) was heated to 55° C. for 40 min under $N_2$. To the mixture (1R,10R,11S,16S)-5-methoxy-1,11,15,15-tetramethyl-8 thiatetracyclo[8.8.0.0$^{2,7}$.0$^{11,16}$]octadeca-2,4,6-triene (4) (0.6 g, 2 mmol) was added, the temperature was elevated to 100° C. and stirring continued for 30 min. The reaction mixture was cooled to room temperature and quenched with water. The resulting solid was collected by filtration to yield (1R,10R, 11S,16S)-5-methoxy-1,11,15,15-tetramethyl-8-thiatetracyclo[8.8.0.0$^{2,7}$.0$^{11,16}$]octadeca-2,4,6-triene-4-carbaldehyde (69) (0.62 g, 95%) as a white solid.

A solution of (1R,10R,11S,16S)-5-methoxy-1,11,15,15-tetramethyl-8-thiatetracyclo[8.8.0.0$^{2,7}$.0$^{11,16}$]octadeca-2,4,6-triene-4-carbaldehyde (69) (0.62 g, 1.7 mmol) in CH$_2$Cl$_2$ (30 mL) was prepared at 0° C. under N$_2$. To the mixture, BBr$_3$ (1 M in CH$_2$Cl$_2$, 6.6 mL, 6.6 mmol) was added dropwise. The mixture was stirred at 0° C. for 30 min and then concentrated. The residue was dissolved in EtOAc and washed with water. The organic layer was concentrated to dryness. The crude product was purified by flash chromatography on silica gel (Hexanes/EtOAc, 10:1) to yield (1R,10R,11S,16S)-5-hydroxy-1,11,15,15-tetramethyl-8-thiatetracyclo[8.8.0.0$^{2,7}$.0$^{11,16}$]octadeca-2,4,6-triene-4-carbaldehyde (70) (0.48 g, 80%) as a white solid.

A solution of (1R,10R,11S,16S)-5-hydroxy-1,11,15,15-tetramethyl-8-thiatetracyclo[8.8.0.0$^{2,7}$.0$^{11,16}$]octadeca-2,4,6-triene-4-carbaldehyde (70) (0.30 g, 0.84 mmol) in THF (5.0 mL) and DMSO (5.0 mL) was prepared. To the mixture, sulfamic acid (0.85 g, 8.9 mmol) and a solution of NaClO$_2$ (0.93 g, 8.4 mmol) in water (15 mL) was added. The mixture was stirred at room temperature for 18 h. The reaction mixture was quenched with 1 M HCl and extracted with EtOAc. The organic layer was separated and concentrated to dryness. The residue yielded (1R,10R,11S,16S)-5-hydroxy-1,11,15,15-tetramethyl-8-oxo-8λ$^4$-thiatetracyclo-[8.8.0.0$^{2,7}$.0$^{11,16}$]octadeca-2,4,6-triene-4-carboxylic acid (71) (0.40 g) which was used in the subsequent reaction without further purification.

A mixture of (1R,10R,11S,16S)-5-hydroxy-1,11,15,15-tetramethyl-8-oxo-8λ$^4$-thiatetracyclo[8.8.0.0$^{2,7}$.0$^{11,16}$]octadeca-2,4,6-triene-4-carboxylic acid (71) (0.40 g, 1.1 mmol), HATU (0.49 g, 1.3 mmol), Hunig's base (0.24 mL, 1.4 mmol), methylamine (2 M in diethyl ether, 2.7 mL, 5.4 mmol) in anhydrous THF (10 mL) and DMF (2 mL) was placed in a sealed vessel. The reaction was stirred at room temperature for 18 h. The reaction was diluted with EtOAc and washed with water and brine. The organic layer was separated and concentrated to dryness. The crude product was purified by flash chromatography on silica gel (CH$_2$Cl$_2$/EtOAc, 7:3) to yield (1R,10R,11S,16S)-5-hydroxy-N,1,11,15,15-pentamethyl-8-oxo-8λ$^4$-thiatetracyclo[8.8.0.0$^{2,7}$.0$^{11,16}$]octadeca-2,4,6-triene-4-carboxamide (72) (0.07 g, 16% yield) as a white solid.

A solution of (1R,10R,11S,16S)-5-hydroxy-N,1,11,15,15-pentamethyl-8-oxo-8λ$^4$-thiatetracyclo[8.8.0.0$^{2,7}$.0$^{11,16}$]octadeca-2,4,6-triene-4-carboxamide (72) (0.07 g, 0.2 mmol) in anhydrous CH$_2$Cl$_2$ (10 mL) was prepared at room temperature. To the mixture m-CPBA (0.06 g, 0.3 mmol) was added and the mixture was stirred for 3 h. The reaction mixture was quenched with saturated aqueous sodium bicarbonate and the organic layer was separated and concentrated to dryness. The crude product was purified by flash chromatography on silica gel (CH$_2$Cl$_2$/MeOH, 10:1) to yield (1R,10R,11S,16S)-5-hydroxy-N,1,11,15,15-pentamethyl-8,8-dioxo-8λ$^6$-thiatetracyclo[8.8.0.0$^{2,7}$.0$^{11,16}$]octadeca-2,4,6-triene-4-carboxamide (73) (0.043 g, 59%) as a white solid. $^1$H NMR (CDCl$_3$): δ 11.98 (s, 1H), 7.43 (s, 1H), 7.35 (s, 1H), 6.35 (s, 1H), 3.38 (m, 2H), 3.05 (d, 3H), 2.45 (d, 1H), 2.23 (d, 1H), 1.81-0.97 (m, 13H), 0.95 (s, 3H), 0.88 (s, 3H), 0.85 (s, 3H). MS m/z 418 (C$_{23}$H$_{33}$NO$_4$S−H$^+$).

Example 34

Synthesis of (1R,10R,11S,16S)-5-hydroxy-N,1,11,15,15-pentamethyl-8-thiatetracyclo[8.8.0.0$^{2,7}$.0$^{11,16}$]octadeca-2,4,6-triene-3-carboxamide

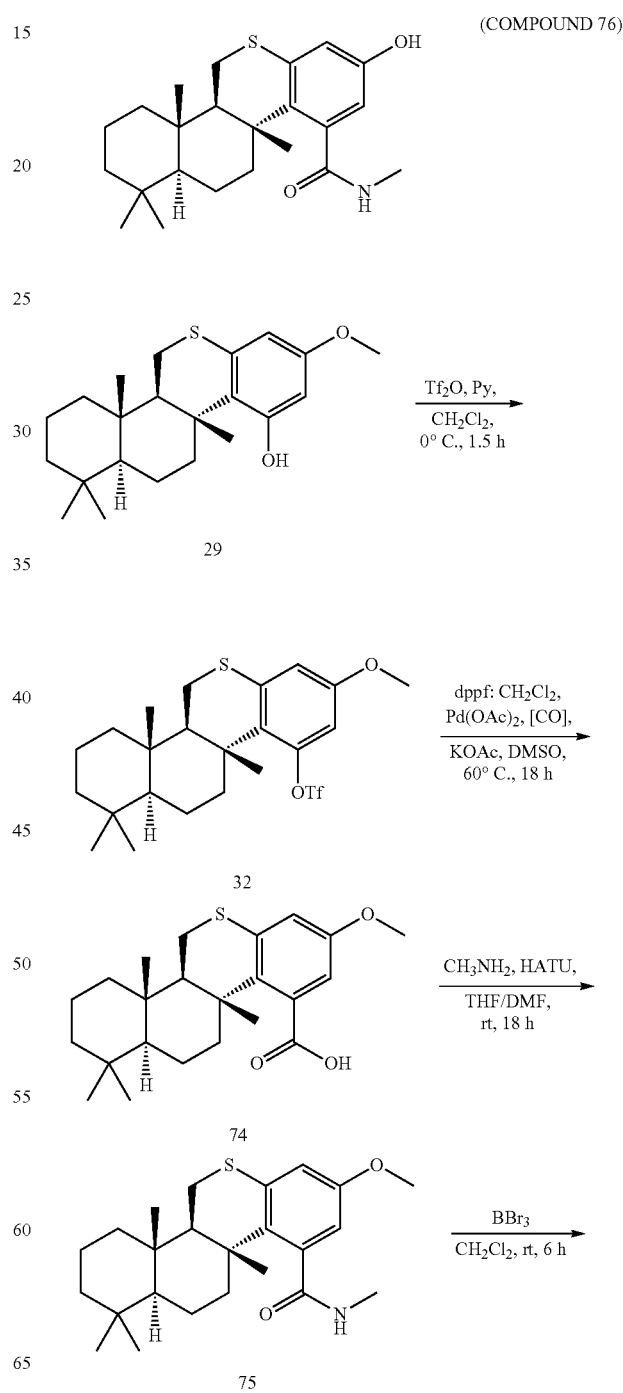

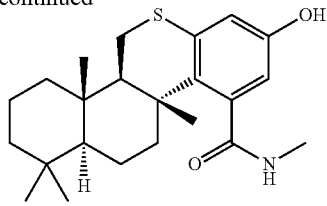
76

A solution of (1R,10R,11S,16S)-5-methoxy-1,11,15,15-tetramethyl-8-thiatetracyclo[8.8.0.0$^{2,7}$.0$^{11,16}$]octadeca-2,4,6-trien-3-ol (29) (1.1 g, 3.1 mmol) in CH$_2$Cl$_2$ (30 mL) was cooled with an ice bath under N$_2$. To the mixture pyridine (0.37 mL, 4.6 mmol) and trifluoromethanesulfonic anhydride (0.67 mL, 4.0 mmol) was added. The mixture was stirred at 0° C. for 1.5 h. The reaction mixture was quenched with water, and the organic layer was separated and concentrated to dryness to yield (1R,10R,11S,16S)-5-methoxy-1,11,15,15-tetramethyl-8-thiatetracyclo[8.8.0.0$^{2,7}$.0$^{11,16}$]octadeca-2,4,6-trien-3-yl trifluoromethanesulfonate (32) (1.46 g, 97%) as a brown solid.

A mixture of (1R,10R,11S,16S)-5-methoxy-1,11,15,15-tetramethyl-8-thiatetracyclo[8.8.0.0$^{2,7}$.0$^{11,16}$]octadeca-2,4,6-trien-3-yl trifluoromethanesulfonate (32) (1.5 g, 3.0 mmol), KOAc (1.1 g, 12 mmol), Pd(OAc)$_2$ (0.3 g, 2 mmol), dppf:CH$_2$Cl$_2$ 1:1 (0.97 g, 1.3 mmol) was prepared in DMSO (15 mL) and purged with N$_2$. The reaction mixture was subjected to carbon monoxide via a balloon. The mixture was stirred at 60° C. for 18 h. The reaction was cooled to room temperature and quenched with water, acidified with 1 M HCl and extracted with EtOAc. The organic layer was concentrated to dryness. The crude product was purified by flash chromatography on silica gel (CH$_2$Cl$_2$/EtOAc, 1:1) to yield (1R,10R,11S,16S)-5-methoxy-1,11,15,15-tetramethyl-8-thiatetracyclo[8.8.0.0$^{2,7}$.0$^{11,16}$]octadeca-2,4,6-triene-3-carboxylic acid (74) (0.40 g, 34%) as a brown solid.

A solution of (1R,10R,11S,16S)-5-methoxy-1,11,15,15-tetramethyl-8-thiatetracyclo[8.8.0.0$^{2,7}$.0$^{11,16}$]octadeca-2,4,6-triene-3-carboxylic acid (74) (0.13 g, 0.33 mmol) in anhydrous THF (10 mL) and anhydrous DMF (0.7 mL), was prepared under N$_2$. To the solution, HATU (0.15 g, 0.40 mmol) and Hunig's base (0.08 mL, 0.4 mmol) were added. The mixture was stirred at room temperature for 1 h. MeNH$_2$ (2 M in THF, 2.0 mL, 4.0 mmol) was added and the flask was sealed and stirred at room temperature for 24 h. The reaction mixture was concentrated, and the residue was dissolved in CH$_2$Cl$_2$ and washed with saturated aqueous sodium bicarbonate. The aqueous phase was extracted with CH$_2$Cl$_2$. The combined organic extracts were washed with brine and concentrated to dryness. The crude product was purified by flash chromatography on silica gel (CH$_2$Cl$_2$/EtOAc, 5:1) to yield (1R,10R,11S,16S)-5-methoxy-N,1,11,15,15-pentamethyl-8-thiatetracyclo[8.8.0.0$^{2,7}$.0$^{11,16}$]octadeca-2,4,6-triene-3-carboxamide (75) (0.08 g, 59%) as a white solid.

A solution of (1R,10R,11S,16S)-5-methoxy-N,1,11,15,15-pentamethyl-8-thiatetracyclo[8.8.0.0$^{2,7}$.0$^{11,16}$]octadeca-2,4,6-triene-3-carboxamide (75) (0.17 g, 0.42 mmol) in anhydrous CH$_2$Cl$_2$ (5.0 mL) was cooled with an ice bath under N$_2$. To the mixture BBr$_3$ (1 M in CH$_2$Cl$_2$, 1.6 mL, 1.6 mmol) was added dropwise. The mixture was stirred at 0° C. for 2.5 h then at room temperature for 3.25 h. The solution was cooled to 0° C. and quenched with anhydrous MeOH. The solution was evaporated and the residue co-evaporated with anhydrous MeOH. The solid was suspended in EtOAc and washed with 0.09 M HCl (11 mL). The mixture was taken to pH=7.5 using sodium bicarbonate. The organic layer was separated was concentrated to dryness. The crude material was triturated with MeOH then filtered and washed with MeOH to yield (1R,10R,11S,16S)-5-hydroxy-N,1,11,15,15-pentamethyl-8-thiatetracyclo-[8.8.0.0$^{2,7}$.0$^{11,16}$]octadeca-2,4,6-triene-3-carboxamide (76) (0.09 g, 57%) as a white solid. $^1$H NMR (DMSO-d$_6$): δ 9.37 (s, 1H), 8.10 (m, 1H), 6.36 (d, 1H), 6.18 (d, 1H), 2.94 (dd, 1H), 2.80 (d, 1H), 2.65 (d, 3H), 1.81 (d, 1H), 1.62-1.26 (m, 12H), 1.09 (ddd, 1H), 0.87-0.81 (m, 7H), 0.78 (s, 3H). MS m/z 388 (C$_{23}$H$_{33}$NO$_2$S+H$^+$).

Example 35

Synthesis of (1R,10R,11S,16S)-5-hydroxy-1,11,15,15-tetramethyl-8,8-dioxo-8Λ$^6$-thiatetracyclo[8.8.0.0$^{2,7}$.0$^{11,16}$]octadeca-2,4,6-triene-3-carbonitrile (COMPOUND 79)

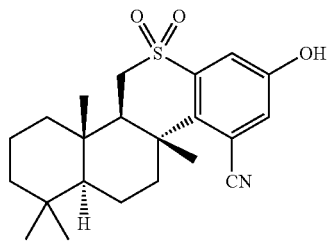

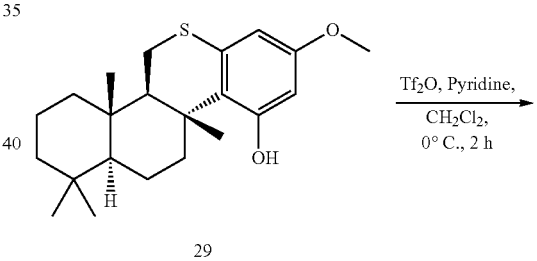

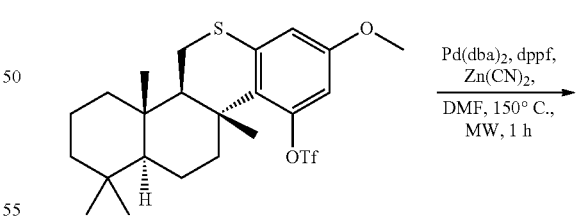

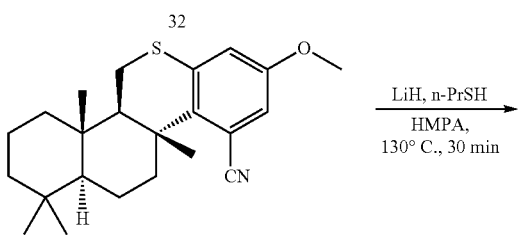

77

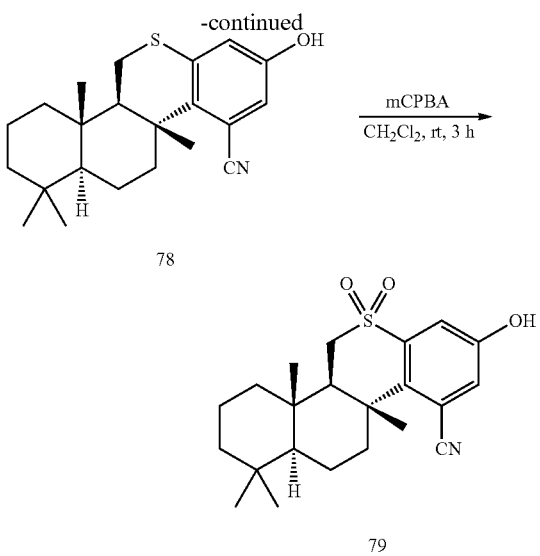

78

79

A solution of (1R,10R,11S,16S)-5-methoxy-1,11,15,15-tetramethyl-8-thiatetracyclo[8.8.0.0$^{2,7}$.0$^{11,16}$]octadeca-2,4,6-trien-3-ol (29) (0.29 g, 0.80 mmol) in anhydrous CH$_2$Cl$_2$ (10 mL) was cooled with an ice bath under N$_2$. To the mixture pyridine (0.10 mL, 1.2 mmol) and trifluoromethanesulfonic anhydride (0.20 mL, 1.2 mmol) were added. The mixture was stirred at 0° C. for 2 h. The reaction was quenched with water and the organic layer was separated and concentrated to dryness to give (1R,10R,11S,16S)-5-methoxy-1,11,15,15-tetramethyl-8-thiatetracyclo[8.8.0.0$^{2,7}$.0$^{11,16}$]octadeca-2,4,6-trien-3-yl trifluoromethanesulfonate (32) (0.39 g, 100%) as an orange solid.

A mixture of (1R,10R,11S,16S)-5-methoxy-1,11,15,15-tetramethyl-8-thiatetracyclo[8.8.0.0$^{2,7}$.0$^{11,16}$]octadeca-2,4,6-trien-3-yl trifluoromethanesulfonate (32) (0.20 g, 0.40 mmol), Pd(dba)$_2$ (0.037 g, 0.11 mmol), dppf (0.09 g, 0.2 mmol), Zn(CN)$_2$ (0.057 g, 0.48 mmol) in anhydrous DMF (5.0 mL) was placed in a microwave tube. The vessel was heated at 150° C. and 10 psi for 1 h. The reaction was cooled to room temperature, diluted with EtOAc and washed with water. The organic layer was concentrated to dryness. The crude product was purified by flash chromatography on silica gel (Hexanes/EtOAc, 10:1) to yield (1R,10R,11S,16S)-5-methoxy-1,11,15,15-tetramethyl-8-thiatetracyclo[8.8.0.0$^{2,7}$.0$^{11,16}$]octadeca-2,4,6-triene-3-carbonitrile (77) (0.10 g, 67%) as a white solid.

A mixture of LiH (0.127 g, 16.2 mmol), 1-propyl thiol (1.60 mL, 17.6 mmol) in HMPA (2 mL) was stirred at room temperature for 15 minutes under N$_2$. To the mixture, a solution of (1R,10R,11S,16S)-5-methoxy-1,11,15,15-tetramethyl-8-thiatetracyclo[8.8.0.0$^{2,7}$.0$^{11,16}$]octadeca-2,4,6-triene-3-carbonitrile (77) (0.10 g 0.27 mmol) in HMPA (3.0 mL) was added. The mixture was heated at 130° C. for 30 min. The reaction mixture was cooled to room temperature and quenched with water, then extracted with EtOAc. The organic layer was separated and concentrated to dryness. The crude product was purified by flash chromatography on silica gel (Hexanes/EtOAc, 10:1) to yield (1R,10R,11S,16S)-5-hydroxy-1,11,15,15-tetramethyl-8-thiatetracyclo[8.8.0.0$^{2,7}$.0$^{11,16}$]octadeca-2,4,6-triene-3-carbonitrile (78) (0.06 g, 62%) as a white solid. $^1$H NMR (CDCl$_3$): δ 6.86 (d, 1H), 6.72 (d, 1H), 4.72 (s, 1H), 3.47 (m, 1H), 2.86 (m, 2H), 1.86-1.56 (m, 4H), 1.52-1.36 (m, 6H), 1.28-0.97 (m, 3H), 0.94 (s, 3H), 0.90 (m, 1H), 0.87 (s, 3H), 0.84 (s, 3H). MS m/z 354 (C$_{22}$H$_{29}$NOS–H$^+$).

A solution of (1R,10R,11S,16S)-5-hydroxy-1,11,15,15-tetramethyl-8-thiatetracyclo[8.8.0.0$^{2,7}$.0$^{11,16}$]octadeca-2,4,6-triene-3-carbonitrile (78) (0.045 g, 0.13 mmol) in anhydrous CH$_2$Cl$_2$ (20 mL) was prepared. To the mixture, 3-choroperoxybenzoic acid (0.063 g, 0.28 mmol) was added. The mixture was stirred at room temperature for 3 h. The reaction was concentrated to dryness. The residue was re-dissolved in EtOAc and washed with saturated aqueous sodium bicarbonate. The organic layer was separated and concentrated to dryness. The crude product was purified by flash chromatography on silica gel (Hexanes/EtOAc, 6:1) to yield (1R,10R,11S,16S)-5-hydroxy-1,11,15,15-tetramethyl-8,8-dioxo-8λ$^6$-thiatetracyclo[8.8.0.0$^{2,7}$.0$^{11,16}$]octadeca-2,4,6-triene-3-carbonitrile (79) (0.017 g, 35%) as a white solid. $^1$H NMR (CDCl$_3$): δ 7.61 (d, 1H), 7.38 (d, 1H), 7.08 (m, 1H), 3.47 (m, 2H), 3.28 (t, 1H), 2.28 (d, 1H), 1.84-1.38 (m, 10H), 1.30-0.92 (m, 6H), 0.89 (s, 3H), 0.85 (s, 3H). MS m/z 386 (C$_{22}$H$_{29}$NO$_3$S–H$^+$).

Example 36

Synthesis of (1R,10R,11S,16S)-3-methoxy-N,1,11,15,15-pentamethyl-8,8-dioxo-8Λ$^6$-thiatetracyclo[8.8.0.0$^{2,7}$.0$^{11,16}$]octadeca-2,4,6-triene-5-carboxamide (COMPOUND 81)

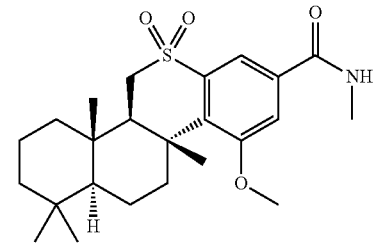

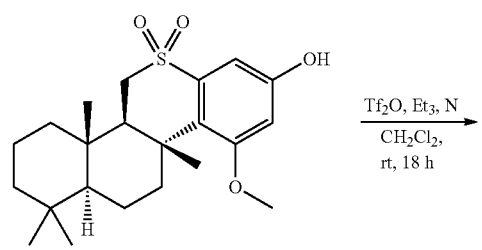

57

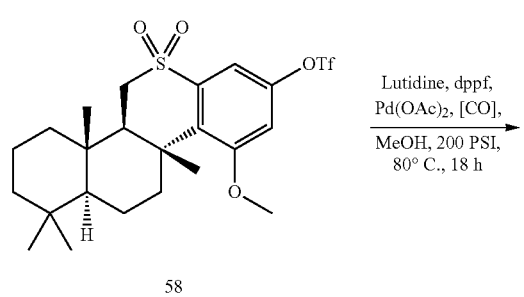

58

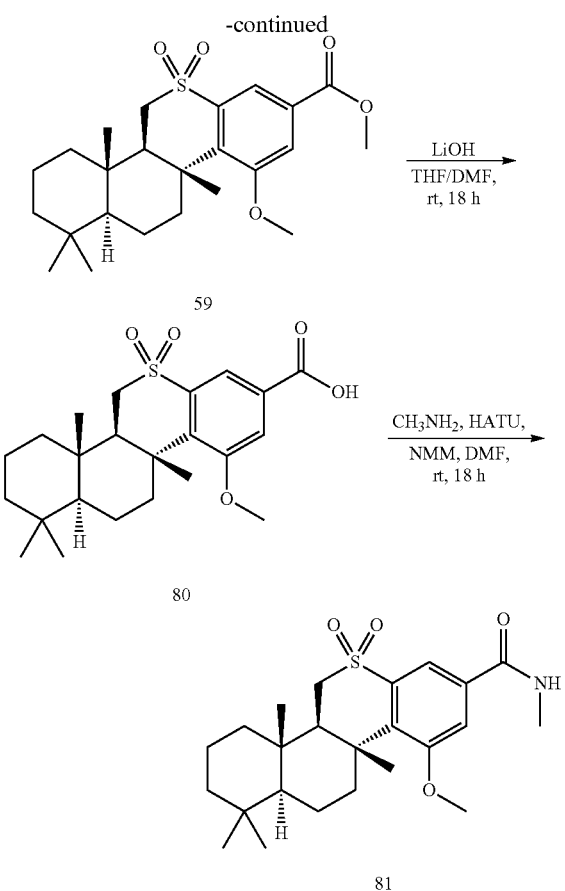

To a stirred solution of (1R,10R,11S,16S)-5-hydroxy-3-methoxy-1,11,15,15-tetramethyl-8λ⁶-thiatetracyclo[8.8.0.0²,⁷.0¹¹,¹⁶]octadeca-2,4,6-triene-8,8-dione (57) (4.7 g, 12 mmol) in CH₂Cl₂ (200 mL) at room temperature, triethylamine (1.5 mL, 18 mmol) was added followed by the addition of trifluoromethanesulfonic anhydride (1.9 mL, 14 mmol). The mixture was stirred at room temperature for 18 h. The reaction mixture was concentrated to dryness under reduced pressure. The residue was purified by flash column chromatography on silica gel (Hexanes/EtOAc, 2:1) to give (1R,10S,11S,16S)-3-methoxy-11,15,15-trimethyl-8,8-dioxo-8λ⁶-thiatetracyclo[8.8.0.0²,⁷.0¹¹,¹⁶]octadeca-2,4,6-trien-5-yl trifluoromethanesulfonate (58) (5.45 g, 87%) as a pale brown solid.

In a steel bomb a mixture of (1R,10S,11S,16S)-3-methoxy-11,15,15-trimethyl-8,8-dioxo-8λ⁶-thiatetracyclo[8.8.0.0²,⁷.0¹¹,¹⁶]octadeca-2,4,6-trien-5-yl trifluoromethanesulfonate (58) (5.45 g, 10.4 mmol), 2,6-lutidine (2.9 mL, 24 mmol), Pd(OAc)₂ (0.28 g, 1.2 mmol) and dppf (0.67 g, 1.2 mmol) in anhydrous methanol (150 mL) was placed. The bomb was sealed and subjected to carbon monoxide at 200 psi with stirring at 80° C. for 18 h. The reaction mixture was cooled to room temperature, filtered through a Celite pad and the filtrate was concentrated to dryness under reduced pressure. The residue was purified by flash column chromatography on silica gel (Hexanes/EtOAc, 2:1) to give (1R,10S,11S,16S)-3-methoxy-11,15,15-trimethyl-8,8-dioxo-8λ⁶-thiatetracyclo-[8.8.0.0²,⁷.0¹¹,¹⁶]octadeca-2,4,6-triene-5-carboxylate (59) (3.6 g, 79%) as a white solid.

A mixture of (1R,10S,11S,16S)-3-methoxy-11,15,15-trimethyl-8,8-dioxo-8λ⁶-thiatetracyclo[8.8.0.0²,⁷.0¹¹,¹⁶]octadeca-2,4,6-triene-5-carboxylate (59) (0.29 g, 0.66 mmol) and LiOH.H₂O (0.08 g, 3.3 mmol) in THF (15 mL) and water (5.0 mL) was stirred at room temperature for 18 h. The mixture was concentrated under reduced pressure and the residue was acidified with 1 M HCl. The resulting solid was collected by filtration to give (1R,10R,11S,16S)-3-methoxy-1,11,15,15-tetramethyl-8,8-dioxo-8λ⁶-thiatetracyclo[8.8.0.0²,⁷.0¹¹,¹⁶]octadeca-2,4,6-triene-5-carboxylic acid (80) (0.27 g, 98%) as a white solid. ¹H NMR (CD₃OD): δ 8.04 (d, 1H), 7.74 (d, 1H), 3.94 (s, 3H), 3.47-3.35 (m, 3H), 2.26 (d, 1H), 1.86-1.16 (m, 11H), 1.10-1.00 (m, 5H), 0.89 (s, 3H), 0.87 (s, 3H). MS m/z 421 (O₂₃H₃₂O₅S+H⁺).

A mixture of (1R,10R,11S,16S)-3-methoxy-1,11,15,15-tetramethyl-8,8-dioxo-8λ⁶-thiatetracyclo[8.8.0.0²,⁷.0¹¹,¹⁶]octadeca-2,4,6-triene-5-carboxylic acid (80) (0.26 g, 0.61 mmol), HATU, (0.36 g, 0.93 mmol), NMM (0.20 mL, 1.9 mmol) and methylamine (2 M in THF, 1.5 mL, 3.0 mmol) in THF (10 mL) and DMF (2.0 mL) was stirred at room temperature for 18 h in a sealed tube. The reaction mixture was concentrated under reduced pressure and the residue was quenched with water. The resulting solid was collected by filtration to give (1R,10R,11S,16S)-3-methoxy-N,1,11,15,15-pentamethyl-8,8-dioxo-8λ⁶-thiatetracyclo[8.8.0.0²,⁷.0¹¹,¹⁶]octadeca-2,4,6-triene-5-carboxamide (81) (0.11 g, 41%) as a white solid. ¹H NMR (CDCl₃): δ 7.67 (d, 1H), 7.61 (d, 1H), 6.27 (s, 1H), 3.91 (s, 3H), 3.40-3.17 (m, 3H), 3.01 (d, 3H), 2.30 (d, 1H), 1.78-1.28 (m, 10H), 1.23-1.00 (m, 3H), 0.97 (s, 3H), 0.87 (s, 3H), 0.84 (s, 3H). MS m/z 434 (C₂₄H₃₅NO₄S+H⁺).

Example 37

Synthesis of (1R,10R,11S,16S)-1,3-N,5-N,11,15,15-hexamethyl-8,8-dioxo-8Λ⁶-thiatetracyclo[8.8.0.0²,⁷.0¹¹,¹⁶]octadeca-2,4,6-triene-3,5-dicarboxamide

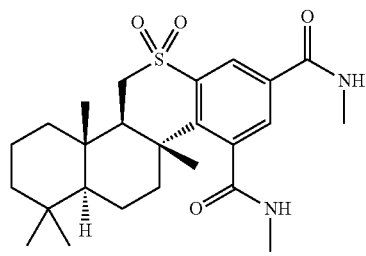

(COMPOUND 86)

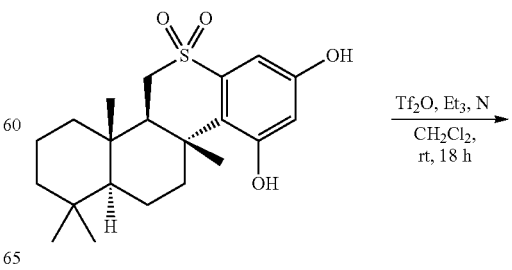

28

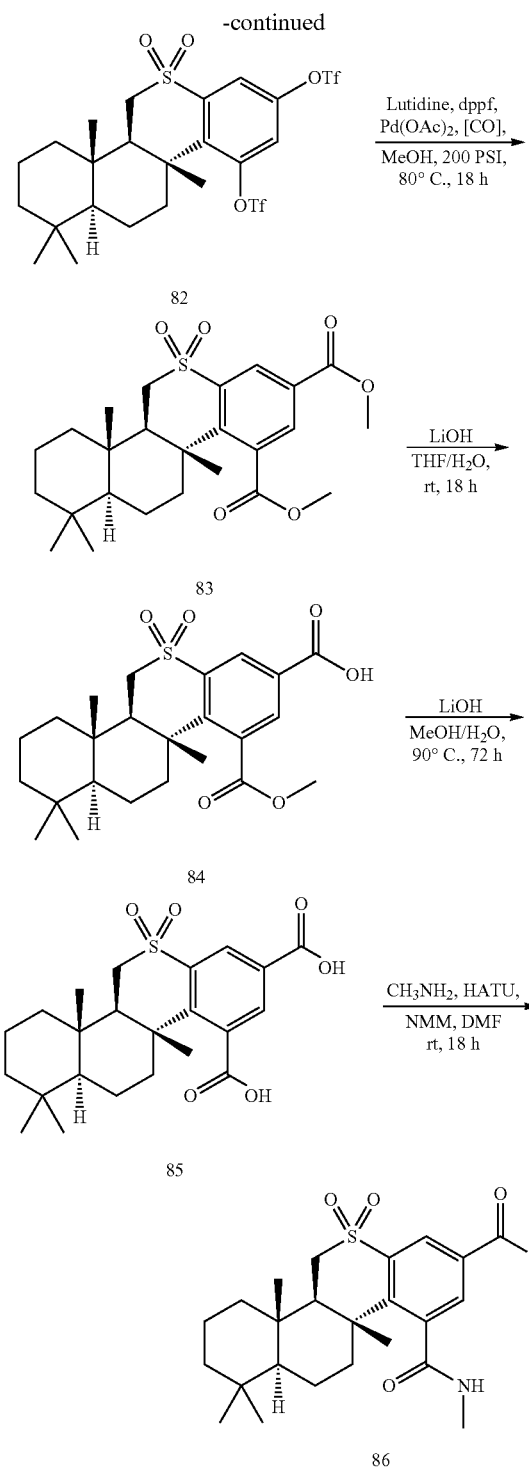

tetramethyl-8,8-dioxo-5-[(trifluoromethane)sulfonyloxy]-8λ$^6$-thiatetracyclo[8.8.0.0$^{2,7}$.0$^{11,16}$]-octadeca-2,4,6-trien-3-yl trifluoromethanesulfonate (82) (1.0 g, 93%) as a creamy solid.

In a steel bomb a mixture of (1R,10R,11S,16S)-1,11,15,15-tetramethyl-8,8-dioxo-5-[(trifluoromethane)sulfonyloxy]-8λ$^6$-thiatetracyclo-[8.8.0.0$^{2,7}$.0$^{11,16}$]octadeca-2,4,6-trien-3-yl trifluoromethanesulfonate (82) (1.0 g, 1.6 mmol), 2,6-lutidine (0.75 mL, 6.2 mmol), Pd(OAc)$_2$ (0.7 g, 0.3 mmol), dppf (0.16 g, 0.28 mmol) in anhydrous MeOH ((150 mL) was placed. The bomb was sealed and subjected to carbon monoxide at 200 psi with stirring at 80° C. for 18 h. The reaction mixture was cooled to room temperature, filtered through a Celite pad and the filtrate was concentrated to dryness under reduced pressure. The residue was purified by flash column chromatography on silica gel (Hexanes/EtOAc, 4:1) to give 3,5-dimethyl (1R,10R,11S,16S)-1,11,15,15-tetramethyl-8,8-dioxo-8λ$^6$-thiatetracyclo[8.8.0.0$^{2,7}$.0$^{11,16}$]octadeca-2,4,6-triene-3,5-dicarboxylate (83) (0.43 g, 60%) as a white solid.

A mixture of 3,5-dimethyl (1R,10R,11S,16S)-1,11,15,15-tetramethyl-8,8-dioxo-8λ$^6$-thiatetracyclo[8.8.0.0$^{2,7}$.0$^{11,16}$] octadeca-2,4,6-triene-3,5-dicarboxylate (83) (0.43 g, 0.93 mmol), LiOH.H$_2$O (0.20 g, 8.4 mmol) in THF (20 mL) and water (10 mL) was stirred at room temperature for 18 h. The reaction was concentrated under reduced pressure and the residue was acidified with 1 M HCl. The resulting solid was collected by filtration to give 3,5-dimethyl (1R,10R,11S,16S)-3-(methoxycarbonyl)-1,11,15,15-tetramethyl-8,8-dioxo-8λ$^6$-thiatetracyclo[8.8.0.0$^{2,7}$.0$^{11,16}$]octadeca-2,4,6-triene-5-carboxylic acid (84) (0.38 g, 91%) as a white solid. $^1$H NMR (CD$_3$OD): δ 8.50 (d, 1H), 8.06 (d, 1H), 3.95 (s, 3H), 3.65-3.55 (m, 2H), 2.44 (m, 1H), 2.18 (d, 1H), 1.89-1.38 (m, 11H), 1.30-1.12 (m, 2H) 1.07-0.96 (m, 5H), 0.90 (s, 3H), 0.87 (s, 3H). MS m/z 447 (C$_{24}$H$_{32}$O$_6$S–H$^+$).

A mixture of (1R,10R,11S,16S)-3-(methoxycarbonyl)-1,11,15,15-tetramethyl-8,8-dioxo-8λ$^6$-thiatetracyclo[8.8.0.0$^{2,7}$.0$^{11,16}$]octadeca-2,4,6-triene-5-carboxylic acid (84) (0.1 g, 0.2 mmol) and LiOH.H$_2$O (0.1 g, 4 mmol) in MeOH (5.0 mL) and water (5.0 mL) was heated at 90° C. for 72 h. The reaction mixture was cooled to room temperature, concentrated under reduced pressure and acidified with 1 M HCl. The resulting solid was collected by filtration to give (1R,10R,11S,16S)-1,11,15,15-tetramethyl-8,8-dioxo-8λ$^6$-thiatetracyclo-[8.8.0.0$^{2,7}$.0$^{11,16}$]octadeca-2,4,6-triene-3,5-dicarboxylic acid (85) (0.09 g, 94%) as a white solid. $^1$H NMR (CD$_3$OD): δ 8.43 (d, 1H), 8.07 (d, 1H), 3.56 (m, 2H), 2.92 (d, 1H), 2.18 (d, 1H), 1.90-1.38 (m, 11H), 1.30-1.17 (m, 2H), 1.08-0.96 (m, 5H), 0.90 (s, 3H), 0.87 (s, 3H). MS m/z 433 (O$_{23}$H$_{30}$O$_6$S–H$^+$).

A mixture of (1R,10R,11S,16S)-1,11,15,15-tetramethyl-8,8-dioxo-8λ$^6$-thiatetracyclo[8.8.0.0$^{2,7}$.0$^{11,16}$]octadeca-2,4,6-triene-3,5-dicarboxylic acid (85) (0.07 g, 0.2 mmol), HATU (0.25 g, 0.65 mmol) and 4-methylmorpholine (0.07 mL, 1 mmol) in THF (10 mL) and DMF (2.0 mL) was stirred at room temperature for 18 h in a sealed vessel. The mixture was concentrated under reduced pressure and the residue was triturated with water. The resulting solid was collected by filtration to give (1R,10R,11S,16S)-1,3-N,5-N,11,15,15-hexamethyl-8,8-dioxo-8λ$^6$-thiatetracyclo[8.8.0.0$^{2,7}$.0$^{11,16}$] octadeca-2,4,6-triene-3,5-dicarboxamide (86) (0.035 g, 47%) as a white solid. $^1$H NMR (CD$_3$OD): δ 8.38 (d, 1H), 7.88 (d, 1H), 3.54 (m, 2H), 2.90 (d, 6H), 2.67 (d, 1H), 2.18 (d, A solution of (1R,10R,11S,16S)-3,5-dihydroxy-1,11,15,15-tetramethyl-8λ$^6$-thiatetracyclo[8.8.0.0$^{2,7}$.0$^{11,16}$]octadeca-2,4,6-triene-8,8-dione (28) (0.63 g, 1.7 mmol) in CH$_2$Cl$_2$ (50 mL) was prepared. To the mixture triethylamine (0.55 mL, 6.7 mmol) was added followed by the addition of trifluoromethanesulfonic anhydride (0.48 mL, 3.7 mmol). The mixture was stirred at room temperature for 18 h and then concentrated to dryness under reduced pressure. The residue was purified by flash column chromatography on silica gel (Hexanes/EtOAc, 2:1) to give (1R,10R,11S,16S)-1,11,15,15-

1H), 1.90-1.48 (m, 9H), 1.46-1.14 (m, 3H), 1.06-0.93 (m, 4H), 0.90 (s, 3H), 0.87 (s, 3H). MS m/z 461 ($C_{25}H_{36}N_2O_4S+ H^+$).

Example 38

Synthesis of (1R,10R,11S,16S)-3-hydroxy-1,11,15,15-tetramethyl-5-[(morpholin-4-yl)carbonyl]-8Λ$^6$-thiatetracyclo[8.8.0.0$^{2,7}$.0$^{11,16}$]octadeca-2,4,6-triene-8,8-dione 7.00 (d, 1H), 3.70-3.24 (m, 10H), 1.90 (d, 1H), 1.83 (d, 1H), 1.70-1.32 (m, 8H), 1.28-1.08 (m, 3H), 0.97 (d, 1H), 0.92 (s, 3H), 0.85 (m, 4H), 0.81 (s, 3H). MS m/z 476 ($C_{26}H_{37}NO_5S+ H^+$).

Example 39

Synthesis of (1R,10R,11S,16S)-3-hydroxy-1,11,15,15-tetramethyl-5-[(morpholin-4-yl)carbonyl]-8Λ$^6$-thiatetracyclo[8.8.0.0$^{2,7}$.0$^{11,16}$]octadeca-2,4,6-triene-8,8-dione

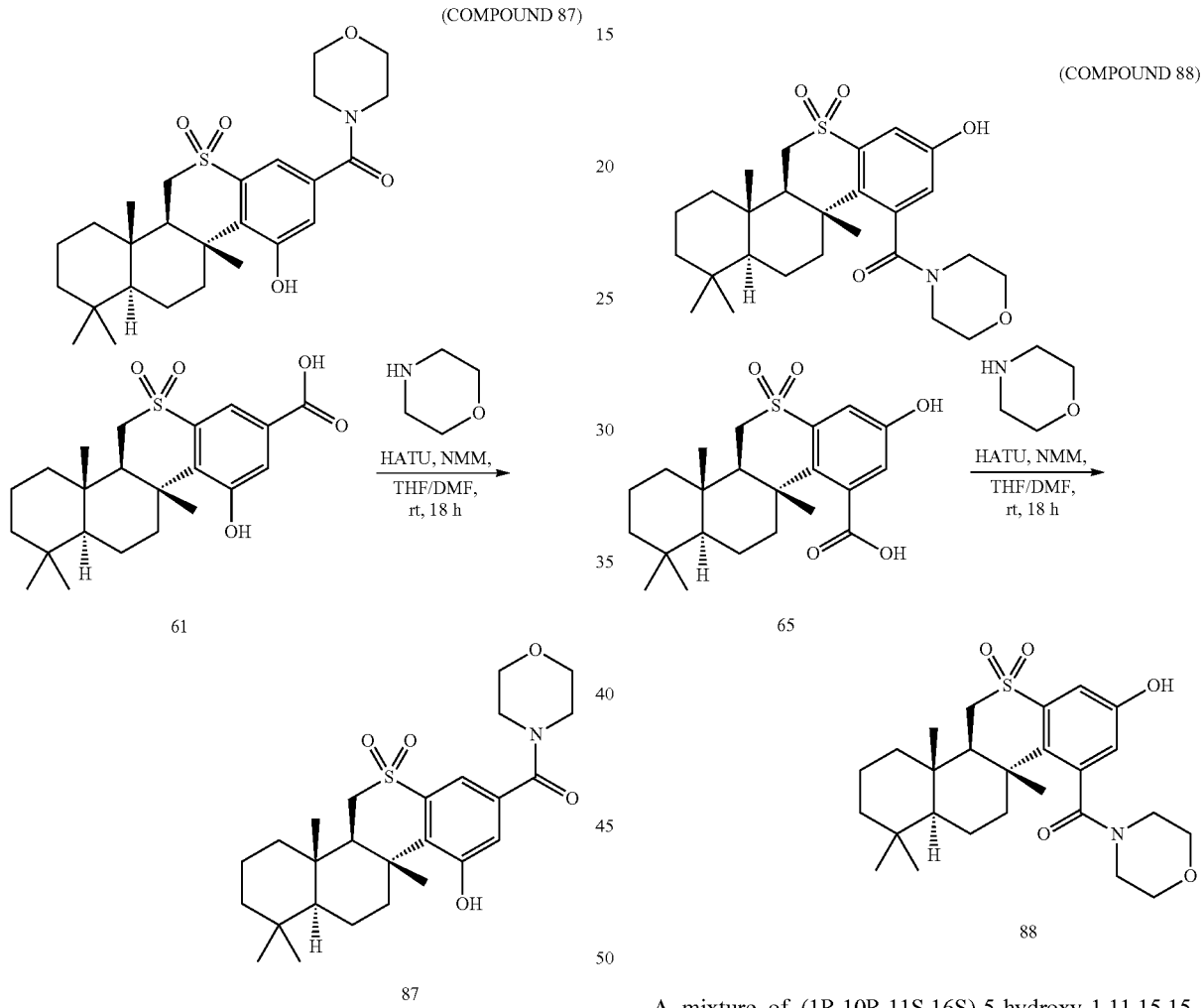

A mixture of (1R,10S,11S,16S)-3-methoxy-11,15,15-trimethyl-8,8-dioxo-8λ$^6$-thiatetracyclo[8.8.0.0$^{2,7}$.0$^{11,16}$]octadeca-2,4,6-triene-5-carboxylic acid (61) (0.08 g, 0.2 mmol), HATU (0.15 g, 0.40 mmol), N-methylmorpholine (0.04 mL, 0.6 mmol) and morpholine (0.086 mL, 1.0 mmol) in THF (4.0 mL) and DMF (1.0 mL) was stirred at room temperature for 18 h. The THF was evaporated under reduced pressure, the residue was quenched with water and the resulting solid was collected by filtration. The crude product was purified by flash column chromatography on silica gel (Hexanes/EtOAc, 3:1) to give (1R,10R,11S,16S)-3-hydroxy-1,11,15,15-tetramethyl-5-[(morpholin-4-yl)-carbonyl]-8λ$^6$-thiatetracyclo[8.8.0.0$^{2,7}$.0$^{11,16}$]-octadeca-2,4,6-triene-8,8-dione (87) (0.05 g, 54%) as a white solid. $^1$H NMR (DMSO-d$_6$): δ 7.18 (d, 1H), A mixture of (1R,10R,11S,16S)-5-hydroxy-1,11,15,15-tetramethyl-8,8-dioxo-8λ$^6$-thiatetracyclo[8.8.0.0$^{2,7}$.0$^{11,16}$]octadeca-2,4,6-triene-3-carboxylic acid (65) (0.06 g, 0.2 mmol), HATU (0.15 g, 0.40 mmol), N-methylmorpholine (0.04 mL, 0.6 mmol) and morpholine (0.1 mL, 1 mmol) in THF (4.0 mL) and DMF (1.0 mL) was stirred at room temperature for 18 h. The THF was evaporated under reduced pressure, the residue was quenched with water and the resulting solid was collected by filtration. The crude product was purified by flash column chromatography on silica gel (Hexanes/EtOAc, 3:1) to give (1R,10R,11S,16S)-5-hydroxy-1,11,15,15-tetramethyl-3-[(morpholin-4-yl)carbonyl]-8λ$^6$-thiatetracyclo-[8.8.0.0$^{2,7}$.0$^{11,16}$]octadeca-2,4,6-triene-8,8-dione (88) (0.05 g, 45%) as a tan solid. $^1$H NMR (DMSO-d$_6$): δ 8.49 (s, 1H), 7.14 (s, 1H), 6.75 (s, 1H), 3.72-3.14 (m, 10H), 2.44 (m, 1H), 2.00 (d, 1H), 1.83 (d, 1H), 1.70-1.32 (m, 8H), 1.28-1.22 (m, 1H), 1.12 (m, 1H), 0.96 (m, 1H), 0.89 (s, 3H), 0.86 (m, 3H), 0.82 (m, 1H), 0.79 (s, 3H). MS m/z 476 ($C_{26}H_{37}NO_6S+H^+$).

Example 40

Synthesis of (1R,10R,11S,16S)-3-hydroxy-1,11,15,15-tetramethyl-5-[(4-methylpiperazin-1-yl)carbonyl]-8λ⁶-thiatetracyclo[8.8.0.0²,⁷.0¹¹,¹⁶]octadeca-2,4,6-triene-8,8-dione

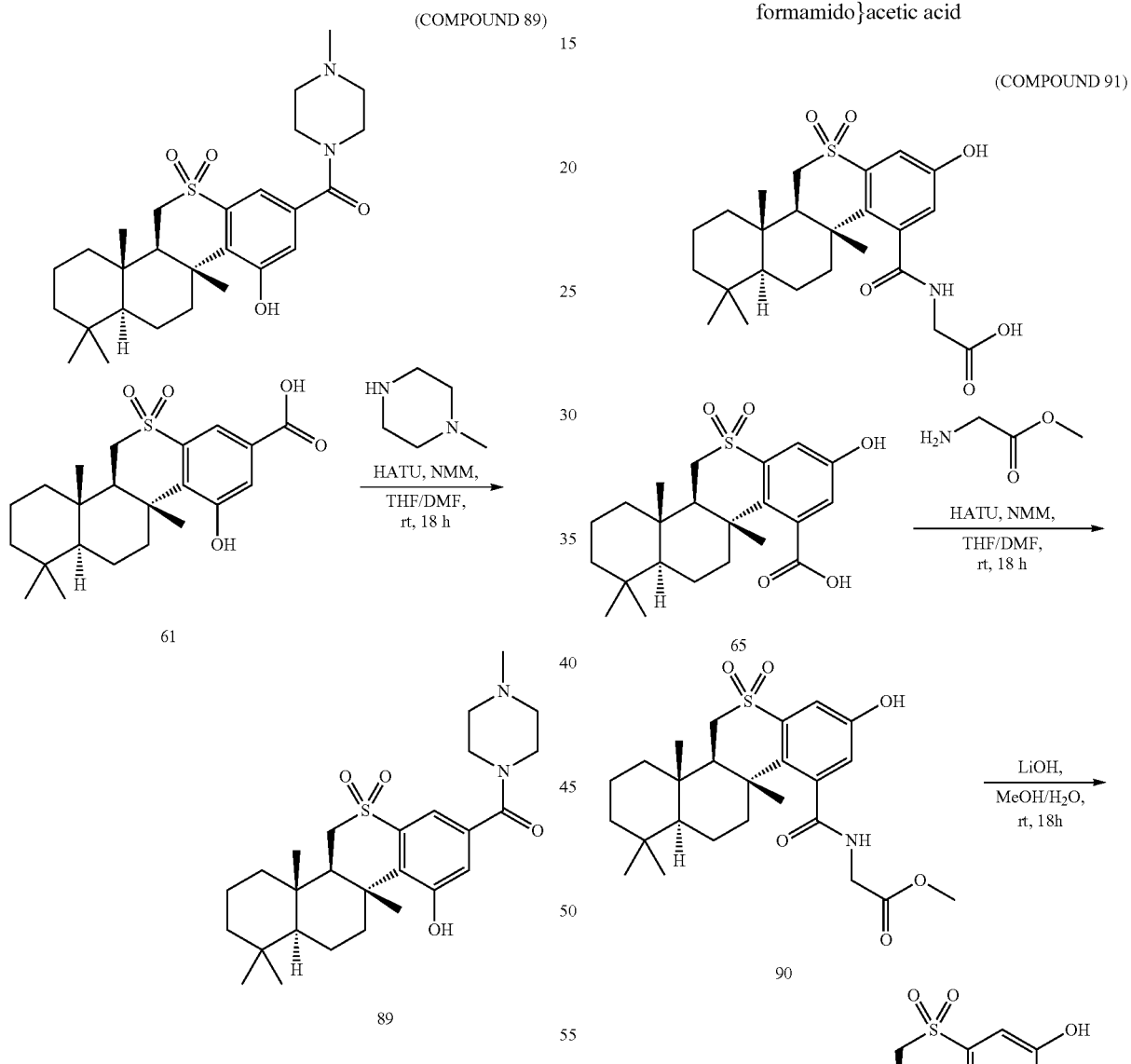

A mixture of (1R,10S,11S,16S)-3-methoxy-11,15,15-trimethyl-8,8-dioxo-8λ⁶-thiatetracyclo[8.8.0.0²,⁷.0¹¹,¹⁶]octadeca-2,4,6-triene-5-carboxylic acid (61) (0.20 g, 0.49 mmol), HATU (0.37 g, 0.98 mmol), N-methylmorpholine (0.10 mL, 1.5 mmol) and 1-methylpiperazine (0.15 mL, 1.5 mmol) in THF (10 mL) and DMF (2.0 mL) was stirred at room temperature for 18 h. The THF was evaporated under reduced pressure, the residue was quenched with water and the resulting solid was collected by filtration. The crude product was purified by flash column chromatography on silica gel (CH₂Cl₂/MeOH, 10:1) to give (1R,10R,11S,16S)-3-hydroxy-1,11,15,15-tetramethyl-5-[(4-methyl piperazin-1-yl)-carbonyl]-8λ⁶-thiatetracyclo[8.8.0.0²,⁷.0¹¹,¹⁶]octadeca-2,4,6-triene-8,8-dione (89) (0.13 g, 54%) as a white solid. ¹H NMR (CDCl₃): δ 9.55 (s, 1H), 7.23 (d, 1H), 7.07 (d, 1H), 3.84 (m, 2H), 3.49 (m, 2H), 3.18 (m, 3H), 2.52 (m, 2H), 2.38 (m, 2H), 2.33 (s, 3H), 2.15 (d, 1H), 1.78-1.32 (m, 6H), 1.28 (s, 3H), 1.24-1.05 (m, 2H), 0.98 (m, 1H), 0.90 (s, 6H), 0.86 (m, 1H), 0.82 (s, 3H). MS m/z 489 ($C_{27}H_{40}N_2O_4S+H^+$).

Example 41

Synthesis of 2-{[(1R,10R,11S,16S)-3-hydroxy-1,11,15,15-tetramethyl-8,8-dioxo-8λ⁶-thiatetracyclo[8.8.0.0²,⁷.0¹¹,¹⁶]octadeca-2,4,6-trien-3-yl]formamido}acetic acid A mixture of (1R,10R,11S,16S)-5-hydroxy-1,11,15,15-tetramethyl-8,8-dioxo-8$\lambda^6$-thiatetracyclo[8.8.0.0$^{2,7}$.0$^{11,16}$]octadeca-2,4,6-triene-3-carboxylic acid (65) (0.20 g, 0.49 mmol), HATU (0.37 g, 0.98 mmol), N-methyl morpholine (0.2 mL, 3 mmol) and glycine methyl ester hydrochloride (0.09 g, 2 mmol) in THF (10 mL) and DMF (2.0 mL) was stirred at room temperature for 18 h. The THF was evaporated under reduced pressure, the residue was quenched with water and the resulting solid was collected by filtration. The crude product was purified by flash column chromatography on silica gel (CH$_2$Cl$_2$/MeOH, 10:1) to give methyl 2-{[(1R,10R,11S,16S)-5-hydroxy-1,11,15,15-tetramethyl-8,8-dioxo-8$\lambda^6$-thiatetracyclo[8.8.0.0$^{2,7}$.0$^{11,16}$]octadeca-2,4,6-trien-3-yl]formamido}acetate (90) (0.05 g, 54%) as a cream solid. $^1$H NMR (CDCl$_3$): δ 7.37 (s, 1H), 7.21 (d, 1H), 6.89 (d, 1H), 6.70 (m, 1H), 4.19 (m, 2H), 3.81 (s, 3H), 3.40 (m, 2H), 2.62 (m, 1H), 2.16 (m, 1H), 1.76-1.34 (m, 10H), 1.20-1.00 (m, 2H), 0.98-0.92 (m, 4H), 0.89 (s, 3H), 0.82 (s, 3H). MS m/z 476 (C$_{25}$H$_{35}$NO$_6$S–H$^+$).

A mixture of methyl 2-{[(1R,10R,11S,16S)-5-hydroxy-1,11,15,15-tetramethyl-8,8-dioxo-8$\lambda^6$-thiatetracyclo[8.8.0.0$^{2,7}$.0$^{11,16}$]octadeca-2,4,6-trien-3-yl]formamido}acetate (90) (0.13 g, 0.27 mmol) and LiOH.H$_2$O (0.07 g, 2 mmol) in MeOH (10 mL) and water (10 mL) was stirred at room temperature for 18 h. The mixture was concentrated under reduced pressure and the aqueous residue was acidified with 1 M HCl. The resulting solid was collected by filtration to give 2-{[(1R,10R,11S,16S)-5-hydroxy-1,11,15,15-tetramethyl-8,8-dioxo-8$\lambda^6$-thiatetracyclo[8.8.0.0$^{2,7}$.0$^{11,16}$]octadeca-2,4,6-trien-3-yl]formamido}acetic acid (91) (0.09 g, 72%) as a brown solid. $^1$H NMR (CD$_3$OD): δ 8.82 (m, 1H), 7.24 (d, 1H), 7.03 (d, 1H), 4.06 (m, 2H), 3.47 (m 2H), 2.76 (d, 1H), 2.11 (d, 1H), 1.88-1.38 (m, 10H), 1.20 (m, 1H), 1.00 (m, 5H), 0.89 (s, 3H), 0.86 (s, 3H). MS m/z 464 (C$_{24}$H$_{33}$NO$_6$S+H$^+$).

Example 42

Synthesis of 2-{[(1R,10R,11S,16S)-3-hydroxy-1,11,15,15-tetramethyl-8,8-dioxo-8$\Lambda^6$-thiatetracyclo[8.8.0.0$^{2,7}$.0$^{11,16}$]octadeca-2,4,6-trien-5-yl]formamido}acetic acid (COMPOUND 93)

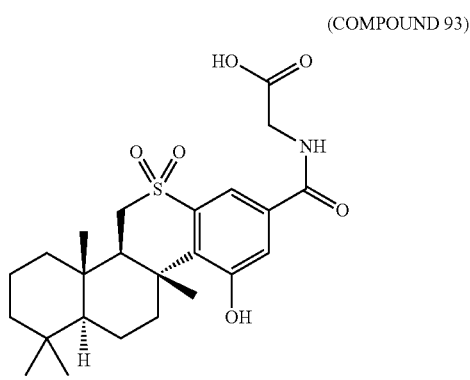

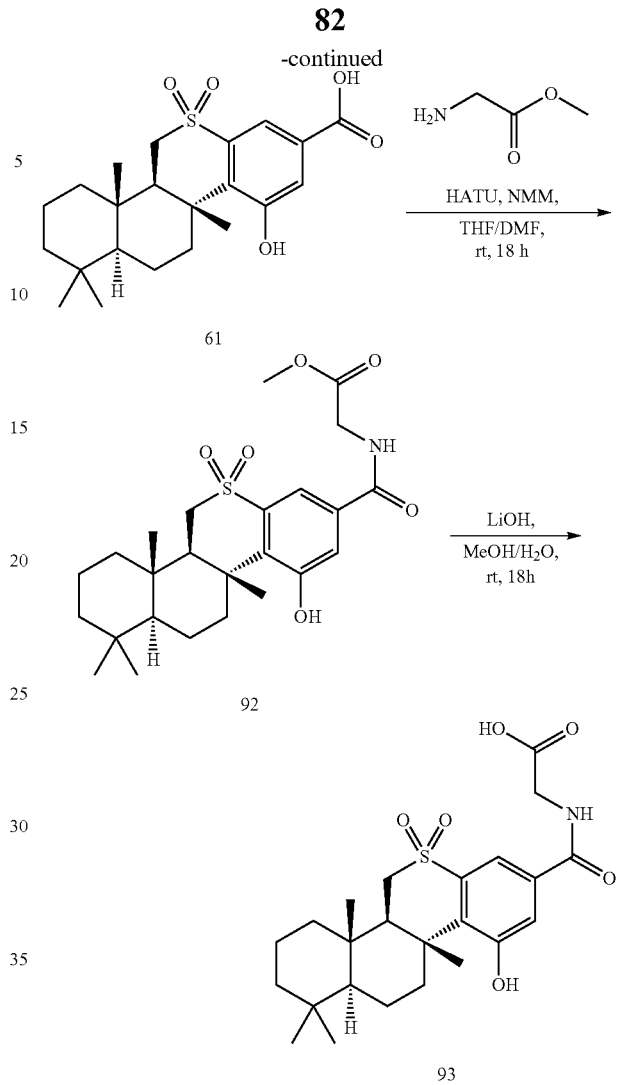

A mixture of (1R,10S,11S,16S)-3-methoxy-11,15,15-trimethyl-8,8-dioxo-8$\lambda^6$-thiatetracyclo[8.8.0.0$^{2,7}$.0$^{11,16}$]octadeca-2,4,6-triene-5-carboxylic acid (61) (0.20 g, 0.49 mmol), HATU (0.37 g, 0.98 mmol), N-methylmorpholine (0.20 mL, 3.0 mmol) and glycine methyl ester hydrochloride (0.18 g, 1.5 mmol) in THF (10 mL) and DMF (2.0 mL) was stirred at room temperature for 18 h. The THF was evaporated under reduced pressure, the residue was quenched with water and the resulting solid was collected by filtration. The crude product was purified by flash column chromatography on silica gel (CH$_2$Cl$_2$/MeOH, 10:1) to give methyl 2-{[(1R,10R,11S,16S)-3-hydroxy-1,11,15,15-tetramethyl-8,8-dioxo-8$\lambda^6$-thiatetracyclo[8.8.0.0$^{2,7}$.0$^{11,16}$]octadeca-2,4,6-trien-5-yl]formamido}acetate (92) (0.10 g, 42%) as a white solid. $^1$H NMR (CDCl$_3$): δ 8.16 (s, 1H), 7.81 (d, 1H), 7.71 (d, 1H), 7.18 (m, 1H), 4.24 (m, 2H), 3.32 (m, 3H), 2.30 (d, 1H), 1.76-1.00 (m, 16H), 0.97 (s, 3H), 0.88 (s, 3H), 0.84 (s, 3H). MS m/z 478 (C$_{25}$H$_{35}$NO$_6$S+H$^+$).

A mixture of methyl 2-{[(1R,10R,11S,16S)-3-hydroxy-1,11,15,15-tetramethyl-8,8-dioxo-8$\lambda^6$-thiatetracyclo[8.8.0.0$^{2,7}$.0$^{11,16}$]octadeca-2,4,6-trien-5-yl]-formamido}acetate (92) (0.07 g, 0.2 mmol) and LiOH.H$_2$O (0.07 g, 2 mmol) in MeOH (10 mL) and water (2.0 mL) was stirred at room temperature for 18 h. The reaction mixture was concentrated under reduced pressure, the aqueous residue was acidified with 1 M HCl and the resulting solid was collected by filtration to give 2-{[(1R,10R,11S,16S)-3-hydroxy-1,11,15,15-tetramethyl-8,8-dioxo-8λ⁶-thiatetracyclo[8.8.0.0²,⁷.0¹¹,¹⁶]octadeca-2,4,6-trien-5-yl]formamido}acetic acid (93) (0.057 g, 84%) as a pale brown solid. ¹H NMR (CD₃OD): δ 7.79 (d, 1H), 7.43 (d, 1H), 4.07 (s, 2H), 3.60 (d, 1H), 3.38 (m, 2H), 2.26 (d, 1H), 1.86-1.16 (m, 12H), 1.10-1.00 (m, 5H), 0.90 (s, 3H), 0.88 (s, 3H). MS m/z 462 ($C_{24}H_{33}NO_6S-H^+$).

Example 43

Synthesis of (1R,10R,11S,16S)-5-hydroxy-1,11,15,15-tetramethyl-3-[(4-methylpiperazin-1-yl)carbonyl]-8λ⁶-thiatetracyclo[8.8.0.0²,⁷.0¹¹,¹⁶]octadeca-2,4,6-triene-8,8-dione 34%) as a white solid. ¹H NMR (CDCl₃): δ 7.29 (d, 1H), 6.77 (d, 1H), 3.62-3.20 (m, 5H), 2.70-2.00 (m, 10H), 1.78-1.24 (m, 10H), 1.20-1.00 (m, 2H), 0.99-0.92 (m, 4H), 0.88 (s, 3H), 0.82 (s, 3H). MS m/z 489 ($C_{27}H_{40}N_2O_4S+H^+$).

Example 44

Synthesis of (1R,10R,11S,16S)-5-hydroxy-N-methoxy-1,11,15,15-tetramethyl-8,8-dioxo-8Λ⁶-thiatetracyclo[8.8.0.0²,⁷.0¹¹,¹⁶]octadeca-2,4,6-triene-3-carboxamide

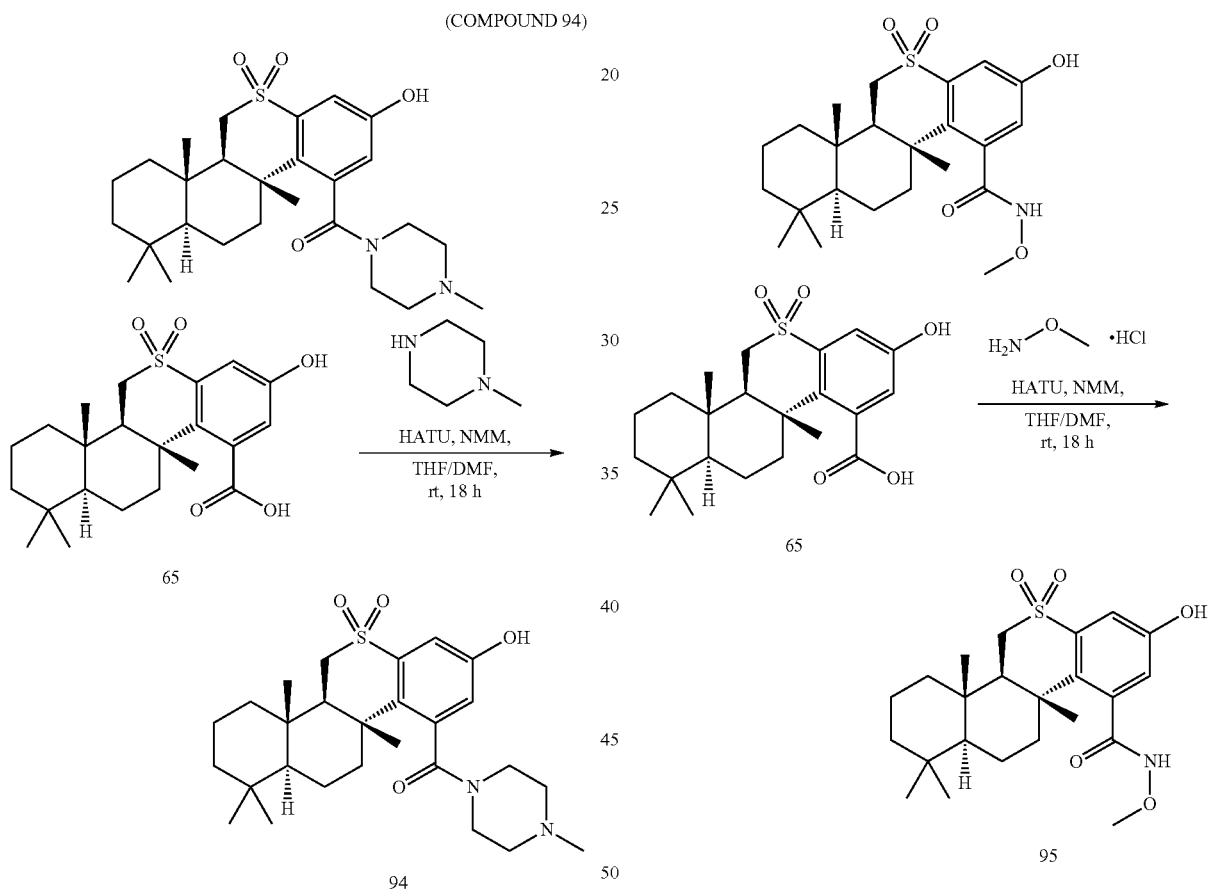

A mixture of (1R,10R,11S,16S)-5-hydroxy-1,11,15,15-tetramethyl-8,8-dioxo-8λ⁶-thiatetracyclo[8.8.0.0²,⁷.0¹¹,¹⁶]octadeca-2,4,6-triene-3-carboxylic acid (65) (0.20 g, 0.49 mmol), HATU (0.37 g, 0.98 mmol), N-methylmorpholine (0.10 mL, 1.5 mmol) and 1-methyl piperazine (0.15 mL, 1.5 mmol) in THF (10 mL) and DMF (2.0 mL) was stirred at room temperature for 18 h. The THF was evaporated under reduced pressure, the residue was quenched with water and the resulted solid was collected by filtration. The crude product was purified by flash column chromatography on silica gel (CH₂Cl₂/MeOH, 10:1). The resulting material was further purified by preparative HPLC (NH₄OAc/CH₃CN) to give (1R,10R,11S,16S)-5-hydroxy-1,11,15,15-tetramethyl-3-[(4-methylpiperazin-1-yl)carbonyl]-8λ⁶-thiatetracyclo[8.8.0.0²,⁷.0¹¹,¹⁶]octadeca-2,4,6-triene-8,8-dione (94) (0.085 g, A mixture of (1R,10R,11S,16S)-5-hydroxy-1,11,15,15-tetramethyl-8,8-dioxo-8λ⁶-thiatetracyclo[8.8.0.0²,⁷.0¹¹,¹⁶]octadeca-2,4,6-triene-3-carboxylic acid (65) (0.20 g, 0.49 mmol), HATU (0.37 g, 0.98 mmol), N-methyl morpholine (0.10 mL, 1.5 mmol) and methoxyamine hydrochloride (0.12 g, 1.5 mmol) in THF (10 mL) and DMF (2.0 mL) was stirred at room temperature for 18 h. The THF was evaporated under reduced pressure, the residue was quenched with water and the resulting solid was collected by filtration. The crude product was purified by flash column chromatography on silica gel (Hexanes/EtOAc, 1:2) to give (1R,10R,11S,16S)-5-hydroxy-N-methoxy-1,11,15,15-tetramethyl-8,8-dioxo-8λ⁶-thiatetracyclo[8.8.0.0²,⁷.0¹¹,¹⁶]octadeca-2,4,6-triene-3-carboxamide (95) (0.035 g, 16%) as a white solid. ¹H NMR (CD₃OD): δ 7.27 (d, 1H), 6.87 (d, 1H), 3.83 (s, 3H), 3.47 (m, 2H), 2.70 (m, 1H), 2.11 (d, 1H), 1.87-1.38 (m, 10H), 1.30-1.15 (m, 1H), 1.04-0.94 (m, 5H), 0.90 (s, 3H), 0.86 (s, 3H). MS m/z 434 ($C_{23}H_{33}NO_5S-H^+$).

Example 45

Synthesis of (1R,10R,11S,16S)-3-hydroxy-N-methoxy-1,11,15,15-tetramethyl-8,8-dioxo-8λ⁶-thiatetracyclo[8.8.0.0²,⁷.0¹¹,¹⁶]octadeca-2,4,6-triene-5-carboxamide A mixture of (1R,10S,11S,16S)-3-methoxy-11,15,15-trimethyl-8,8-dioxo-8λ⁶-thiatetracyclo[8.8.0.0²,⁷.0¹¹,¹⁶]octadeca-2,4,6-triene-5-carboxylic acid (61) (0.20 g, 0.49 mmol), HATU (0.37 g, 0.98 mmol), N-methylmorpholine (0.20 mL, 3.0 mmol) and methoxyamine hydrochloride (0.12 g, 1.5 mmol) in THF (10 mL) and DMF (2.0 mL) was stirred at room temperature for 18 h. The THF was evaporated under reduced pressure, the residue was quenched with water and the resulting solid was collected by filtration. The crude product was purified by flash column chromatography on silica gel (Hexanes/EtOAc, 1:2) to give (1R,10R,11S,16S)-3-hydroxy-N-methoxy-1,11,15,15-tetramethyl-8,8-dioxo-8λ⁶-thiatetracyclo[8.8.0.0²,⁷.0¹¹,¹⁶]octadeca-2,4,6-triene-5-carboxamide (96) (0.06 g, 28%) as a white solid. ¹H NMR (CD₃OD): δ 7.64 (d, 1H), 7.37 (d, 1H), 3.79 (s, 3H), 3.58 (m, 1H), 3.36 (m, 2H), 2.24 (d, 1H), 1.86-1.16 (m, 12H), 1.09-0.99 (m, 5H), 0.90 (s, 3H), 0.88 (s, 3H). MS m/z 434 ($C_{23}H_{33}NO_5S-H^+$).

Example 46

Synthesis of 1-{[(1R,10R,11S,16S)-3-hydroxy-1,11,15,15-tetramethyl-8,8-dioxo-8λ⁶-thiatetracyclo[8.8.0.0²,⁷.0¹¹,¹⁶]octadeca-2,4,6-trien-5-yl]carbonyl}piperidine-4-carboxylic acid

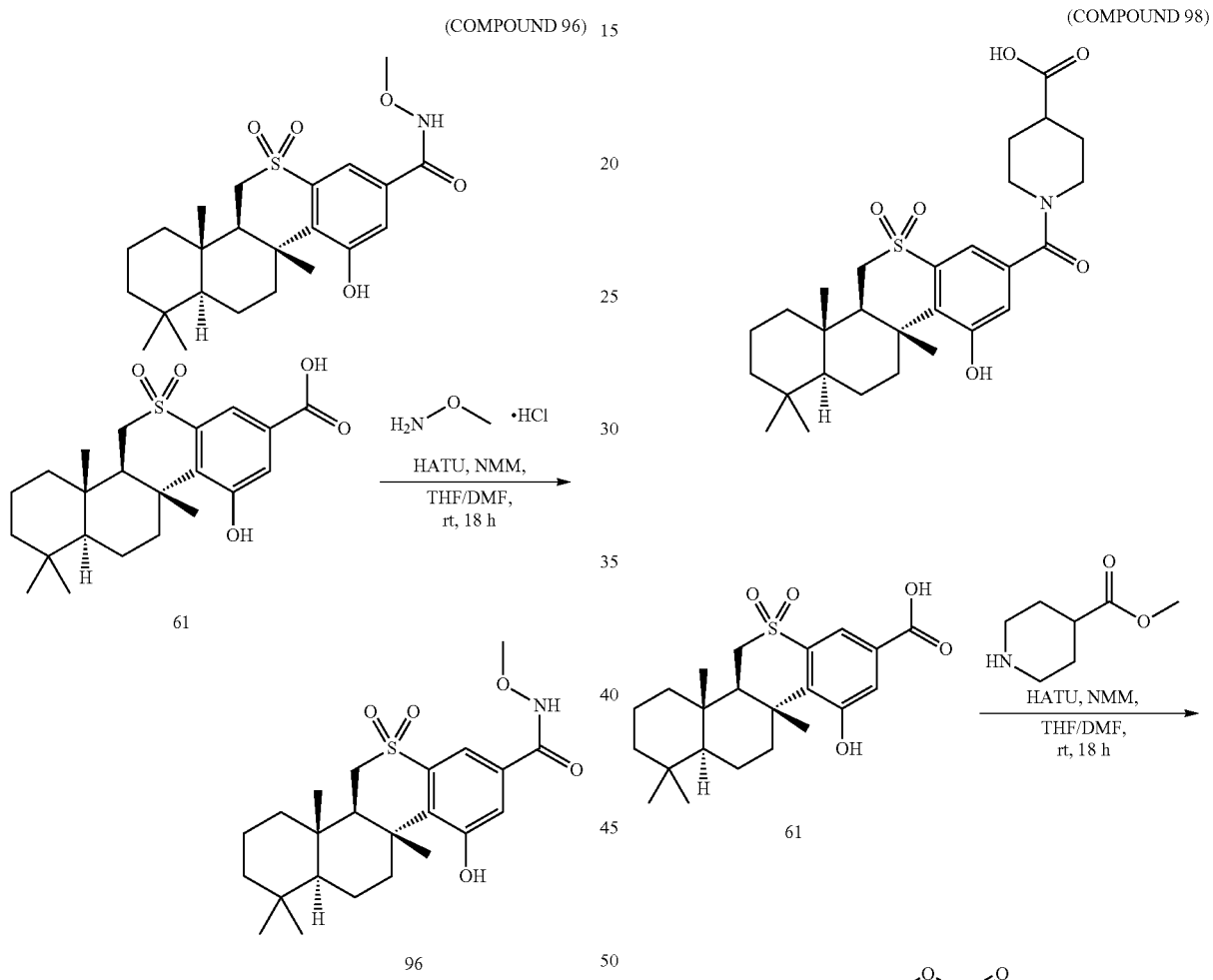

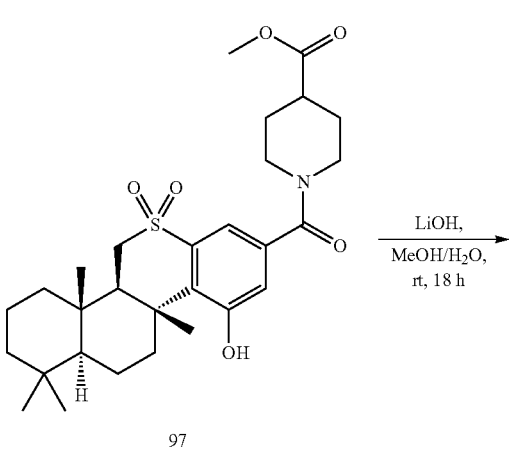

-continued

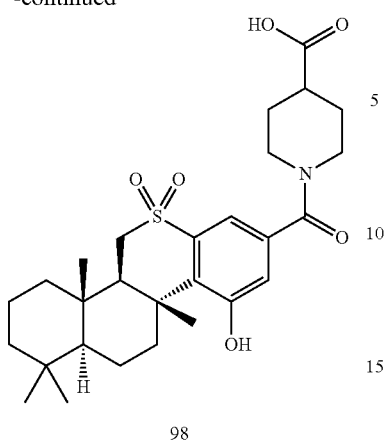

98

A mixture of (1R,10S,11S,16S)-3-methoxy-11,15,15-trimethyl-8,8-dioxo-8λ$^6$-thiatetracyclo[8.8.0.0$^{2,7}$.0$^{11,16}$]octadeca-2,4,6-triene-5-carboxylic acid (61) (0.20 g, 0.49 mmol), HATU (0.37 g, 0.98 mmol), N-methylmorpholine (0.10 mL, 1.5 mmol) and methyl piperidinecarboxylate (0.2 mL, 2 mmol) in THF (10 mL) and DMF (2.0 mL) was stirred at room temperature for 18 h. The THF was evaporated under reduced pressure, the residue was quenched with water and the resulting solid was collected by filtration. The crude product was purified by flash column chromatography on silica gel (CH$_2$Cl$_2$/MeOH, 20:1) to give methyl 1-{[(1R,10R,11S,16S)-3-hydroxy-1,11,15,15-tetramethyl-8,8-dioxo-8λ$^6$-thiatetracyclo[8.8.0.0$^{2,7}$.0$^{11,16}$]octadeca-2,4,6-trien-5-yl]carbonyl}piperidine-4-carboxylate (97) (0.10 g, 37%) as a white solid.

A mixture of methyl 1-{[(1R,10R,11S,16S)-3-hydroxy-1,11,15,15-tetramethyl-8,8-dioxo-8λ$^6$-thiatetracyclo[8.8.0.0$^{2,7}$.0$^{11,16}$]octadeca-2,4,6-trien-5-yl]carbonyl}piperidine-4-carboxylate (97) (0.10 g, 0.18 mmol) and LiOH.H$_2$O (0.10 g, 2.4 mmol) in MeOH (10 mL) and water (2.0 mL) was stirred at room temperature for 18 h. The reaction mixture was concentrated under reduced pressure and acidified with 1 M HCl. The resulting solid was collected by filtration to give 1-{[(1R,10R,11S,16S)-3-hydroxy-1,11,15,15-tetramethyl-8,8-dioxo-8λ$^6$-thiatetracyclo[8.8.0.0$^{2,7}$.0$^{11,16}$]octadeca-2,4,6-trien-5-yl]carbonyl}piperidine-4-carboxylic acid (98) (0.06 g, 63%) as a white solid. $^1$H NMR (CD$_3$OD): δ 7.29 (d, 1H), 6.97 (d, 1H), 4.43 (m, 1H), 3.70 (m, 1H), 3.58 (m, 1H), 3.36 (m, 2H), 3.26-2.96 (m, 4H), 2.62 (m, 1H), 2.24 9d, 1H), 2.10-1.16 (m, 13H), 1.09-0.99 (m, 5H), 0.90 (s, 3H), 0.88 (s, 3H). MS m/z 516 (C$_{28}$H$_{39}$NO$_6$S–H$^+$).

Example 47

Synthesis of (1R,10R,11S,16S)-5-hydroxy-1,11,15,15-tetramethyl-3-[(piperazin-1-yl)carbonyl]-8λ$^6$-thiatetracyclo[8.8.0.0$^{2,7}$.0$^{11,16}$]octadeca-2,4,6-triene-8,8-dione (COMPOUND 100)

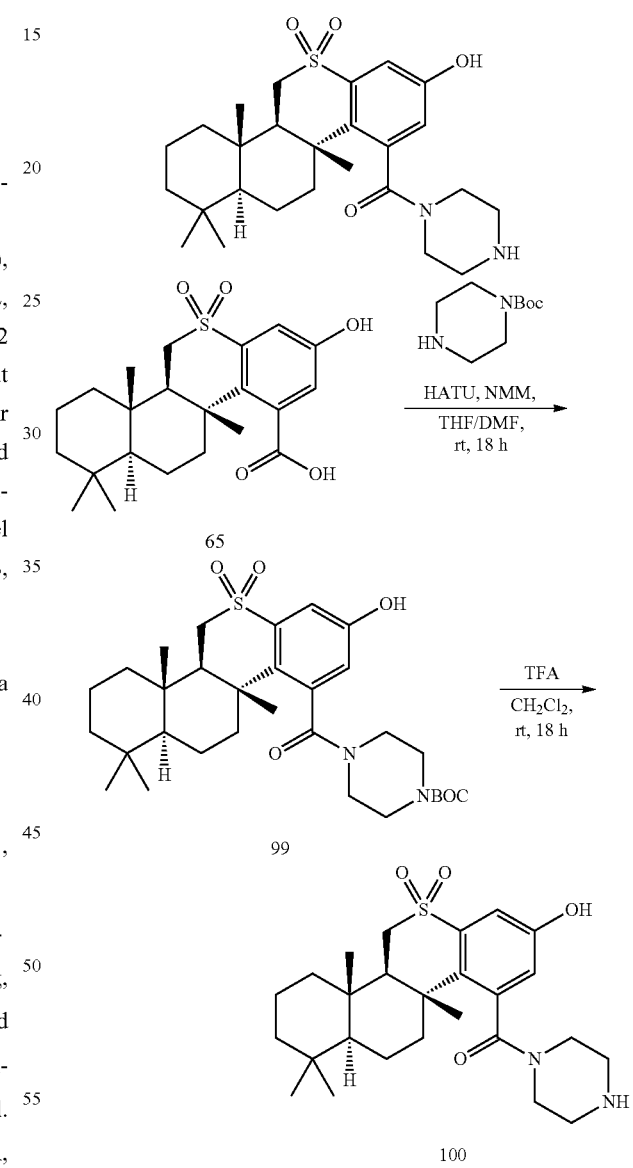

A mixture of (1R,10R,11S,16S)-5-hydroxy-1,11,15,15-tetramethyl-8,8-dioxo-8λ$^6$-thiatetracyclo[8.8.0.0$^{2,7}$.0$^{11,16}$]octadeca-2,4,6-triene-3-carboxyl ic acid (65) (0.20 g, 0.49 mmol), HATU (0.37 g, 0.98 mmol), N-methyl morpholine (0.1 mL, 1.5 mmol) and 1-Boc-piperazine (0.27 g, 1.5 mmol) in THF (10 mL) and DMF (2.0 mL) was stirred at room temperature for 18 h. The THF was evaporated under reduced pressure, the residue was quenched with water and the resulting solid was collected by filtration. The crude product was purified by flash column chromatography on silica gel (CH$_2$Cl$_2$/MeOH, 10:1) to give tert-butyl 4-{[(1R,10R,11S,16S)-5-hydroxy-1,11,15,15-tetramethyl-8,8-dioxo-8λ$^6$-thiatetracyclo[8.8.0.0$^{2,7}$.0$^{11,16}$]octadeca-2,4,6-trien-3-yl]carbonyl}piperazine-1-carboxylate (99) (0.13 g, 46%) as a white solid.

A mixture of tert-butyl 4-{[(1R,10R,11S,16S)-5-hydroxy-1,11,15,15-tetramethyl-8,8-dioxo-8λ$^6$-thiatetracyclo[8.8.0.0$^{2,7}$.0$^{11,16}$]octadeca-2,4,6-trien-3-yl]carbonyl}piperazine-1-carboxylate (99) (0.13 g, 0.23 mmol) and trifluoroacetic acid (1.0 mL, 13 mmol) in CH$_2$Cl$_2$ (10 mL) was stirred at room temperature under N$_2$ for 18 h. The mixture was concentrated under reduced pressure, and basified with Et$_3$N, dissolved in EtOAc and washed with water. The organic layer was separated and concentrated to dryness under reduced pressure to give (1R,10R,11S,16S)-5-hydroxy-1,11,15,15-tetramethyl-3-[(piperazin-1-yl)carbonyl]-8λ$^6$-thiatetracyclo[8.8.0.0$^{2,7}$.0$^{11,16}$]octadeca-2,4,6-triene-8,8-dione (100) (0.06 g, 55%) as a brown solid. $^1$H NMR (CD$_3$OD): δ 7.27 (d, 1H), 6.78 (d, 1H), 3.50 (m, 3H), 3.02 (m 2H), 2.90 (m, 2H), 2.53 (m, 1H), 2.16 (d, 1H), 1.88-1.14 (m, 14H), 1.00 (m, 5H), 0.90 (s, 3H), 0.86 (s, 3H). MS m/z 475 (C$_{26}$H$_{38}$N$_2$O$_4$S+H$^+$).

Example 48

Synthesis of (1R,10R,11S,16S)-3-hydroxy-1,11,15,15-tetramethyl-5-[(piperazin-1-yl)carbonyl]-8λ$^6$-thiatetracyclo[8.8.0.0$^{2,7}$.0$^{11,16}$]octadeca-2,4,6-triene-8,8-dione (COMPOUND 102)

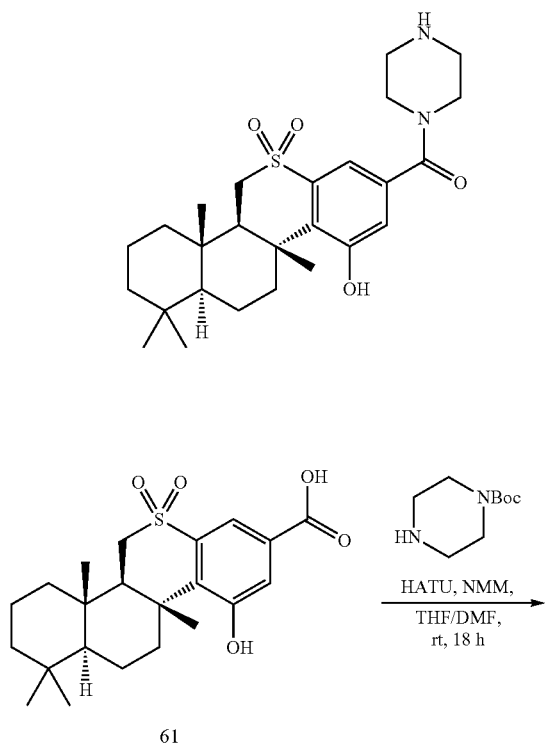

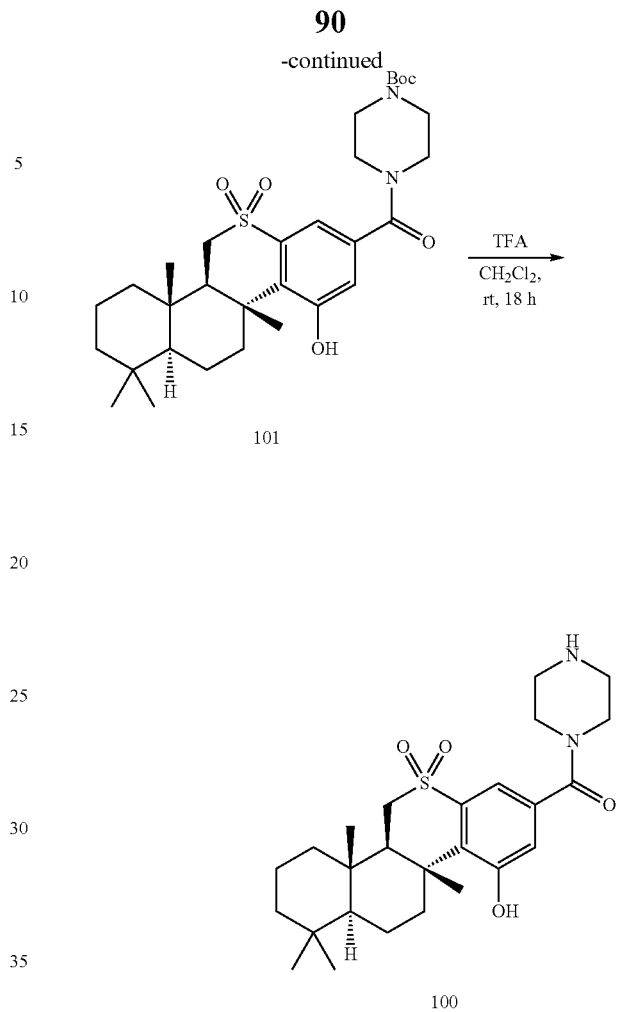

A mixture of (1R,10S,11S,16S)-3-methoxy-11,15,15-trimethyl-8,8-dioxo-8λ$^6$-thiatetracyclo[8.8.0.0$^{2,7}$.0$^{11,16}$]octadeca-2,4,6-triene-5-carboxylic acid (61) (0.20 g, 0.49 mmol), HATU (0.37 g, 0.98 mmol), N-methylmorpholine (0.10 mL, 1.5 mmol) and 1-Boc-piperazine (0.2 mL, 2 mmol) in THF (10 mL) and DMF (2.0 mL) was stirred at room temperature for 18 h. The THF was evaporated under reduced pressure, the residue was quenched with water and the resulting solid was collected by filtration to give methyl tert-butyl 4-{[(1R,10R,11S,16S)-3-hydroxy-1,11,15,15-tetramethyl-8,8-dioxo-8λ$^6$-thiatetracyclo[8.8.0.0$^{2,7}$.0$^{11,16}$]octadeca-2,4,6-trien-5-yl]carbonyl}piperazine-1-carboxylate (101) (0.22 g, 78%) as a pale brown solid.

A mixture of methyl tert-butyl 4-{[(1R,10R,11S,16S)-3-hydroxy-1,11,15,15-tetramethyl-8,8-dioxo-8λ$^6$-thiatetracyclo[8.8.0.0$^{2,7}$.0$^{11,16}$]octadeca-2,4,6-trien-5-yl]carbonyl}piperazine-1-carboxylate (101) (0.22 g, 0.38 mmol) and trifluoroacetic acid (1.0 mL, 13 mmol) in CH$_2$Cl$_2$ (10 mL) was stirred under N$_2$ at room temperature for 18 h. The reaction mixture was concentrated under reduced pressure, basified with Et$_3$N, then dissolved in EtOAc and washed with water. The organic layer was separated and concentrated under reduced pressure to give (1R,10R,11S,16S)-3-hydroxy-1,11,15,15-tetramethyl-5-[(piperazin-1-yl)carbonyl]-8λ$^6$-thiatetracyclo[8.8.0.0$^{2,7}$.0$^{11,16}$]-octadeca-2,4,6-triene-8,8-dione (102) (0.13 g, 72%) as a tan solid. $^1$H NMR (CD$_3$Cl): δ 7.24 (s, 1H), 7.06 (s, 1H), 3.78 (m, 2H), 3.47 (m, 2H), 3.20

(m, 3H), 2.97 (m, 2H), 2.84 (m, 2H), 2.16 (d, 1H), 1.78-1.06 (m, 14H), 1.03-0.85 (m, 7H), 0.82 (s, 3H). MS m/z 475 ($C_{26}H_{38}N_2O_4S+H^+$).

Example 49

Synthesis of (1R,10R,11S,16S)-5-hydroxy-3-methoxy-1,11,15,16-tetramethyl-8$\Lambda^6$-thiatetracyclo[8.8.0.0$^{2,7}$.0$^{11,16}$]octadeca-2,4,6-triene-8,8-dione

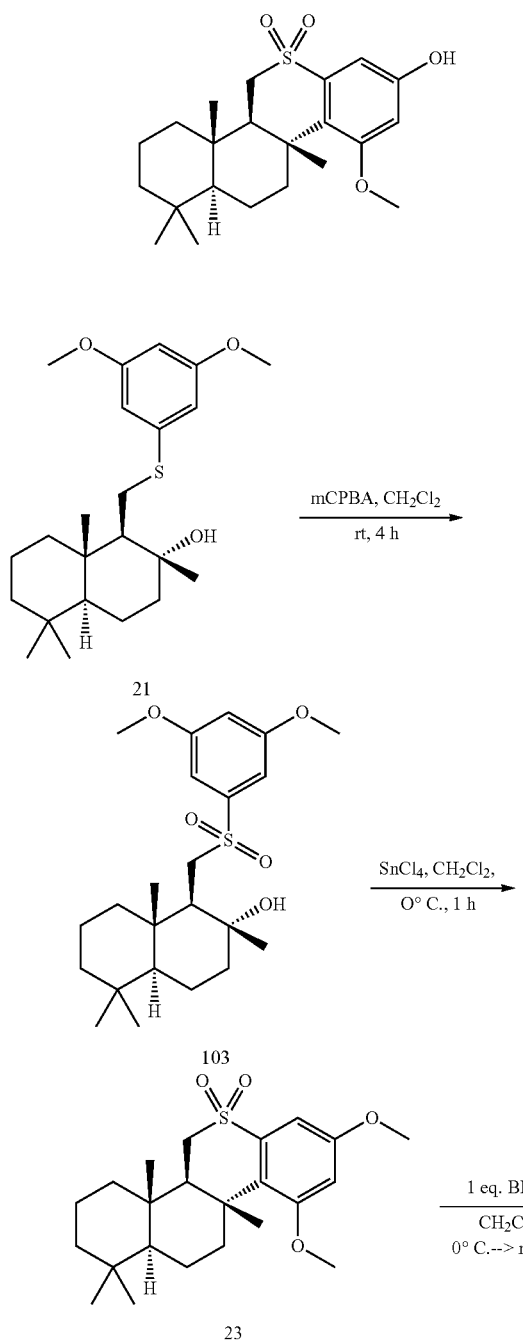

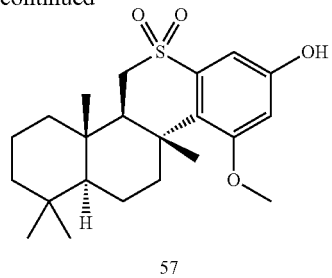

Compound 21 was prepared according to Example 6. To a solution of compound 21 (32.37 g, 82.45 mmol) in dichloromethane (500 mL) was added 3-chloroperoxybenzoic acid (77%, 40.63 g, 181.3 mmol) in small portions. The reaction was stirred under argon at room temperature for 4 h then concentrated to afford a pink residue. The residue was quenched with saturated aqueous sodium bicarbonate (500 mL) and extracted with ethyl acetate (500 mL). The aqueous phase was extracted with ethyl acetate (250 mL). The organic layers were combined and washed with brine (500 mL) then dried (MgSO$_4$) and concentrated to afford a brown oil. The oil was purified by column chromatography on silica gel (Hexanes:Ethyl acetate, 4:1 to 3:1 to 2:1 to 1:1) to afford compound 103 (16.08 g, 47%) as a yellow solid. $^1$H NMR (CDCl$_3$): δ 7.05 (d, J=2.3 Hz, 2H), 6.68 (t, J=2.3 Hz, 1H), 3.85 (s, 6H), 3.24 (dd, J=14.4, 4.9 Hz, 1H), 3.07 (m, 1H), 2.65 (br s, 1H), 2.07 (m, 2H), 2.02 (t, J=3.1 Hz, 1H), 1.98 (t, J=3.1 Hz, 1H), 1.56-1.03 (m, 8H), 1.09 (s, 3H), 0.90 (s, 3H), 0.79 (s, 3H), 0.76 (s, 3H).

To a solution of compound 103 (16.08 g, 37.87 mmol) in dichloromethane (500 mL) at 0° C. under argon was added tin tetrachloride (13.5 mL, 114 mmol) slowly. The reaction was stirred at 0° C. for 1 h then quenched with water (500 mL). The organic phase was separated and concentrated. The aqueous phase was extracted with ethyl acetate (500 mL), and the organic layer was separated and concentrated. The aqueous phase was extracted with dichloromethane (250 mL). The organic layer was combined with the residues and washed with brine (500 mL) then dried (MgSO$_4$) and concentrated to afford compound 23 (17.30 g, 100%) as a red solid. $^1$H NMR (CDCl$_3$): δ 6.95 (d, J=2.6 Hz, 1H), 6.55 (d, J=2.6 Hz, 1H), 3.83 (s, 3H), 3.80 (s, 3H), 3.36-3.13 (m, 3H), 2.28 (d, J=11.7 Hz, 1H), 1.73-0.99 (m, 10H), 1.38 (s, 3H), 0.99 (s, 3H), 0.86 (s, 3H), 0.83 (s, 3H).

To a suspension of compound 23 (5.00 g, 12.3 mmol) in dichloromethane (20 mL) at 0° C. under argon was slowly added boron tribromide (1.0 M in DCM, 12.5 mL, 12.5 mmol). The mixture was stirred for 60 h then concentrated. The residue was dissolved in ethyl acetate (50 mL), quenched with water (250 mL) and extracted with ethyl acetate (2×200 mL). The organic layer was washed with brine (2×250 mL) then dried (MgSO$_4$) and concentrated to afford a brown foam. The crude product was purified by column chromatography on silica gel (hexanes:ethyl acetate, 2:1) to afford compound 57 (2.90 g, 60%) as a pale solid. $^1$H NMR (CDCl$_3$): δ 7.00 (d, J=2.6 Hz, 1H), 6.54 (d, J=2.5 Hz, 1H), 6.20 (s, 1H), 3.79 (s, 3H), 3.36-3.16 (m, 3H), 2.27 (d, J=11.4 Hz, 1H), 1.72-1.00 (m, 10H), 1.38 (s, 3H), 0.95 (s, 3H), 0.86 (s, 3H), 0.83 (s, 3H). $^{13}$C NMR (CDCl$_3$): δ 159.7, 157.0, 139.3, 127.8, 105.4, 102.4, 56.2, 56.1, 53.4, 46.3, 41.9, 39.8, 39.0, 38.1, 33.7, 33.5, 21.7, 19.2, 19.1, 18.8, 17.8, 17.7. MS m/z 393 ($C_{22}H_{32}O_4S+H^+$).

Example 50

Synthesis of 2-{[(1R,10R,11S,16S)-3-methoxy-1,11,15,15-tetramethyl-8,8-dioxo-8Λ⁶-thiatetracyclo[8.8.0.0$^{2,7}$.0$^{11,16}$]octadeca-2,4,6-trien-5-yl]oxy}acetic acid 53.1, 45.9, 41.9, 41.6, 39.5, 38.7, 37.7, 33.4, 33.1, 29.9, 21.4, 18.9, 18.7, 18.5, 17.4. MS m/z 451 ($C_{24}H_{34}O_6S+H^+$).

Example 51

Synthesis of 2-{[(1R,10R,11S,16S)-3-hydroxy-1,11,15,15-tetramethyl-8,8-dioxo-8Λ⁶-thiatetracyclo[8.8.0.0$^{2,7}$.0$^{11,16}$]octadeca-2,4,6-trien-5-yl]oxy}acetic acid

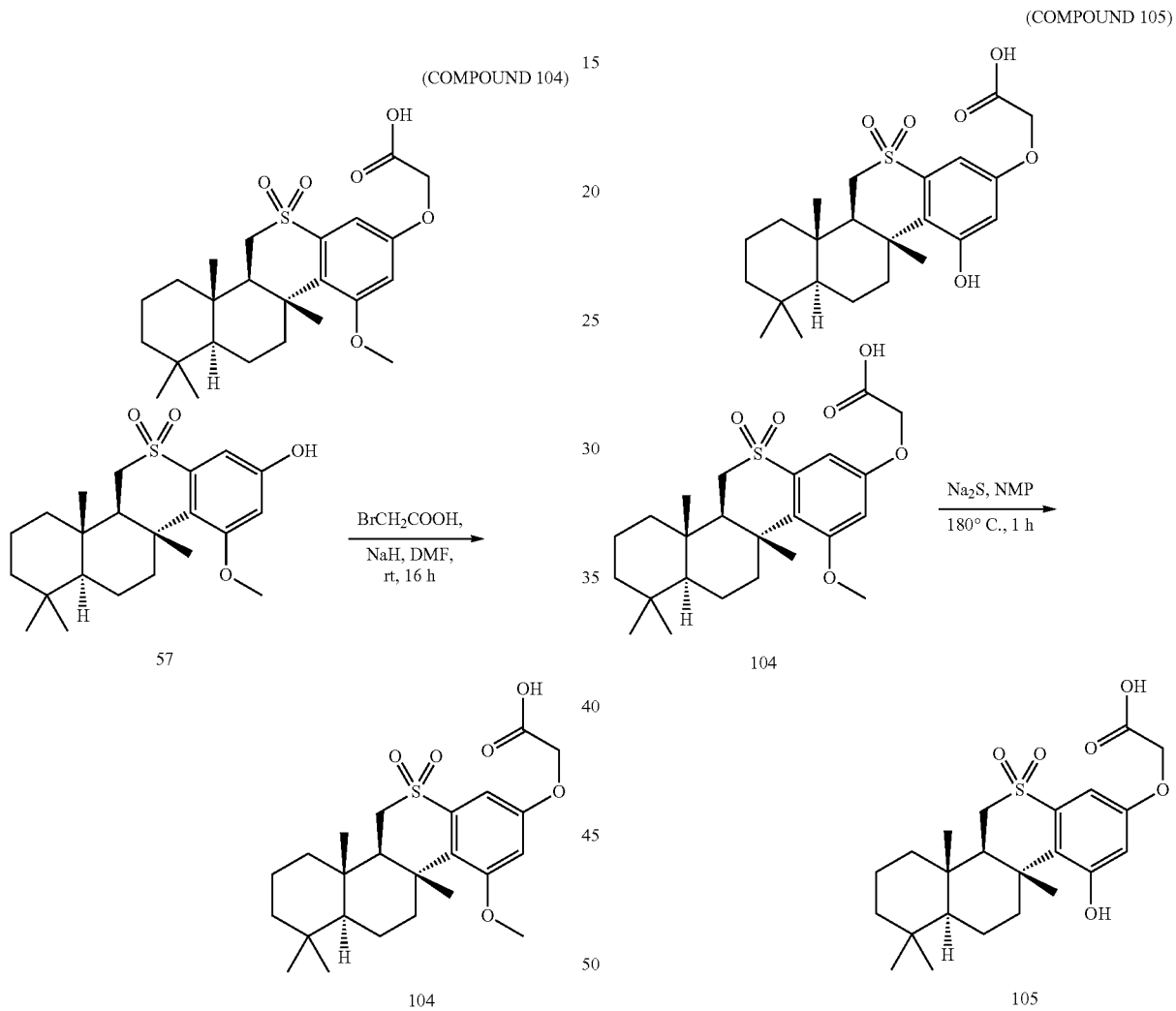

To a suspension of compound 57 (21 mg, 0.055 mmol) and bromoacetic acid (26 mg, 0.19 mmol) in dimethylformamide (1 mL) under argon was added sodium hydride (60%, 19 mg, 0.47 mmol) and stirred for 16 h. The mixture was quenched with water (3 mL), acidified with hydrochloric acid (1 M, 2 mL), and extracted with ethyl acetate (3×5 mL). The organic layer was washed with brine (2×10 mL) then dried (MgSO$_4$) and concentrated to afford compound 104 (19 mg, 77%) as a white solid. $^1$H NMR (CDCl$_3$): δ 6.90 (d, J=2.6 Hz, 1H), 6.68 (d, J=2.6 Hz, 1H), 4.71 (s, 2H), 3.81 (s, 3H), 3.24-3.17 (m, 3H), 2.27 (d, J=12.0 Hz, 1H), 1.72-0.97 (m, 15H), 0.94 (s, 3H), 0.89-0.88 (m, 1H), 0.83 (s, 3H). $^{13}$C NMR (CDCl$_3$): δ 172.5, 159.3, 157.5, 139.8, 129.6, 105.3, 99.2, 65.1, 55.9, To a solution of 104 (62 mg, 0.14 mmol) in N-methyl-2-pyrrolidone (2 mL) in a microwaveable vial was added sodium sulphide (57 mg, 0.73 mmol). The mixture was stirred at 180° C. in a microwave for 1 h then diluted with ethyl acetate (20 mL) and hydrochloric acid (0.25 M, 20 mL). The organic layer was washed with brine (3×20 mL) then dried (MgSO$_4$) and concentrated to afford a yellow solid. The solid was dissolved in ethyl acetate (20 mL) and washed with aqueous sodium hydroxide (1 M, 20 mL). The aqueous phase was separated and hydrochloric acid was added (1 M, 20 mL). The solution was extracted with ethyl acetate (3×10 mL), and the extracts were dried (MgSO$_4$) and concentrated to afford compound 105 (32 mg, 54%) as a yellow solid. $^1$H NMR (CD$_3$OD): $^1$H NMR (CD$_3$OD): δ 6.79 (d, J=1.9 Hz, 1H), 6.56

(d, J=1.7 Hz, 1H), 4.65 (s, 2H), 3.52 (d, J=13.4 Hz, 1H), 1.84-1.49 (m, 6H), 1.44 (s, 3H), 1.41-1.03 (m, 7H), 1.00 (s, 3H), 0.89 (s, 3H), 0.87 (s, 3H). $^{13}$C NMR (CD$_3$OD): δ 163.3, 157.3, 139.7, 107.4, 99.5, 56.3, 53.5, 51.9, 50.1, 45.6, 45.3, 41.6, 41.5, 39.2, 38.5, 37.5, 33.0, 32.3, 20.5, 18.5, 18.2, 17.4, 16.4. MS m/z 435 (C$_{23}$H$_{32}$O$_6$S–H$^+$).

Example 52

Synthesis of (1R,10R,11S,16S)-5-hydroxy-3-methoxy-1,11,15,15-tetramethyl-6-(morpholin-4-ylmethyl)-8Λ$^6$-thiatetracyclo[8.8.0.0$^{2,7}$.0$^{11,16}$]octadeca-2,4,6-triene-8,8-dione

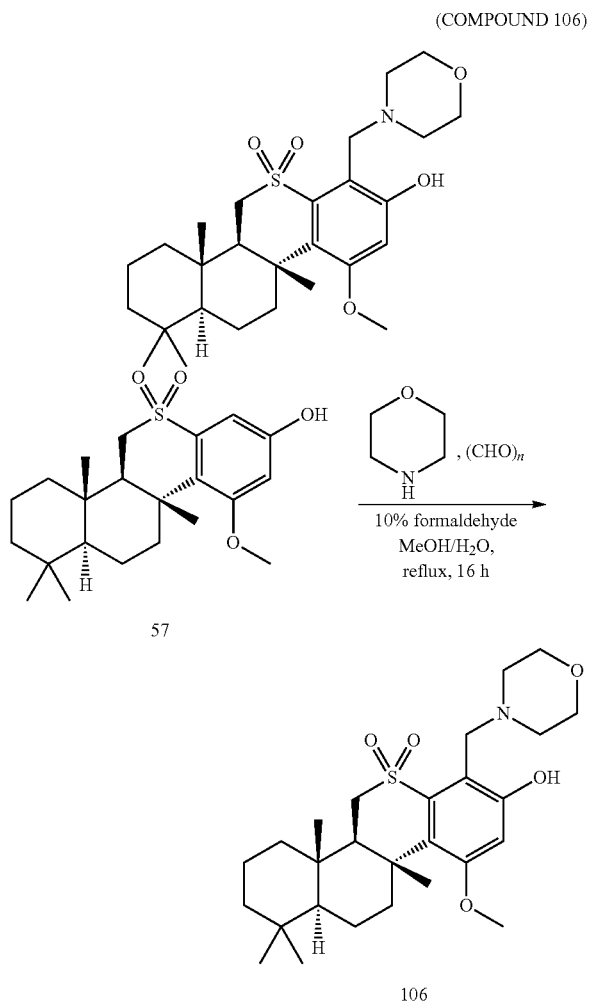

A mixture of compound 57 (25 mg, 0.064 mmol), morpholine (0.02 mL, 0.2 mmol), formaldehyde (10%, 0.50 mL, 1.7 mmol), and paraformaldehyde (80 mg, 2.7 mmol) in methanol (3 mL) was heated to reflux for 4 h. Additional morpholine (0.02 mL, 0.2 mmol) was added, and heating was continued for another 12 h. The reaction mixture was cooled to room temperature, diluted with ethyl acetate (5 mL), washed with saturated aqueous ammonium chloride (3×5 mL), dried (MgSO$_4$), and concentrated to afford a white solid. The solid was purified by column chromatography on silica gel (Dichloromethane:Ethyl acetate, 9:1 to 4:1) to afford compound 106 (10 mg, 34%) as a white solid. $^1$H NMR (CDCl$_3$): δ 6.51 (s, 1H), 4.26 (m, 2H), 3.88-3.65 (m, 8H), 3.28-3.14 (m, 5H), 2.18 (d, J=10.9, 1H), 1.75-1.40 (m, 5H), 1.38 (s, 3H), 1.21-0.98 (m, 6H), 0.93 (s, 3H), 0.85 (s, 3H), 0.83 (s, 3H). $^{13}$C NMR (CDCl$_3$): δ 159.5, 158.6, 138.1, 127.2, 110.0, 104.8, 66.9, 57.0, 55.8, 55.6, 52.6, 52.3, 48.0, 42.2, 41.6, 39.3, 38.3, 38.2, 33.3, 33.1, 21.3, 19.0, 18.4, 18.3, 17.4. MS m/z 491.9 (C$_{27}$H$_{41}$NO$_5$S+H$^+$).

Example 53

Synthesis of 2-{[(1R,10R,11S,16S)-3-(carboxymethoxy)-1,11,15,15-tetramethyl-8,8-dioxo-8Λ$^6$-thiatetracyclo[8.8.0.0$^{2,7}$.0$^{11,16}$]octadeca-2,4,6-trien-5-yl]oxy}acetic acid

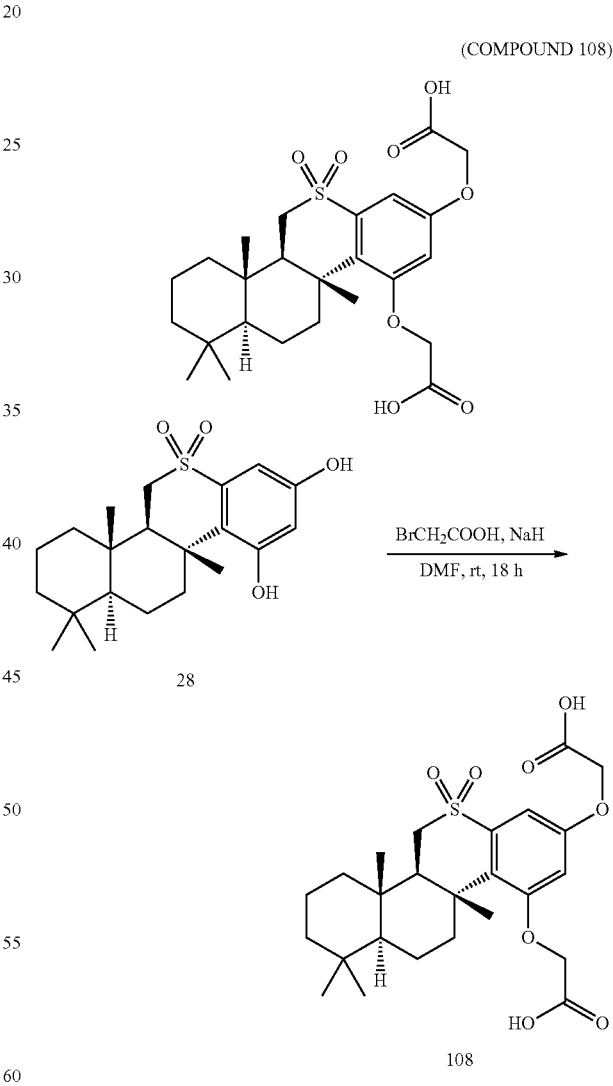

To a solution of compound 28 (100 mg, 0.264 mmol) and bromoacetic acid (94 mg, 0.68 mmol) in dimethylformamide (4 mL) was added sodium hydride (60%, 60 mg, 1.5 mmol), and the mixture was stirred at room temperature for 18 h. The reaction was quenched with hydrochloric acid (0.2 M, 10 mL) at 0° C. and extracted with ethyl acetate (1×20 mL, 2×10 mL).

The combined organic layers were washed with brine (5×20 mL) then dried (MgSO$_4$) and concentrated to afford a pale solid. The solid was dissolved in ethyl acetate (20 mL) and washed with aqueous sodium hydroxide (10 N, 15 mL). The aqueous layer was separated, acidified with hydrochloric acid (12 N, 15 mL), and extracted with ethyl acetate (3×20 mL). The extracts were combined then dried (MgSO$_4$) and concentrated to afford a pale solid. Purification by column chromatography on silica gel (Chloroform:Methanol, 18:4 to 1:1) afforded compound 108 (27 mg, 21%) as a pale solid. Yield 27 mg (21%). $^1$H NMR (CD$_3$OD): δ 6.86 (s, 1H), 6.66 (s, 1H), 4.87 (d, J=22.0 Hz, 4H), 3.65 (s, 1H), 3.55-3.46 (m, 1H), 2.20 (d, J=10.6 Hz 1H), 1.98 (s, 1H), 1.84-0.80 (m, 22H). $^{13}$C NMR [CD$_3$OD, missing 2×RCO$_2$H (Unable to observe the carbonyl signals in a variety of solvents)]: δ 158.3, 158.0, 139.7, 128.6, 105.4, 100.6, 66.6, 57.4, 45.5, 41.8, 41.6, 39.9, 39.2, 38.6, 37.9, 33.0, 32.2, 29.5, 20.4, 18.6, 18.2, 17.8, 16.4. MS m/z 493 (C$_{25}$H$_{34}$O$_8$S–H$^+$).

Example 54

Synthesis of (1R,10R,11S,16S)-3-methoxy-1,11,15,15-tetramethyl-5-[2-(morpholin-4-yl)-2-oxoethoxy]-8Λ$^6$-thiatetracyclo[8.8.0.0$^{2,7}$.0$^{11,16}$]octadeca-2,4,6-triene-8,8-dione (COMPOUND 110)

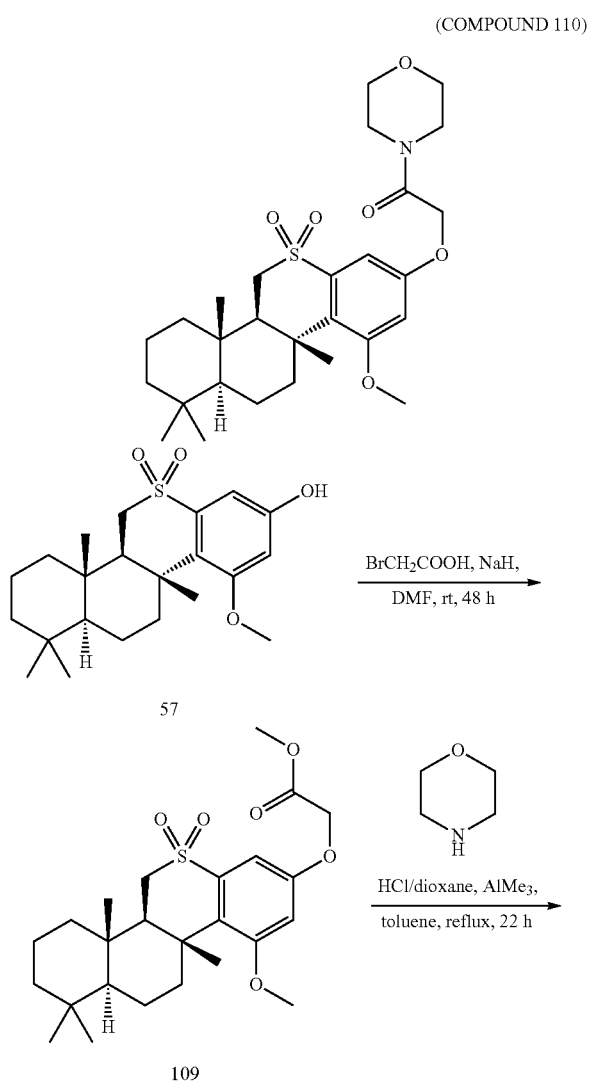

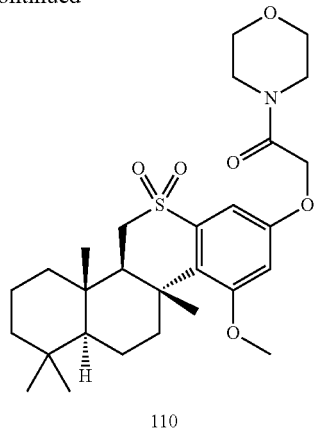

110

To a suspension of compound 57 (101 mg, 0.256 mmol) and sodium hydride (60%, 40 mg, 1.0 mmol) in dimethylformamide (4 mL) was added methyl bromoacetate (0.03 mL, 0.3 mmol), and the mixture was stirred for 2 days. The mixture was cooled to 0° C., quenched with hydrochloric acid (0.1M, 10 mL) added drop-wise and extracted with ethyl acetate (3×10 mL). The combined extracts were washed with brine (5×10 mL) then dried (MgSO$_4$) and concentrated to afford a pale solid. Purification by column chromatography on silica gel (Hexanes:Ethyl acetate, 4:1 to 2:1) afforded compound 109 (80 mg, 68%) as a white solid. $^1$H NMR (CDCl$_3$): δ 6.85 (d, J=1.6 Hz, 1H), 6.68 (s, 1H), 4.65 (s, 2H), 3.81 (s, 3H), 3.80 (s, 3H), 3.34-3.13 (m, 3H), 2.26 (d, J=12.0 Hz, 1H), 1.71-0.98 (m, 13H), 0.94 (s, 3H), 0.84 (s, 3H), 0.82 (s, 3H). $^{13}$C NMR (CDCl$_3$): δ 168.7, 159.3, 157.7, 140.0, 129.5, 105.4, 98.9, 65.5, 55.9, 55.9, 53.2, 52.5, 45.9, 41.9, 41.6, 39.5, 38.7, 37.7, 33.4, 33.1, 21.4, 18.9, 18.7, 18.5, 17.4.

Morpholine (0.03 mL, 0.3 mmol) was added to hydrochloric acid (4 M in dioxane, 0.71 mL) then stirred for 5 min and concentrated. The residue was dissolved in toluene (1.5 mL) and trimethylaluminum (2 M in toluene, 0.20 mL) was added at 0° C. under argon. The reaction was stirred at room temperature 1 h then a solution of compound 109 (80 mg, 0.17 mmol) in toluene (1 mL) was added and heated to reflux for 22 h. The reaction was quenched with hydrochloric acid (1 M, 10 mL) and extracted with ethyl acetate (2×10 mL) and dichloromethane (10 mL). The combined organic layers were concentrated and dissolved in dichloromethane (10 mL) then washed with brine (3×10 mL), dried (MgSO$_4$) and concentrated to afford a brown foam. Purification by column chromatography on silica gel (Hexanes:Ethyl acetate, 4:1 to neat ethyl acetate) afforded compound 110 (53 mg, 58%) as an off-white solid. $^1$H NMR (CDCl$_3$): δ 6.88 (d, J=2.5 Hz, 1H), 6.71 (d, J=2.4 Hz, 1H), 4.69 (s, 2H), 3.78 (s, 3H), 3.70-3.62 (m, 6H), 3.50-3.47 (m, 2H), 3.33-3.12 (m, 3H), 2.24 (d, J=11.9 Hz, 1H), 1.70-0.97 (m, 13H) 0.93 (s, 3H), 0.84 (s, 3H), 0.81 (s, 3H). $^{13}$C NMR (CDCl$_3$): δ 165.8, 159.3, 157.8, 140.1, 129.3, 104.9, 99.5, 67.0, 66.8, 55.9, 53.2, 45.9, 45.8, 42.5, 41.9, 41.6, 39.5, 38.7, 37.7, 33.4, 33.1, 21.4, 18.9, 18.6, 18.5, 17.4. MS m/z 520 ($C_{28}H_{41}NO_6S+H^+$).

Example 55

Synthesis of (1R,10R,11S,16S)-6-amino-3,5-dimethoxy-1,11,15,15-tetramethyl-8Λ[6]-thiatetracyclo[8.8.0.0[2,7].0[11,16]]octadeca-2,4,6-triene-8,8-dione

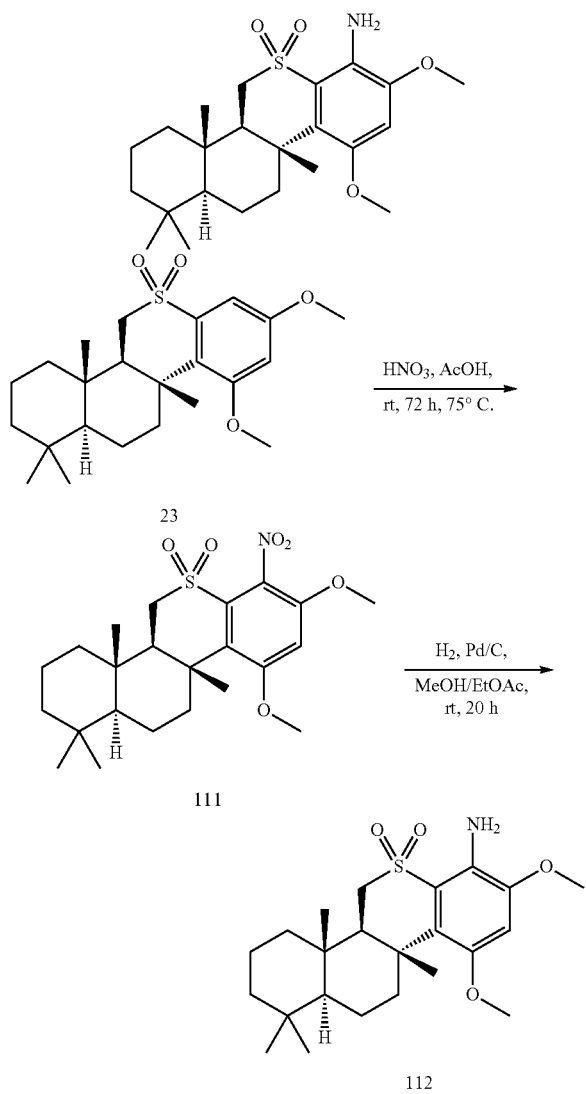

To a suspension of compound 23 (144 mg, 0.354 mmol) in glacial acetic acid (2 mL) under argon at room temperature was added 70% nitric acid (0.35 mL, 5.9 mmol) portion wise, and the mixture was stirred for 3 days. The mixture was heated to 75° C. for 3 h then cooled to room temperature, filtered and washed with water (20 mL). The filtrate was extracted with dichloromethane (3×10 mL). The filter cake was rinsed with dichloromethane (10 mL), and the combined organic layers were washed with brine (3×10 mL) then dried (MgSO$_4$) and concentrated to afford a yellow solid. Purification by column chromatography on silica gel (Hexanes:Ethyl acetate, 2:1 to 1:1) afforded compound 111 (44 mg, 28%) as a yellow solid. $^1$H NMR (CDCl$_3$): δ 6.64 (s, 1H), 3.91 (s, 3H), 3.90 (s, 3H), 3.35-3.15 (m, 3H), 2.41 (d, J=11.6 Hz, 1H), 1.68-0.99 (m, 13H), 0.93 (s, 3H), 0.87 (s, 3H), 0.83 (s, 3H).

To a suspension of compound 111 (32 mg, 0.070 mmol) in methanol (2 mL) and ethyl acetate (2 mL) under argon at room temperature was added palladium on charcoal (10%, 35 mg). The reaction flask was degassed and filled with hydrogen then stirred for 20 h. The mixture was filtered through Celite, washed with ethyl acetate, and concentrated to afford a yellow oil. Purification by column chromatography on silica gel (Hexanes:Ethyl acetate, 4:1 to 1:1) afforded compound 112 (18 mg, 61%) as a yellow solid. $^1$H NMR (CDCl$_3$): δ 6.57 (s, 1H), 4.70 (br s, 2H), 3.85 (s, 3H), 3.77 (s, 3H), 3.27-3.21 (m, 3H), 2.24-2.20 (m, 1H), 1.71-0.98 (m, 13H), 0.93 (s, 3H), 0.86 (s, 3H), 0.82 (s, 3H). $^{13}$C NMR (CDCl$_3$): δ 149.8, 146.8, 130.3, 128.0, 121.9, 102.6, 57.1, 56.2, 55.9, 52.3, 47.9, 41.9, 41.7, 39.5, 38.5, 33.4, 33.1, 29.9, 21.4, 19.2, 19.1, 18.5, 17.3. MS m/z 422 ($C_{23}H_{35}NO_4S+H^+$).

Example 56

His-hSHIP1 Activity of Representative Compounds

Test compounds were dissolved in 95% ethanol to form stock solutions. Before screening, the stock solutions were diluted with Phosphatase Assay Buffer (20 mM Tris-HCL, 10 mM MgCl2 pH 7.5, 0.02% Tween 20) to form working assay solutions that contained 10% ethanol. The assay was carried out on 96-well microtiter plates using a modified procedure of that reported by Ong et al., *Blood* 110, 1942-1949, 2007 and Yang et al., *Org Lett* 7, 1073-1076, 2005, both of which references are incorporated herein by reference in their entirety.

Each reaction contained 5 µL of His-hSHIP1 enzyme (15-20 ng), 10 µL of the substrate, 1,3,4,5-inositol tetrakisphosphate (IP4; 50 µM final), 5 µL of Phosphatase Assay Buffer, and 5 µL of test compound at various concentrations in 10% ethanol (0-300 µM final). Control blanks were also prepared by replacing His-hSHIP1 enzyme, IP4, or test compounds with Phosphatase Assay Buffer. After adding the reaction components in a 96-well microtiter plate on ice, the reaction was mixed by briefly shaking the plate vigorously. The reaction was then incubated at 37° C. for 15 min with gentle shaking followed by addition of 100 µL of Biomol Green Reagent (BIOMOL, PA, USA) to terminate the reaction. The free phosphate released from IP4 by His-hSHIP1 bound to the Biomol Green Reagent, turning the solution green in colour. After incubating the mixture for 20 min at room temperature for colour development, the absorbance was read with a SpectraMax Plus 96-well plate reader (Molecular Devices, Sunnyvale, Calif., USA) at a wavelength of 650 nm.

According to the above assay, the representative compounds listed in Table 2 below were found to activate His-hSHIP1 enzyme at concentrations ≦300 µM. Percent (%) activation in Table 2 is expressed as a percentage increase relative to background. Scoring is expressed as follows: + (<50%); ++ (≧50% but <65%); +++ (≧65%).

TABLE 2

| Cpd. No. | Scoring |
|---|---|
| 5 | ++ |
| 6 | + |
| 14 | + |
| 15 | +++ |

TABLE 2-continued

| Cpd. No. | Scoring |
| --- | --- |
| 16 | +++ |
| 23 | +++ |
| 25 | ++ |
| 26 | + |
| 27 | ++ |
| 28 | +++ |
| 29 | ++ |
| 39 | ++ |
| 43 | + |
| 44 | ++ |
| 50 | + |
| 57 | + |
| 61 | + |
| 62 | ++ |
| 65 | ++ |
| 66 | + |
| 73 | + |
| 76 | + |
| 78 | + |
| 79 | + |
| 80 | + |
| 81 | + |
| 84 | + |
| 85 | + |
| 86 | + |
| 87 | ++ |
| 88 | + |
| 89 | + |
| 90 | + |
| 91 | + |
| 92 | + |
| 93 | + |
| 94 | + |
| 95 | + |
| 96 | + |
| 98 | + |
| 100 | + |
| 102 | + |
| 104 | + |
| 105 | + |
| 106 | + |

Example 57

Activity of Representative Compounds on Akt Phosphorylation in Lymphocytes

Phosphorylation of AKT has been shown to be modulated by SHIP1 (Helgason et al., *J Exp Med* 191, 781-794, 2000). Jurkat (PTEN−/SHIP1−) or Molt-4 (PTEN−/SHIP1+) cells were starved in serum free RPMI for overnight. In a 15 mL conical tube, 2-3 million serum starved cells (1 million cells per mL) were treated with various concentrations of test compound (0.1, 1, or 10 µM final in 0.1% DMSO) for 30 min at 37° C. followed by stimulation with 100 ng/mL of IGF-1 for 1 hour at 37° C. After stimulation, cells were washed once with ice-cold DPBS and lysed with Lysis Buffer (20 mM Tris-HCl, pH 7.5, 140 mM NaCl, 1% NP-40, Complete Mini Protease Inhibitor Cocktail, 10 mM NaF, 1 mM $Na_3VO_4$, 1 mM β-glycerolphosphate) on ice for 30 min with vortexing every 10 min. Samples were then centrifuged at 13,000 rpm for 20 min, and supernatants were collected as total cell lysate samples. Protein concentration was determined using bicinchonic acid assay, and about 15 µg of total protein from each sample was loaded and separated on a 4-12% Tris-Glycine gel. After SDS-PAGE, proteins were transferred from the gel to a nitrocellulose membrane. The membrane was blocked in 5% BSA in PBS containing 0.1% Tween-20 (PBS-T) for 1 hour at room temperature before probing with primary antibodies for overnight at 4° C. The following antibodies were used: mouse anti-SHIP1 (1:500 dilution; Santa Cruz, Calif., USA), rabbit anti-phospho-Akt(Ser473) (1:1000 dilution; Cell Signaling Technologies, MA, USA), rabbit anti-Akt (1:1000; Cell Signaling Technologies, MA, USA), and rabbit anti-actin (1:2000; Cell Signaling Technologies, MA, USA). The membrane was then incubated with goat anti-rabbit or anti-mouse secondary antibodies (1:3000) for 1 hour at room temperature. Target proteins on the membrane were detected with ECL solution and exposed on a film.

According to the above assay, the representative compounds listed in Table 3 below were found to inhibit Akt phosphorylation at ≦10 µM in Molt-4 (SHIP1+), but not Jurkat (SHIP1−) lymphocytes. Scoring in Table 3 is expressed as follows: + (inhibits Akt phosphorylation at 10 µM); − (no effect on Akt phosphorylation at 10 µM).

TABLE 3

| Cpd. No. | Molt-4 (SHIP1+) | Jurkat (SHIP1−) |
| --- | --- | --- |
| 6 | + | − |
| 28 | + | − |
| 50 | + | − |

Example 58

Activity of Representative Compounds on Passive Cutaneous Anaphylaxis in Mice

The activity of representative compounds on passive cutaneous anaphylaxis in mice was evaluated according to the procedures disclosed by Ovary, *J Immunol* 81, 355-357, 1958 and Halpern et al., *Br J Pharmacol Chemother* 20, 389-398, 1963, both of which are incorporated herein by reference in their entirety.

To induce a passive cutaneous anaphylaxis, mice underwent intradermal ear inoculation on their right ear with 25 ng in 20 µL of anti-DNP-IgE. The left ears were untreated and served as negative controls. Twenty-four hours after inoculation, all mice were administered test compound by oral gavage (PO). Sixty minutes after oral administration, mice were given a tail vein injection of 2% Evan's blue (0.2 µm filtered, in 200 µL saline) followed by a second tail IV injection of 100 µg DNP-HSA (in 200 µL). Sixty minutes following the DNP-HSA injection, mice were euthanized using $CO_2$ inhalation. Subsequently, ear biopsies were performed by taking four millimetre punches from both ears, which then underwent Evan's Blue extraction using formamide incubation in 96 well plates. Eighty µL of eluents were transferred to flat-bottom 96-well plates and absorbance read using SpectraMax M5 spectrophotometer (Molecular Devices, Sunnyvale, Calif., USA) at 620 nm. Background readings from all samples were taken at 740 nm and subtracted from the 620 nm readings. Data were reported as OD.

According to the above assay, the representative compounds listed in Table 4 below were found to inhibit allergen-induced passive cutaneous anaphylaxis at doses less than 20 mg/kg. Scoring in Table 4 is expressed as follows: + (1-30% inhibition); ++ (31-50% inhibition); +++ (>50% inhibition).

TABLE 4

| Cpd. No. | Scoring |
|---|---|
| 6 | ++ |
| 28 | +++ |
| 43 | + |

Example 59

Activity of Representative Compounds on Passive Cutaneous Anaphylaxis in Rats

The activity of representative compounds on passive cutaneous anaphylaxis in rats was evaluated according to the procedures disclosed by Goose et al., *Immunology* 16, 749-760, 1969, which is incorporated herein by reference in its entirety. To induce a passive cutaneous anaphylaxis, rats underwent dorsal intradermal inoculation with 50 μL of anti-ovalbumin-IgE. Sixteen hours after inoculation, all rats were administered test compound by oral gavage (PO). Sixty minutes after oral administration, rats were given a tail vein injection of 5 mg Evan's blue and 1 mg ovalbumin. Sixty minutes following the ovalbumin injection, rats were euthanized using $CO_2$ inhalation. Subsequently, skin edema was visualized, measured and scored. When tested in this assay, representative Compound. No. 6 and representative Compound No. 28 were found to inhibit allergen-induced passive cutaneous anaphylaxis at doses less than 100 mg/kg (29% and 38% inhibition respectively at 100 mg/kg; and 14% and 26% inhibition respectively at 30 mg/kg).

Example 60

Activity of Representative Compounds on Carrageenan Paw Edema in Mice

The activity of representative compounds on carrageenan paw edema in mice was evaluated according to the procedures disclosed by Winter et al., *Proc Soc Exp Biol Med* 111, 544-547, 1962, which is incorporated herein by reference in its entirety. To induce edema in the paw, test compounds were administered orally one hour before intraplantar injection of the right hind paw with carrageenan (50 μL of 1% suspension). Hind paw edema, as a measure of inflammation, was recorded using a plethysmometer (Ugo Basile, Italy) 4 hours after λ-carrageenan administration. When tested in this assay, representative Compound No. 6 was found to inhibit allergen-induced carrageenan-induced paw edema at doses less than 30 mg/kg (24% inhibition).

Example 61

Activity of Representative Compounds on Inhibition of OPM2 Proliferation

Test compounds were dissolved in 100% DMSO to form stock solutions. Prior to screening, the stock solutions were diluted with complete media (RPMI 1640 containing 10% fetal calf serum, 2 mM L-glutamine and 50 U/mL each of penicillin and streptomycin) to form working assay solutions that contain 0.2% DMSO. The assay was initiated by adding 30,000 OPM2 cells (in 50 μL) to 50 μL of representative compounds at concentrations ranging from 0.03 to 30 μM. The cells were incubated for 72 hours in a humidified $CO_2$ incubator with the addition of 10 μM BrdU for the final 6 hours according to the directions from the Roche BrdU Cell Proliferation ELISA kit used to detect proliferation (Roche, Cat. No. 11 647 229 001). OPM2 cells incubated in 0.1% DMSO in complete media were used as a negative control and the PI3Kα Inhibitor 2 (3-[4-(4-morpholinyl)thieno[3,2-d]pyrimidin-2-yl-phenol, Cayman Chemical, Cat. No. 10010177) was used as a positive control for inhibition of proliferation. At the end of the incubation, the plate containing the labeled cells was centrifuged, the supernatant removed and the cell pellets dried at 60° C. for 1 hour and stored at 4° C. until further analysis. Analysis of BrdU incorporation was done according to the manufacturer's instructions.

According to the above assay, representative compounds listed in Table 5 below were found to inhibit OPM2 proliferation at a concentration of 30 μM. The percent (%) inhibition of proliferation in Table 5 was determined by the following formula:

% Inhibition=(1−(value for proliferation in the presence of test article/value for proliferation in 0.1% DMSO control))*100

Scoring is expressed based on the inhibition of proliferation according to the following system: + (<25%); ++ (≧25% but <75%); +++ (≧75%).

TABLE 5

| Cpd. No. | Scoring |
|---|---|
| 57 | +++ |
| 62 | ++ |
| 78 | +++ |
| 81 | ++ |
| 87 | ++ |
| 89 | +++ |
| 92 | +++ |
| 102 | +++ |
| 108 | + |
| 110 | + |
| 112 | +++ |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound of the following structure (I):

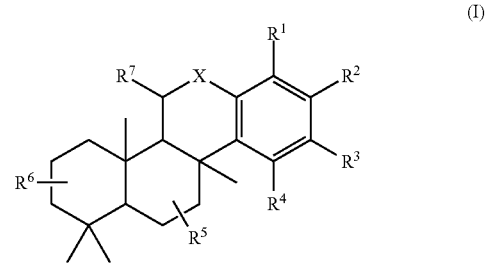

or a stereoisomer or pharmaceutically acceptable salt thereof, wherein:

X is O or S(O)$_p$ where p is 0, 1 or 2;

$R^1$, $R^2$, $R^3$, $R^4$, $R^5$ and $R^6$ are independently hydrogen, halogen, hydroxyl, cyano, unsubstituted or substituted alkyl, unsubstituted or substituted alkoxy, —COOR$^8$, —NR$^9$R$^{10}$, —CONR$^{11}$R$^{12}$, —NR$^{13}$COR$^{14}$ or —OSO$_2$R$^{15}$;

$R^7$ is hydrogen; and $R^8$, $R^9$, $R^{10}$, $R^{11}$, $R^{12}$, $R^{13}$, $R^{14}$ and $R^{15}$ are independently hydrogen, unsubstituted or substituted alkyl or unsubstituted or substituted alkoxy, or $R^9/R^{10}$ or $R^{11}/R^{12}$ taken together with the nitrogen to which they are attached form a heterocycle.

2. The compound of claim 1, wherein X is O of the following structure (II):

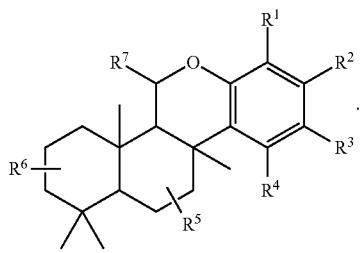

(II)

3. The compound of claim 1, wherein X is S(O)$_p$ of the following structure (III):

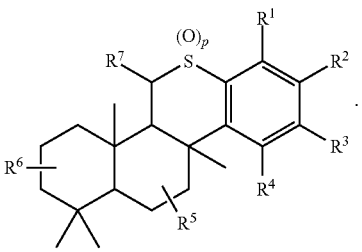

(III)

4. The compound of claim 3, wherein p is 0 of the following structure (III-a):

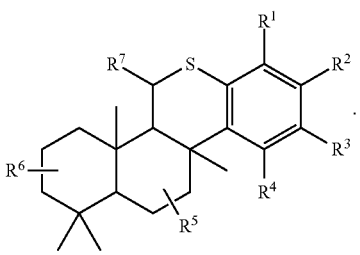

(III-a)

5. The compound of claim 3, wherein p is 1 of the following structure (III-b):

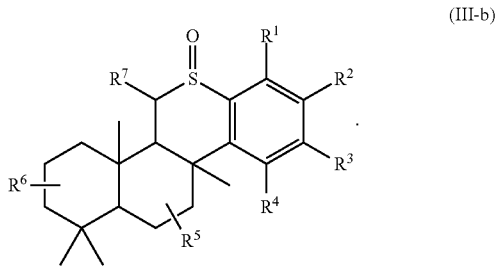

(III-b)

6. The compound of claim 3, wherein p is 2 of the following structure (III-c):

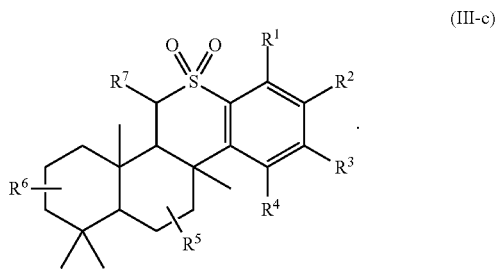

(III-c)

7. The compound of claim 1 of the following stereochemistry:

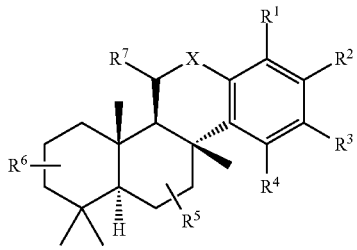

8. The compound of claim 1, wherein $R^5$ and $R^6$ are both hydrogen.

9. The compound of claim 1, wherein $R^1$ and $R^3$ are both hydrogen.

10. The compound of claim 1, wherein $R^2$ and $R^4$ are both hydrogen.

11. The compound of claim 1, wherein $R^1$, $R^2$, $R^3$ and $R^4$ are independently hydrogen, hydroxyl, alkyl or alkoxy.

12. The compound of claim 1, wherein $R^1$, $R^2$, $R^3$ and $R^4$ are independently hydrogen, hydroxyl, alkyl, alkoxy, cyano, amino, —COOH, —OSO$_2$R$^{15}$ or —CONHCH$_3$.

13. The compound of claim 1, wherein at least one of $R^1$, $R^2$, $R^3$ and $R^4$ is —NR$^9$R$^{10}$ or —CONR$^{11}$R$^{12}$, and wherein $R^9/R^{10}$ or $R^{11}/R^{12}$ taken together with the nitrogen to which they are attached form a heterocycle.

14. The compound of claim 1, wherein at least one of $R^1$, $R^2$, $R^3$ and $R^4$ is —COOR$^8$, —NR$^9$R$^{10}$, —CONR$^{11}$R$^{12}$, —NR$^{13}$COR$^{14}$, wherein $R^8$, $R^9$, $R^{10}$, $R^{11}$, $R^{12}$, $R^{13}$ and $R^{14}$ are independently substituted alkyl or —O-(substituted alkyl), wherein the alkyl is substituted with —C(=O)R$^a$, —C(=O)OR$^a$, —C(=O)NR$^b$R$^c$, —OC(=O)NR$^b$R$^c$, —NR$^b$R$^c$, —NR$^a$C(═O)R$^b$, —NR$^a$C(═O)OR$^b$ or —NR$^a$C(═O)NR$^b$R$^c$, and wherein R$^a$, R$^b$ and R$^c$ are the same or different and independently hydrogen or alkyl.

15. The compound of claim 1, wherein at least one of R$^1$, R$^2$, R$^3$ and R$^4$ is substituted alkyl or —O-(substituted alkyl), wherein the alkyl is substituted with —C(═O)R$^a$, —C(═O)OR$^a$, —C(═O)NR$^b$R$^c$, —OC(═O)NR$^b$R$^c$, —NR$^b$R$^c$, —NR$^a$C(═O)R$^b$, —NR$^a$C(═O)OR$^b$ or —NR$^a$C(═O)NR$^b$R$^c$, and wherein R$^a$, R$^b$ and R$^c$ are the same or different and independently hydrogen or alkyl, or R$^b$/R$^c$ taken together with the nitrogen to which they are attached form a heterocycle.

16. A compound selected from the group consisting of:

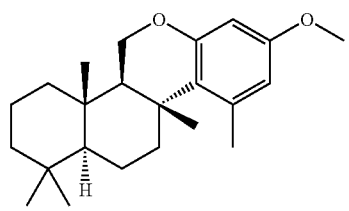
;

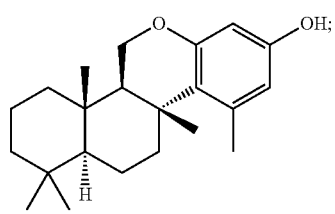
;

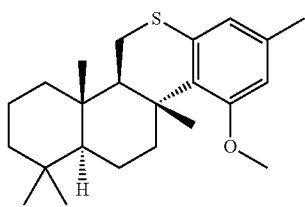
;

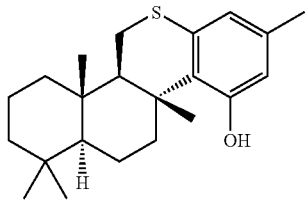
;

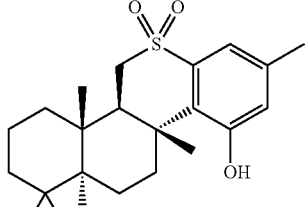
;

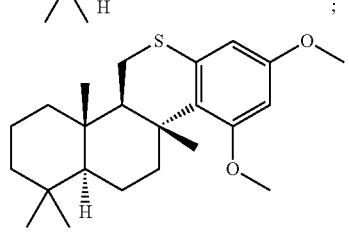
;

-continued

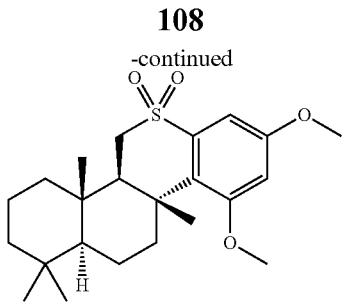
;

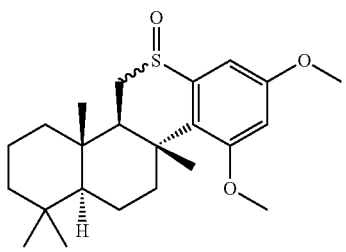
;

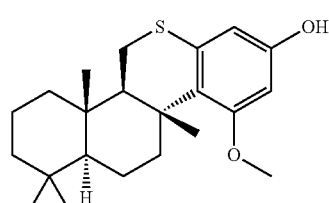
;

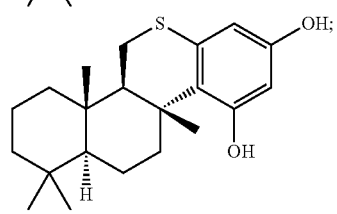
;

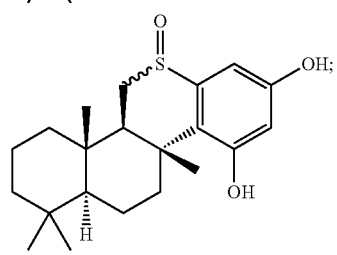
;

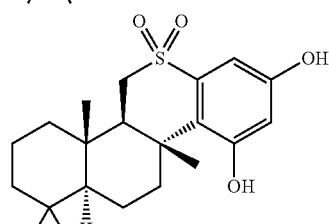
;

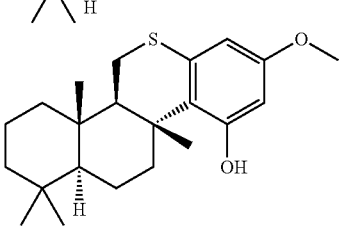
;

109
-continued
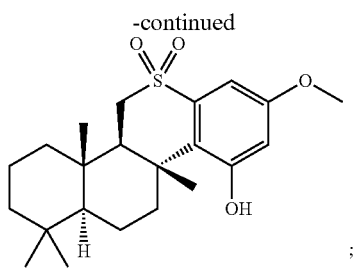
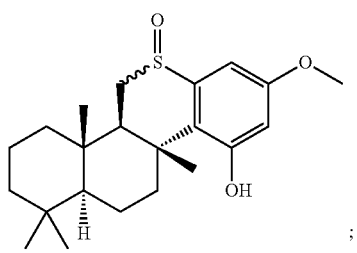
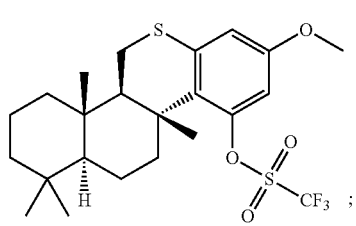
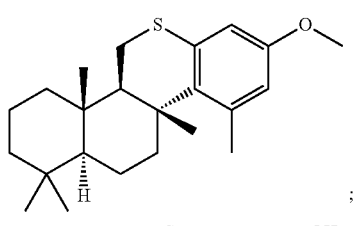
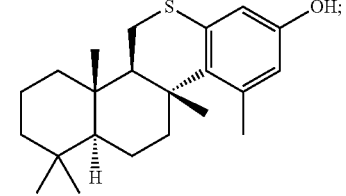
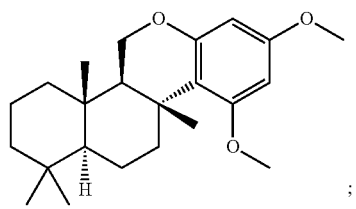
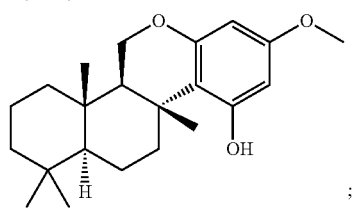
110
-continued
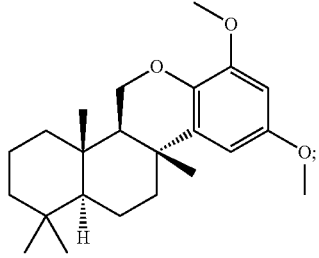
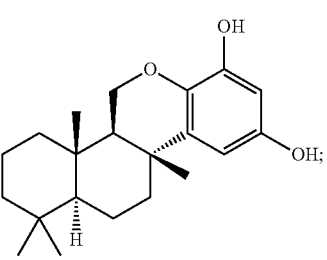
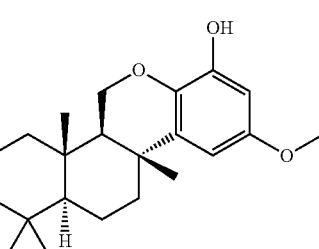
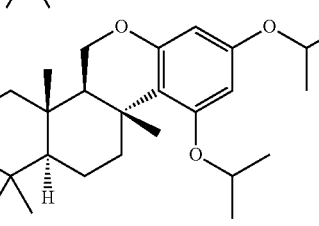
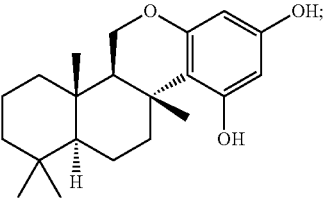
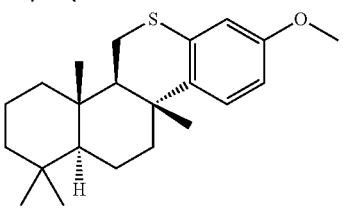
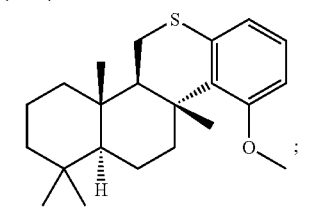

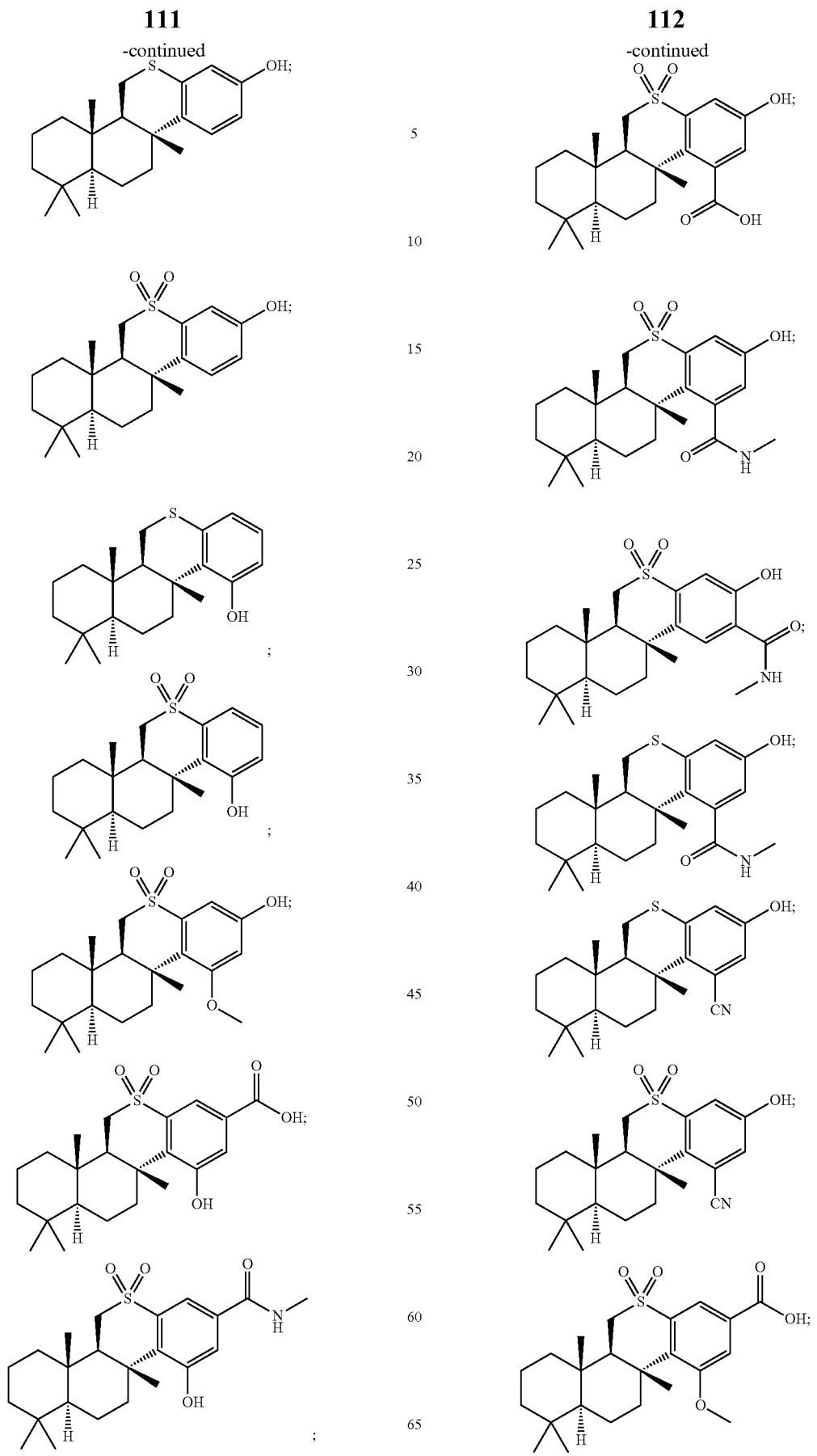

113
-continued
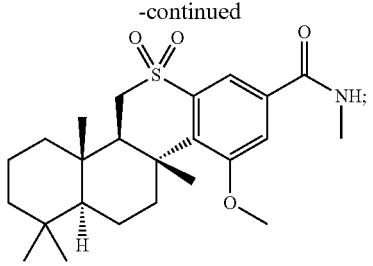
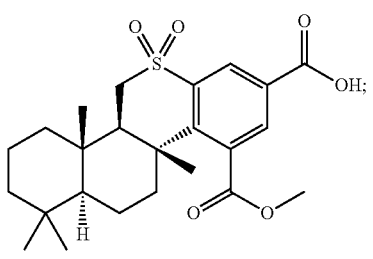
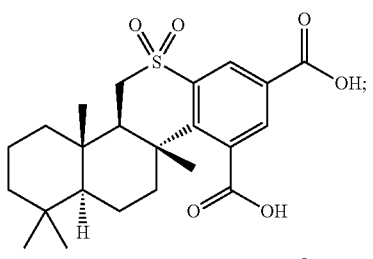
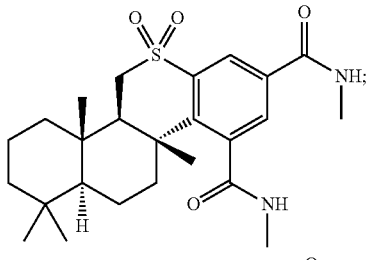
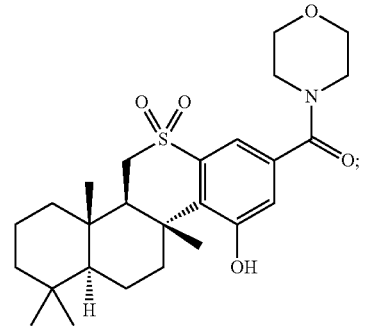
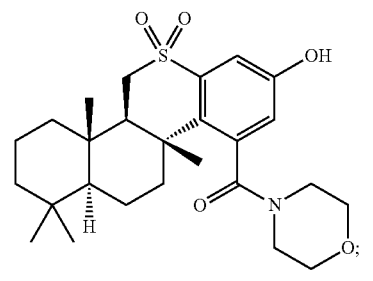
114
-continued
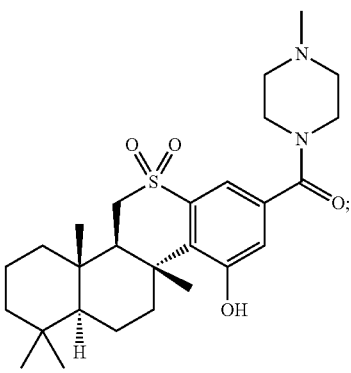
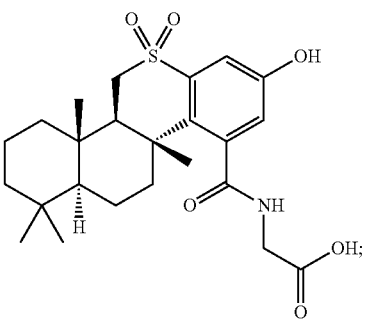
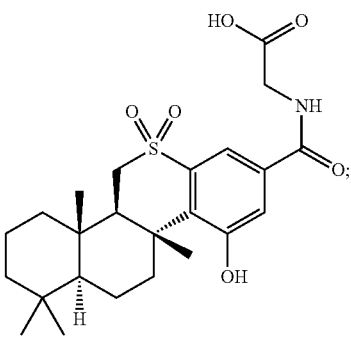
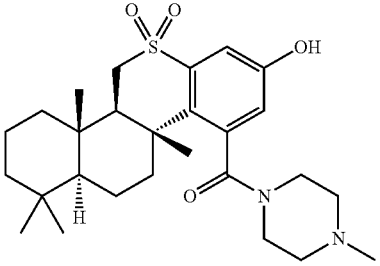
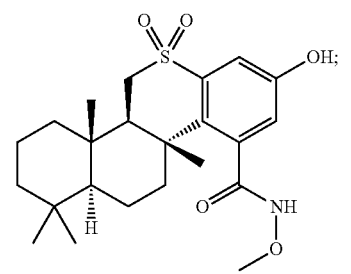

-continued
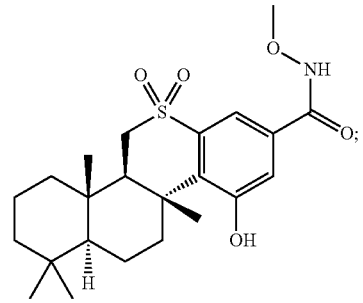
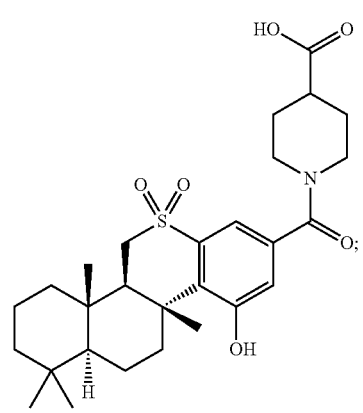
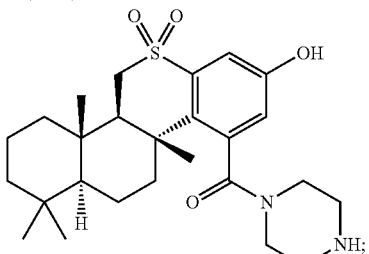
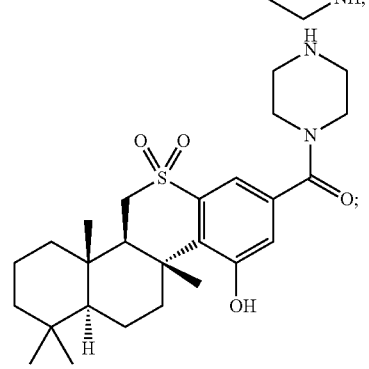
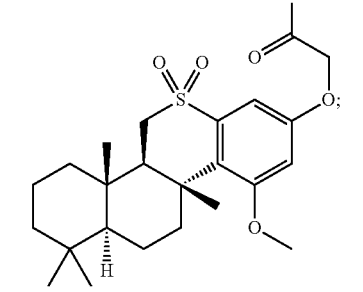
-continued
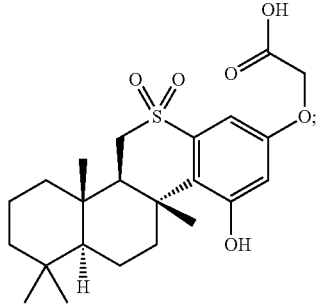
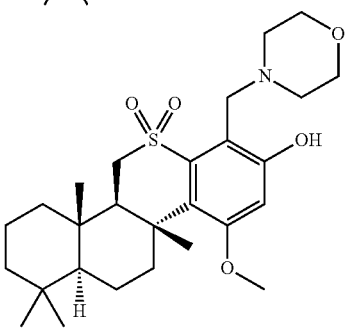
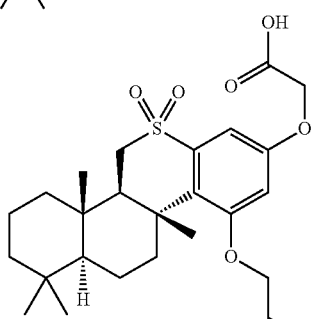
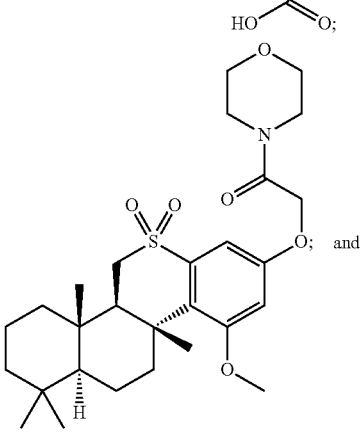
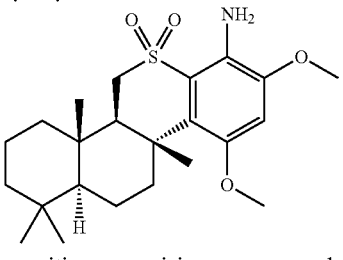
17. A composition comprising a compound of claim 1 in combination with a pharmaceutically acceptable carrier or diluent.
* * * * *